United States Patent
Chodosh et al.

(10) Patent No.: US 12,111,317 B2
(45) Date of Patent: Oct. 8, 2024

(54) FLOW CYTOMETRY-BASED PLATFORM FOR THE DETECTION, ENUMERATION, AND ISOLATION OF DISSEMINATED TUMOR CELLS IN BONE MARROW ASPIRATES

(71) Applicant: THE TRUSTEES OF THE UNIVERSITY OF PENNSYLVANIA, Philadelphia, PA (US)

(72) Inventors: Lewis Chodosh, West Chester, PA (US); Elizabeth Chislock, Media, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 791 days.

(21) Appl. No.: 16/620,580

(22) PCT Filed: Jun. 8, 2018

(86) PCT No.: PCT/US2018/036611
§ 371 (c)(1),
(2) Date: Dec. 9, 2019

(87) PCT Pub. No.: WO2018/227050
PCT Pub. Date: Dec. 13, 2018

(65) Prior Publication Data
US 2020/0166510 A1   May 28, 2020

Related U.S. Application Data

(60) Provisional application No. 62/517,335, filed on Jun. 9, 2017.

(51) Int. Cl.
| | | |
|---|---|---|
| *C07K 16/32* | (2006.01) | |
| *A61K 49/00* | (2006.01) | |
| *G01N 15/10* | (2006.01) | |
| *G01N 15/14* | (2006.01) | |
| *G01N 33/574* | (2006.01) | |
| *G01N 15/01* | (2024.01) | |

(52) U.S. Cl.
CPC .......... *G01N 33/57415* (2013.01); *A61K 49/0058* (2013.01); *C07K 16/32* (2013.01); *G01N 15/10* (2013.01); *G01N 15/1459* (2013.01); *G01N 15/01* (2024.01); *G01N 2015/1006* (2013.01); *G01N 2800/50* (2013.01)

(58) Field of Classification Search
CPC ................................. G01N 33/57415
USPC ......................................... 435/7.23
See application file for complete search history.

(56) References Cited

U.S. PATENT DOCUMENTS

| | | | |
|---|---|---|---|
| 8,956,536 B2 | 2/2015 | Yu | |
| 2001/0000751 A1* | 5/2001 | Schmitz | G01N 33/54326 435/7.2 |
| 2012/0021435 A1 | 1/2012 | Hiltawsky | |

OTHER PUBLICATIONS

Yao et al (International Journal of Cancer, 2013, 133: 2925-2933).*
Moore et al (Cancer Res, 2009, 69(2_Supp): Abstract 302).*
Kamel et al (Journal of the Egyptian National Cancer Institute, 2016, 28: 31-37).*
Braun et al (NEJM, 2005, 353: 793-802).*
Fehm et al (Cancer, 2006, 107(5): 885-892).*
Byers, T. (CA Journal, vol. 49, No. 6, Nov./Dec. 1999).*

* cited by examiner

*Primary Examiner* — Sean E Aeder
(74) *Attorney, Agent, or Firm* — Riverside Law LLP

(57) ABSTRACT

The present invention provides compositions and methods for detecting and isolating disseminated tumor cells (DTCs) from breast cancer in a bone marrow aspirate of a subject. The invention further provides methods of treating breast cancer in the subject.

2 Claims, 78 Drawing Sheets
Specification includes a Sequence Listing.

SEQUENCE LISTING

```
<160> NUMBER OF SEQ ID NOS: 2

<210> SEQ ID NO 1
<211> LENGTH: 32
<212> TYPE: DNA
<213> ORGANISM: Artificial Sequence
<220> FEATURE:
<223> OTHER INFORMATION: Chemically Synthesized

<400> SEQUENCE: 1
aacaaatgaa tgatgcacat catggtggct gg                           32

<210> SEQ ID NO 2
<211> LENGTH: 32
<212> TYPE: DNA
<213> ORGANISM: Artificial Sequence
<220> FEATURE:
<223> OTHER INFORMATION: Chemically Synthesized

<400> SEQUENCE: 2
aacaaatgaa tgatgcacgt catggtggct gg                           32
```

FLOW CYTOMETRY-BASED PLATFORM FOR THE DETECTION, ENUMERATION, AND ISOLATION OF DISSEMINATED TUMOR CELLS IN BONE MARROW ASPIRATES

CROSS-REFERENCE TO RELATED APPLICATIONS

This application is a U.S. national phase application filed under 35 U.S.C. § 371 claiming priority to International Patent Application No. PCT/US2018/036611, filed Jun. 8, 2018, which is entitled to priority under 35 U.S.C. § 119(e) to U.S. Provisional Patent Application No. 62/517,335, filed Jun. 9, 2017, the contents of each of which are incorporated by reference herein in their entireties.

STATEMENT REGARDING FEDERALLY SPONSORED RESEARCH OR DEVELOPMENT

This invention was made with government support under Grant No. R01CA143296 awarded by the National Institutes of Health (NIH). The government has certain rights in the invention.

BACKGROUND OF THE INVENTION

Tumor recurrence is a major clinical problem in breast cancer, occurring in up to 30% of patients years or even decades after initial treatment. Most recurrent tumors occur at distant metastatic sites and arise from disseminated tumor cells (DTCs) that originate from the primary tumor and persist in their host at secondary sites. Since recurrent breast cancer is presently incurable, detecting and therapeutically targeting these cells is a critical clinical need. Breast cancer patients with bone marrow DTCs, as determined by immunohistochemical detection of cytokeratin-positive tumor cells in bone marrow aspirates, have markedly increased risk of tumor recurrence and decreased overall survival. Further, persistence of bone marrow DTCs following adjuvant therapy is associated with poor clinical outcomes. Together, these findings suggest that bone marrow DTCs are a biomarker for risk of tumor recurrence and likely constitute a precursor population giving rise to recurrent tumors.

Current methods of identifying bone marrow DTCs involve density gradient centrifugation and immunohistochemistry of cells expressing epithelial cytokeratins. These methods are insensitive due to cell loss and the low sensitivity of immunohistochemistry, miss DTCs that have undergone endothelial to mesenchymal transition (EMT), and don't enable molecular analysis of the identified DTCs.

Thus, there is a need in the art for compositions and methods for identifying DTCs. The present invention satisfies this unmet need.

SUMMARY OF THE INVENTION

In one embodiment, the invention relates to a composition for detecting a disseminated tumor cell (DTC) in a sample from a subject comprising at least one labeled molecule that specifically binds to at least one marker expressed by the DTC. In one embodiment, the composition comprises at least one labeled molecule that specifically binds to at least one of HER2, EpCAM, CD49C, EGFR, c-Met and pan-cytokeratin.

In one embodiment, the composition further comprises at least one labeled molecule that specifically binds to at least one marker that is not expressed by a DTC. In one embodiment, the composition comprises at least one labeled molecule that specifically binds to at least one of CD43 and CD45.

In one embodiment, at least one labeled molecule is a labeled antibody or a labeled aptamer.

In one embodiment, the DTC is a breast cancer DTC.

In one embodiment, the sample is a bone marrow aspirate.

In one embodiment, the invention relates to a method of detecting a DTC in a sample from a subject comprising the steps of contacting the sample with at least one labeled molecule that specifically binds to at least one marker expressed by the DTC and analyzing the sample. In one embodiment, at least one labeled molecule specifically binds to at least of HER2, EpCAM, CD49C, EGFR, c-Met and pan-cytokeratin.

In one embodiment, the method further comprises contacting the sample with at least one labeled molecule that specifically binds to at least one marker that is not expressed by a DTC.

In one embodiment, at least one labeled molecule specifically binds to at least one of CD43 and CD45.

In one embodiment, at least one labeled molecule is a labeled antibody or a labeled aptamer.

In one embodiment, the DTC is a breast cancer DTC.

In one embodiment, the sample is a bone marrow aspirate.

In one embodiment, the analyzing step is performed using flow cytometry.

In one embodiment, the method further comprises a step of isolating the DTC.

In one embodiment, the method further comprises a step of analyzing the isolated DTC.

In one embodiment, the method further comprises the step of pre-enriching the sample for DTC prior to analyzing the sample. In one embodiment, the method of pre-enriching the sample for DTC comprises depletion of at least one of lysed red blood cells (RBC), cellular debris, unbound antibodies and non-DTC hematopoietic cells. In one embodiment, the method step of pre-enriching the sample for DTC comprises use of a pre-enrichment device which functions in-line with a fluorescence-activated cell sorting (FACS) device.

In one embodiment, the invention relates to a method of diagnosing a subject as having an increased risk of breast cancer, the method comprising the steps of obtaining a sample from the subject, identifying a DTC in the sample, and diagnosing the subject as having an increased risk of breast cancer based on the identified DTC.

In one embodiment, the sample is a bone marrow aspirate.

In one embodiment, the method of identifying a DTC comprises the steps of contacting the sample with at least one labeled molecule that specifically binds to at least one marker expressed by the DTC and analyzing the sample. In one embodiment, at least one labeled molecule specifically binds to at least one of HER2, EpCAM, CD49C, EGFR, c-Met and pan-cytokeratin.

In one embodiment, the method further comprises the step of contacting the sample with at least one labeled molecule that specifically binds to at least one marker that is not expressed by a DTC.

In one embodiment, at least one labeled molecule specifically binds to at least one of CD43 and CD45.

In one embodiment, at least one labeled molecule is a labeled antibody or a labeled aptamer.

In one embodiment, the analyzing step is performed using flow cytometry.

In one embodiment, the method further comprises a step of isolating the DTC.

In one embodiment, the method further comprises a step of analyzing the isolated DTC.

In one embodiment, the method further comprises the step of pre-enriching the sample for DTC prior to analyzing the sample. In one embodiment, the method of pre-enriching the sample for DTC comprises depletion of at least one of lysed red blood cells (RBC), cellular debris, unbound antibodies and non-DTC hematopoietic cells. In one embodiment, the method step of pre-enriching the sample for DTC comprises use of a pre-enrichment device which functions in-line with a fluorescence-activated cell sorting (FACS) device.

In one embodiment, the invention relates to a method of treating or preventing a disease or disorder associated with a DTC in a subject in need thereof, the method comprising the steps of obtaining a sample from the subject, identifying a DTC in the sample, and administering to the subject an effective amount of a therapeutic agent.

In one embodiment, the sample is a bone marrow aspirate.

In one embodiment, the disease or disorder is cancer.

In one embodiment, the DTC is a breast cancer DTC, and the therapeutic agent comprises a therapeutic agent for treatment of breast cancer.

In one embodiment, the invention relates to a kit for detecting a disseminated tumor cell (DTC) in a sample from a subject comprising at least one labeled molecule that specifically binds to at least one marker expressed by the DTC. In one embodiment, the kit comprises at least one labeled molecule that specifically binds to at least one of HER2, EpCAM, CD49C, EGFR, c-Met and pan-cytokeratin.

In one embodiment, the kit further comprises at least one labeled molecule that specifically binds to at least one marker that is not expressed by a DTC. In one embodiment, the kit comprises at least one labeled molecule that specifically binds to at least one of CD43 and CD45.

In one embodiment, at least one labeled molecule is a labeled antibody or a labeled aptamer.

BRIEF DESCRIPTION OF THE DRAWINGS

The following detailed description of exemplary embodiments of the invention will be better understood when read in conjunction with the appended drawings. For the purpose of illustrating the invention, there are shown in the drawings exemplary embodiments. It should be understood, however, that the invention is not limited to the precise arrangements and instrumentalities of the embodiments shown in the drawings.

Figure 12:
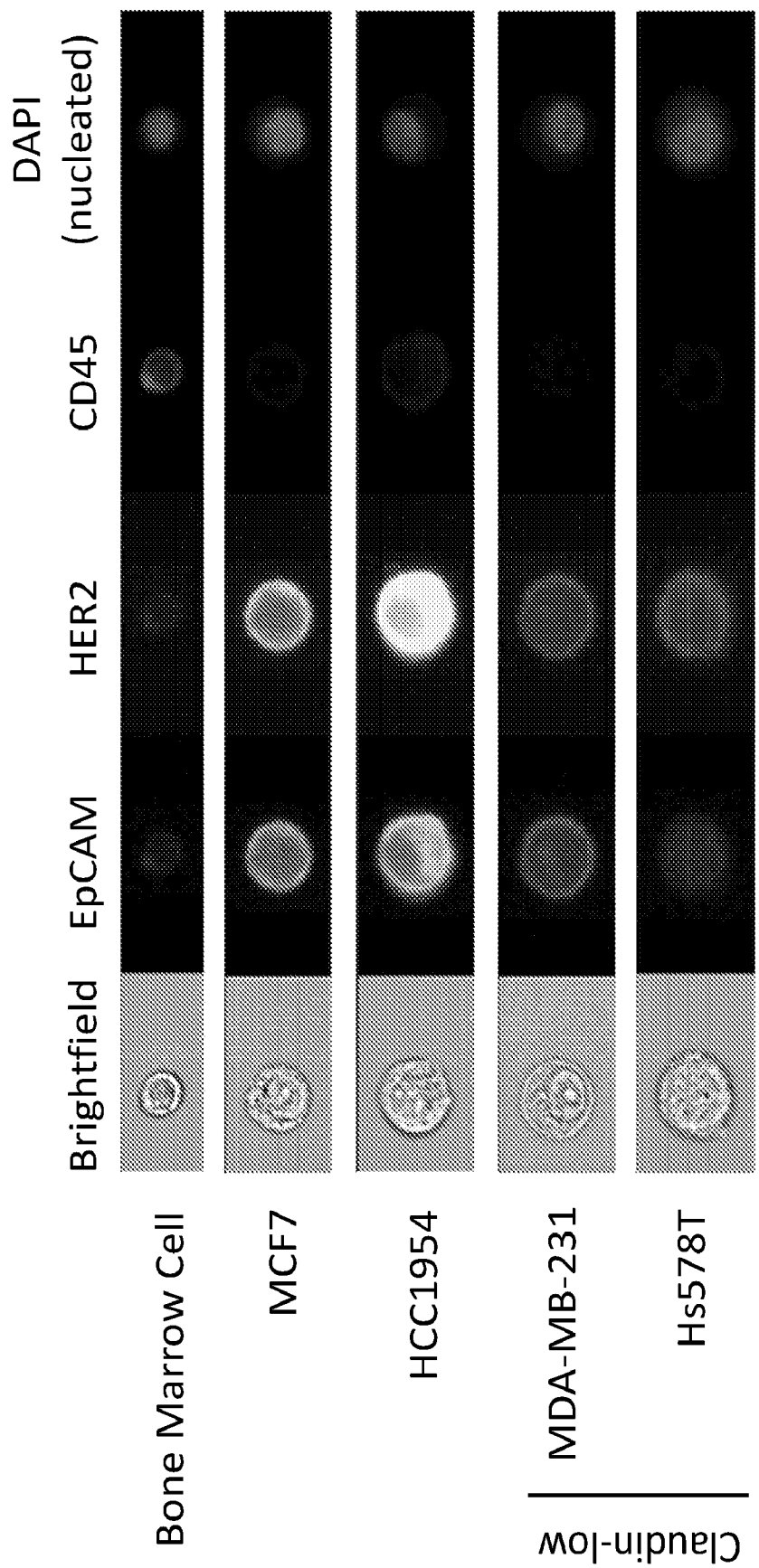

FIG. 12 depicts the results of exemplary experiments demonstrating that breast cancer cells lines show EpCAM and HER2 staining whereas bone marrow cells show CD45 staining using an ImageStream® analysis.

Figure 13:
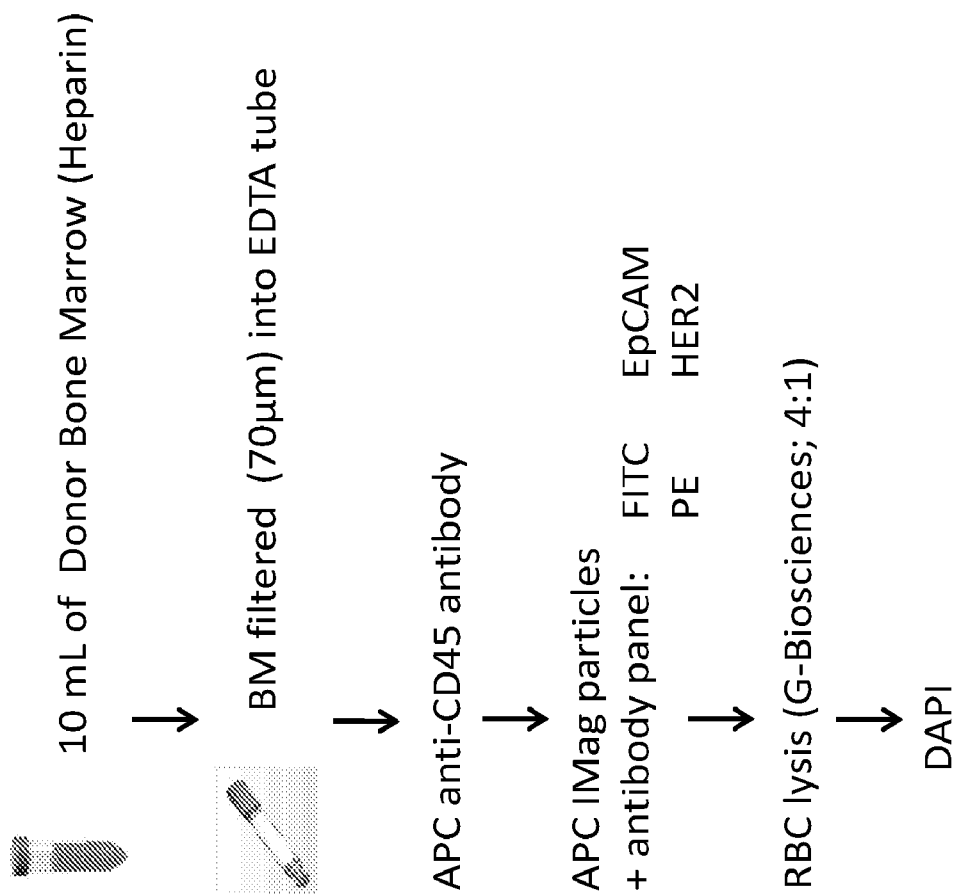

FIG. 13 depicts a flow diagram showing the staining workflow used for assessment of bone marrow cells from healthy donors.

Figure 14:
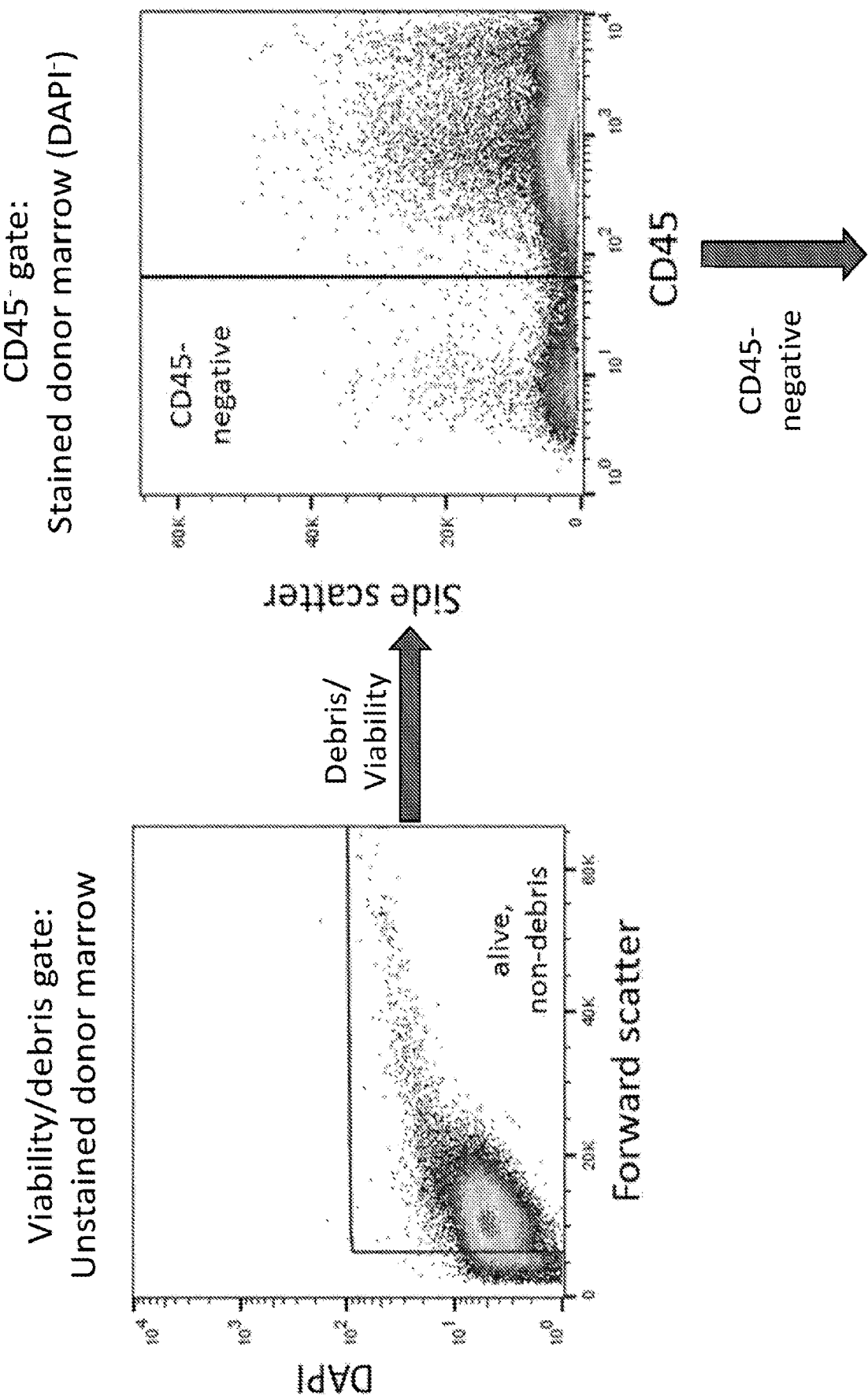

FIG. 14 depicts the results of exemplary experiments demonstrating the gating strategy used for assessment of bone marrow cells from healthy donors.

Figure 15:
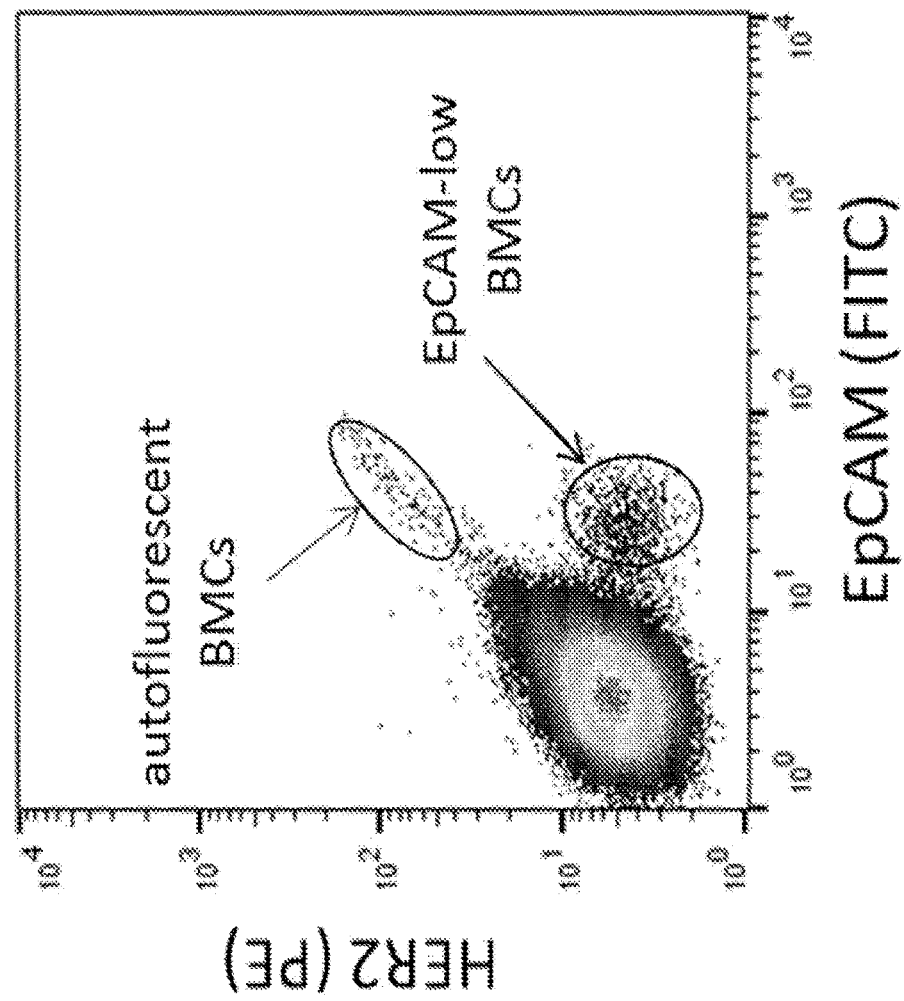

FIG. 15 depicts the results of exemplary experiments demonstrating the EpCAM/HER2 staining of healthy donor bone marrow.

Figure 16:
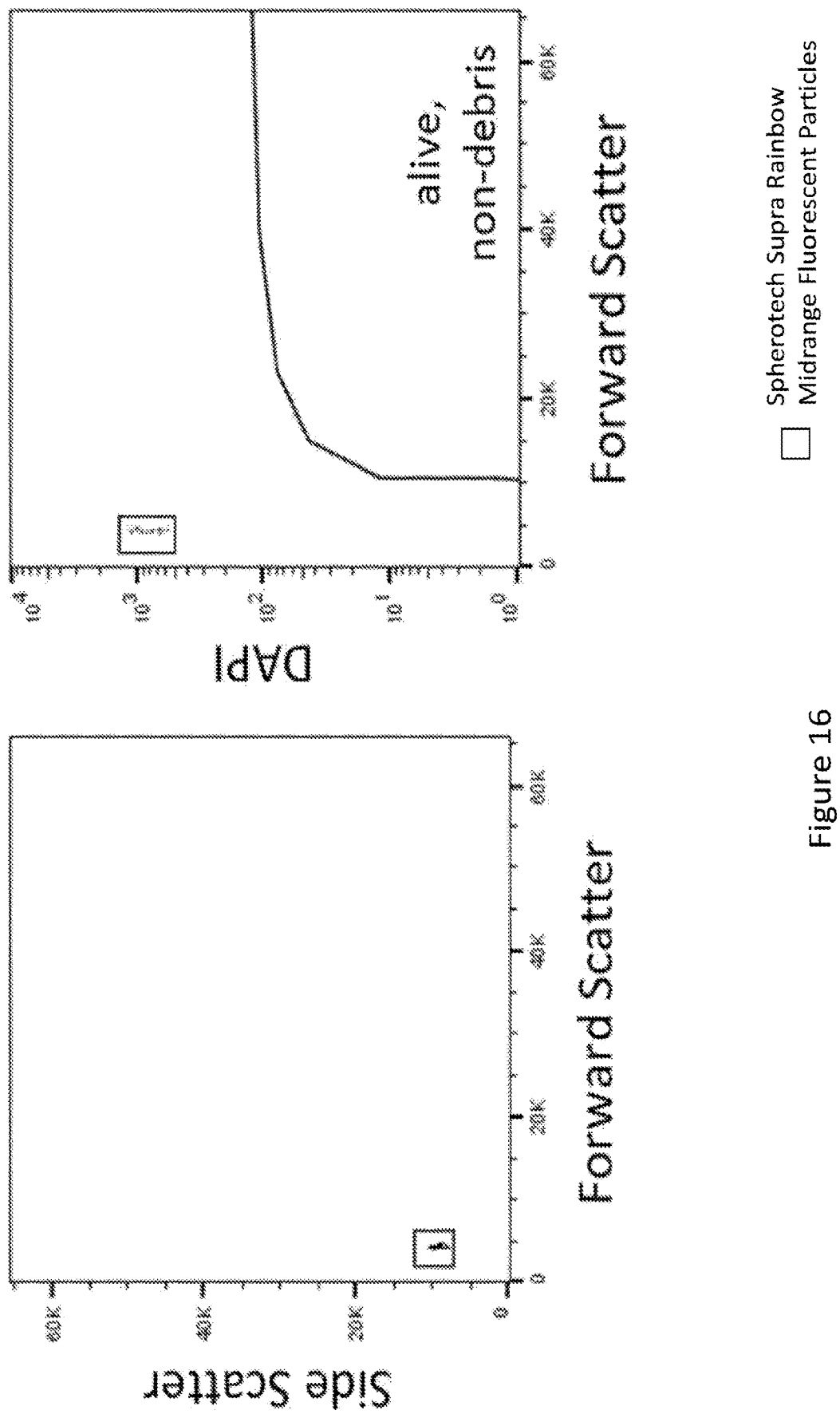
Figure 16:
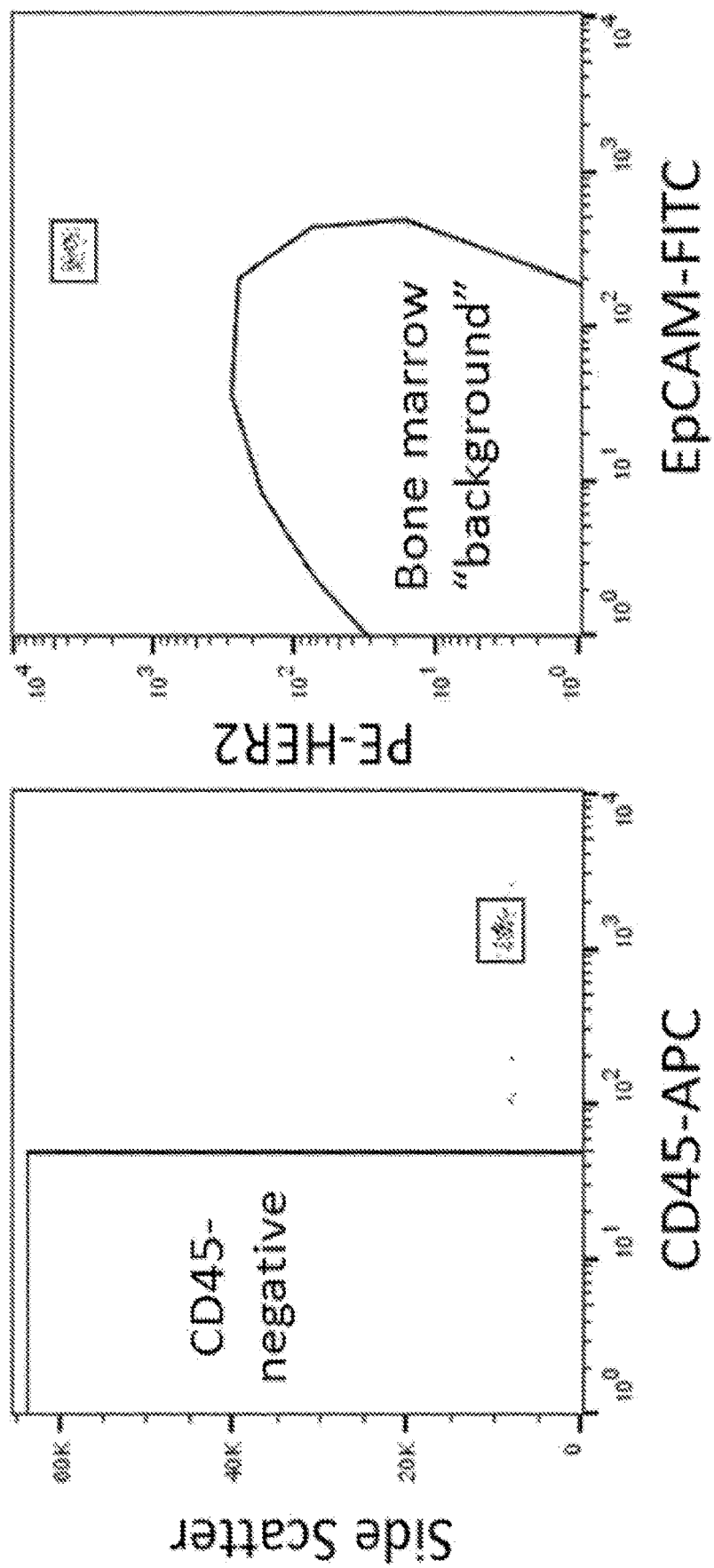

FIG. 16 depicts the standardization of influx settings and gates. Fluorescent calibration particles ensure consistency of fluorescence measurements over time. Spherotech SPHERO™ Supra Rainbow particles are run on the BD Influx™ and PMT detector settings adjusted such that the beads are detected at the same signal intensity in each channel as for previous runs (red boxes).

Figure 17:
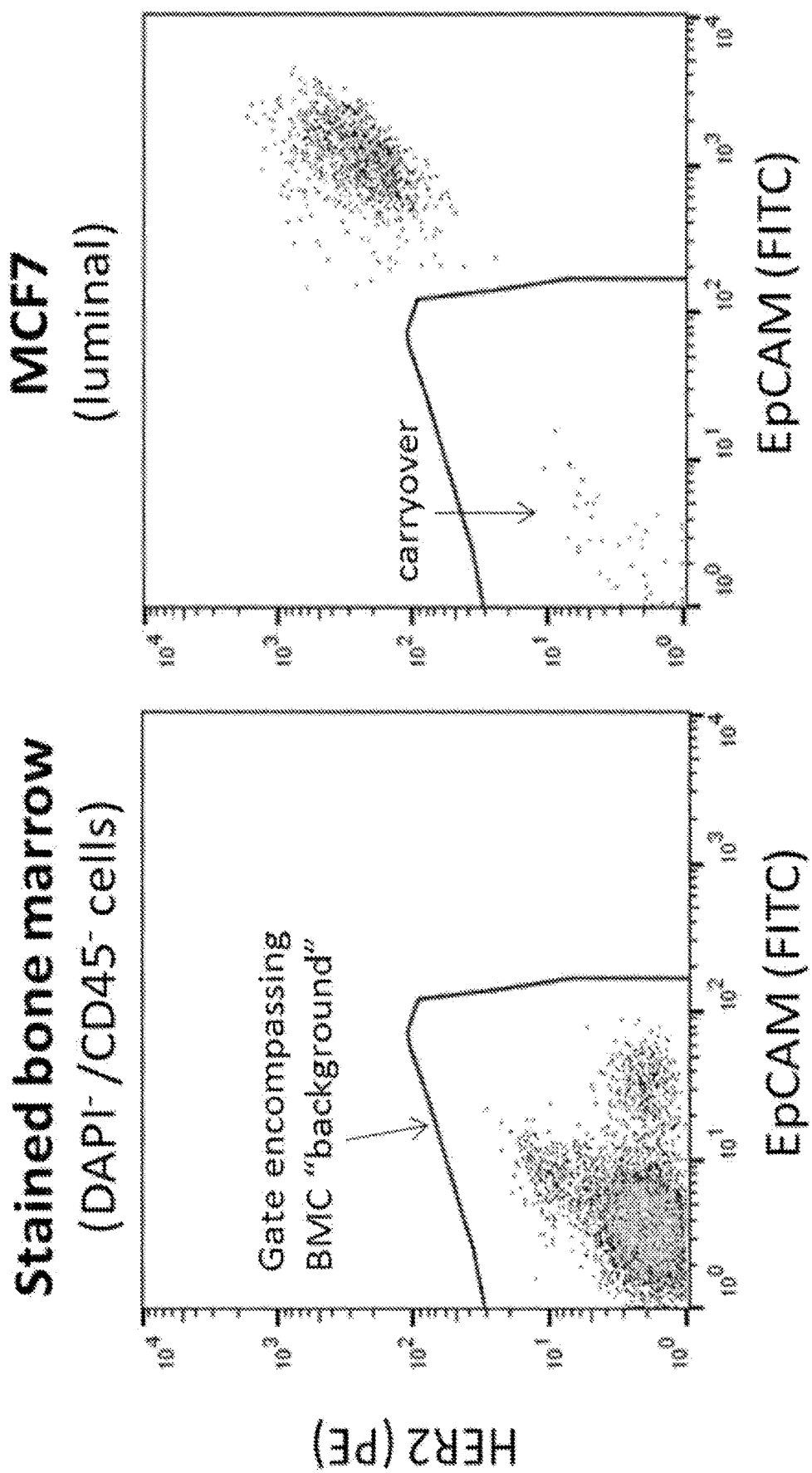
Figure 17:
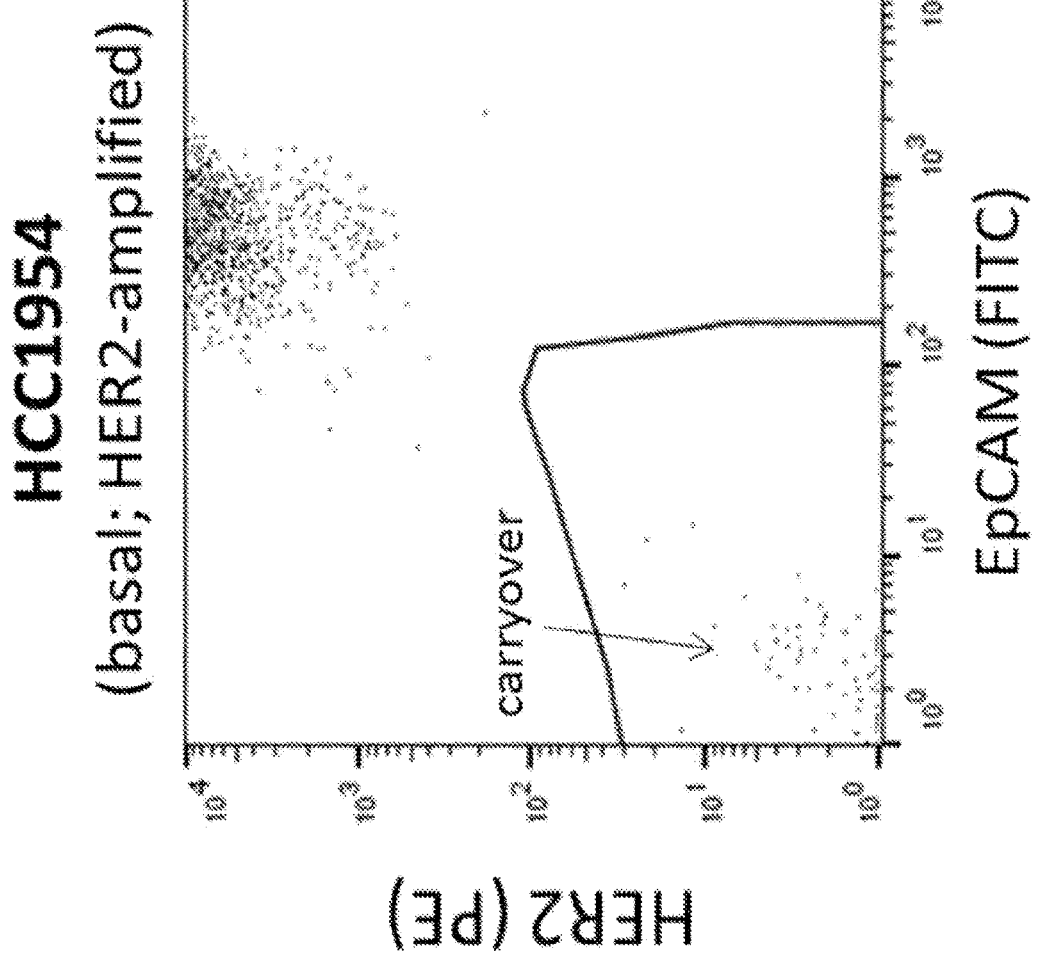

FIG. 17 depicts the results of exemplary experiments demonstrating EpCAM/HER2 labeling of human breast cancer cell lines vs. donor bone marrow.

Figure 18:
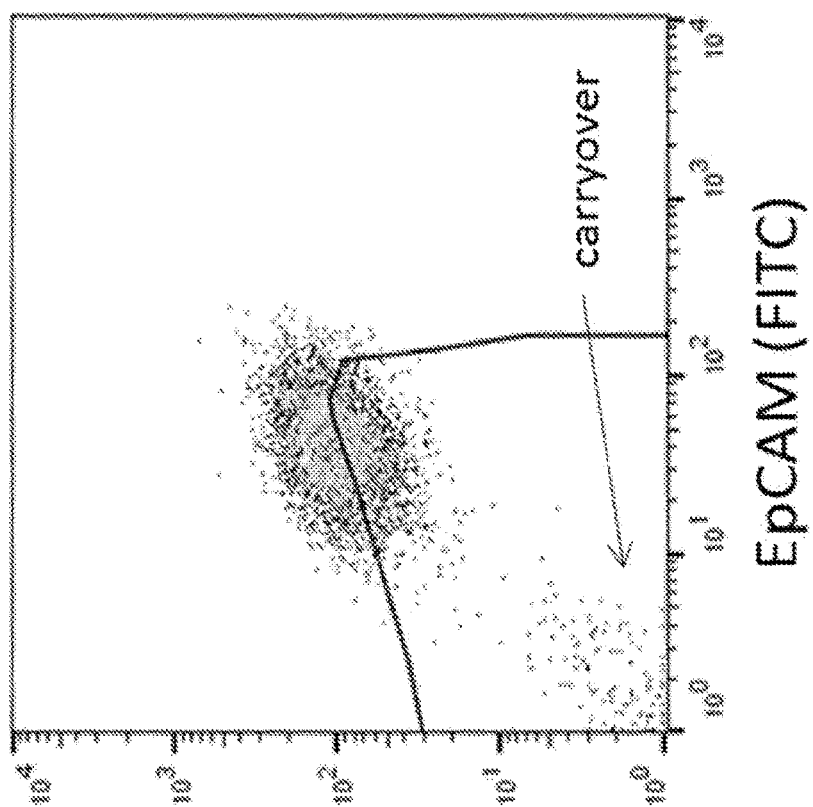
Figure 18:
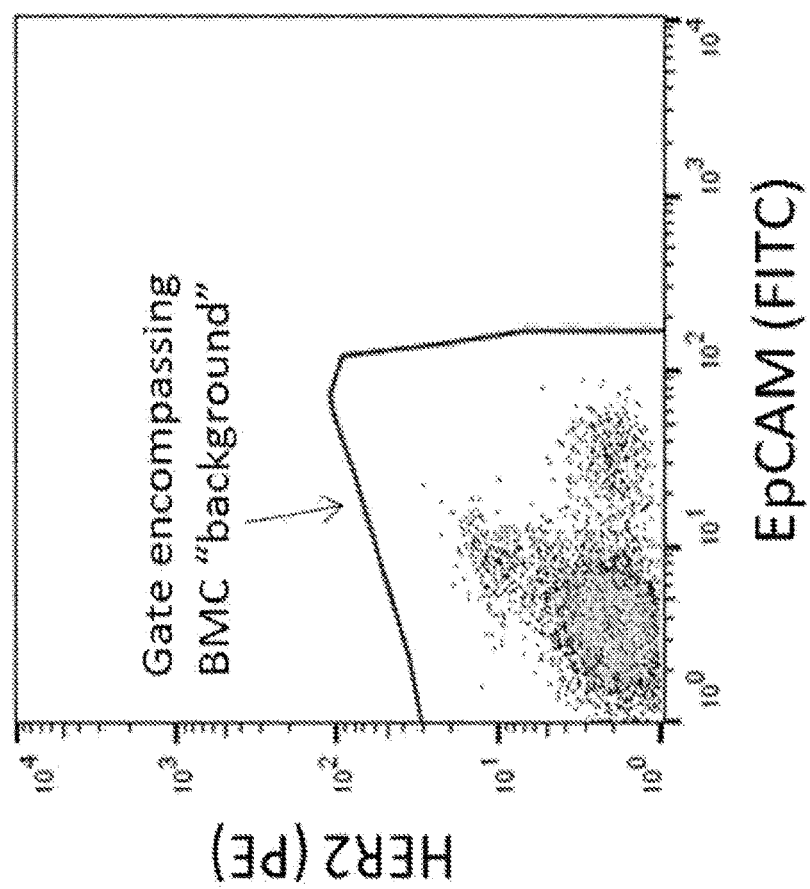
Figure 18:
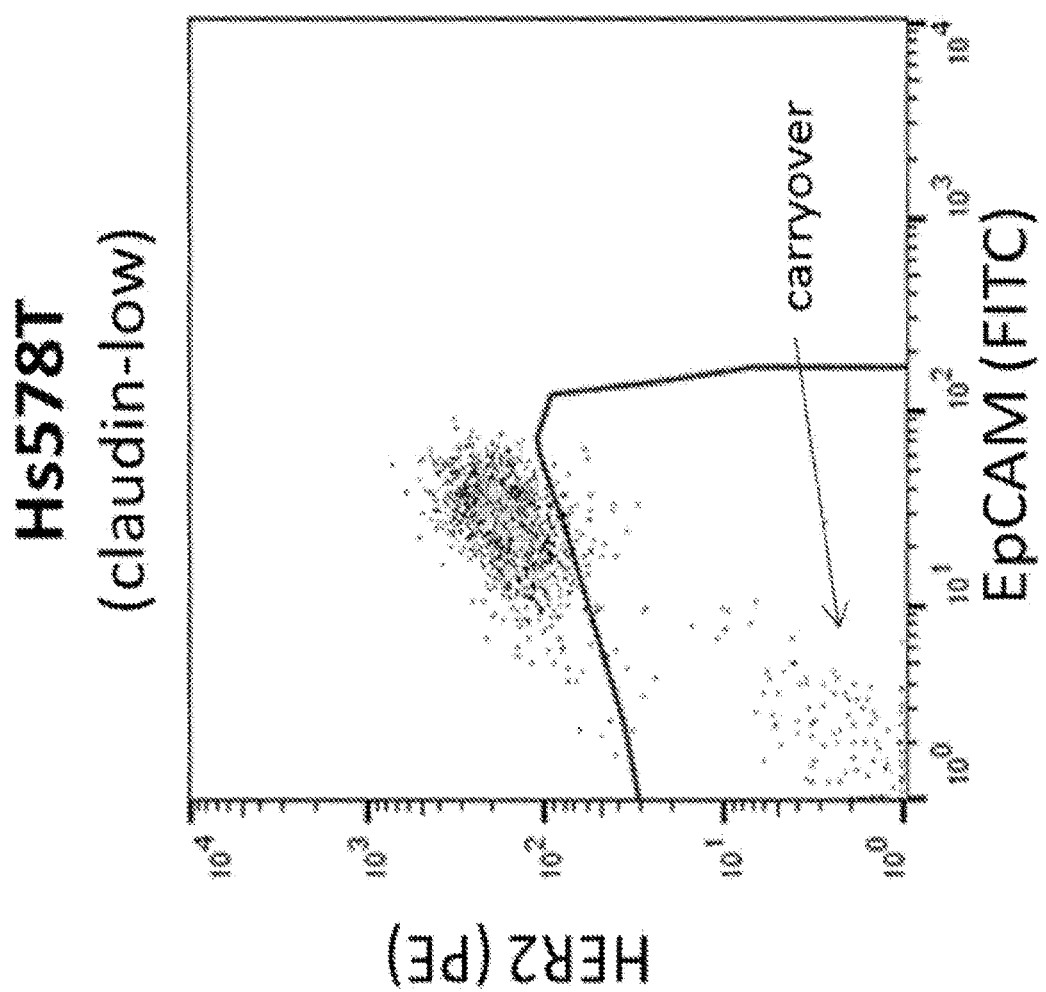

FIG. 18 depicts the results of exemplary experiments demonstrating EpCAM/HER2 labeling of claudin-low human breast cancer cell lines vs. donor bone marrow.

Figure 19:
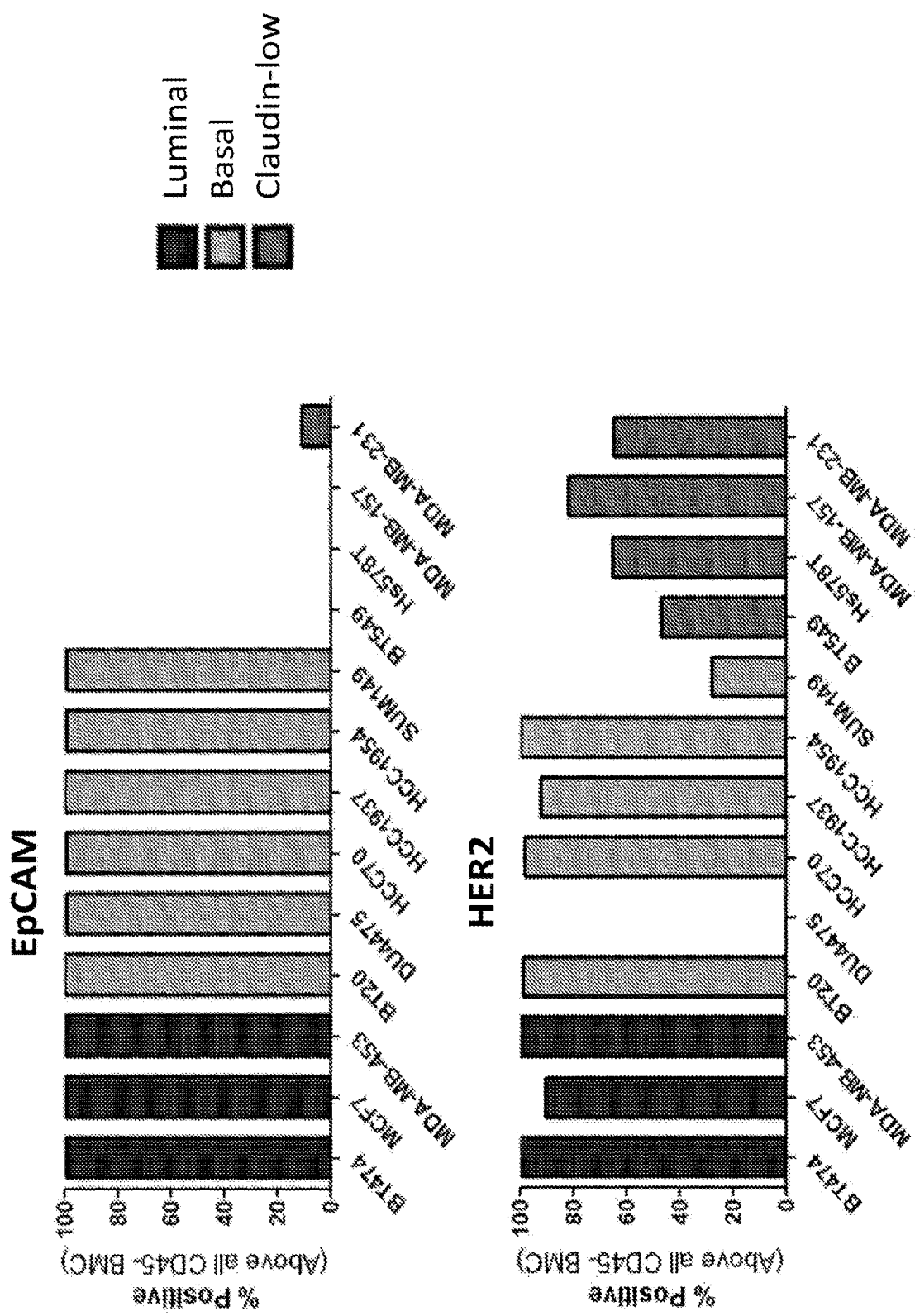

FIG. 19 depicts a summary of the results of exemplary experiments demonstrating the percentage of human breast cancer cell lines expressing higher levels of EpCAM or HER2 than observed in CD45− negative cells in donor bone marrow.

Figure 20:
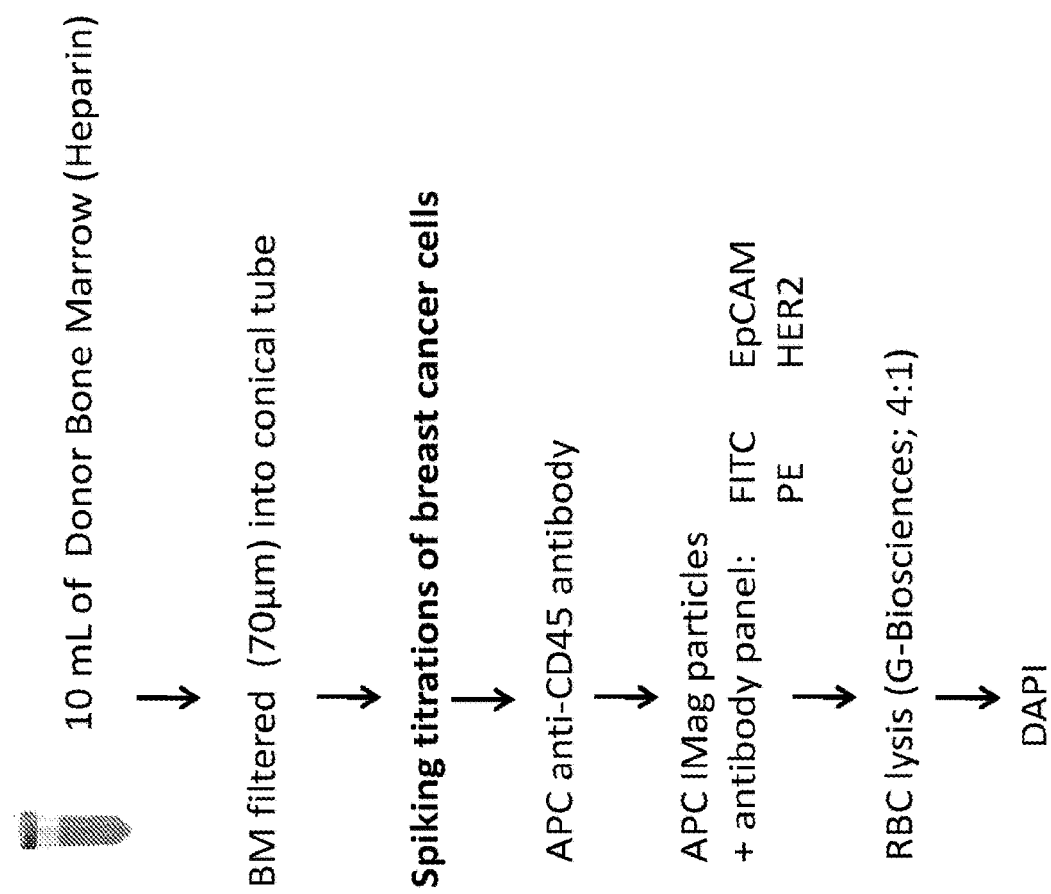

FIG. 20 depicts a flow diagram showing the staining workflow used for bone marrow spiking experiments.

Figure 21:
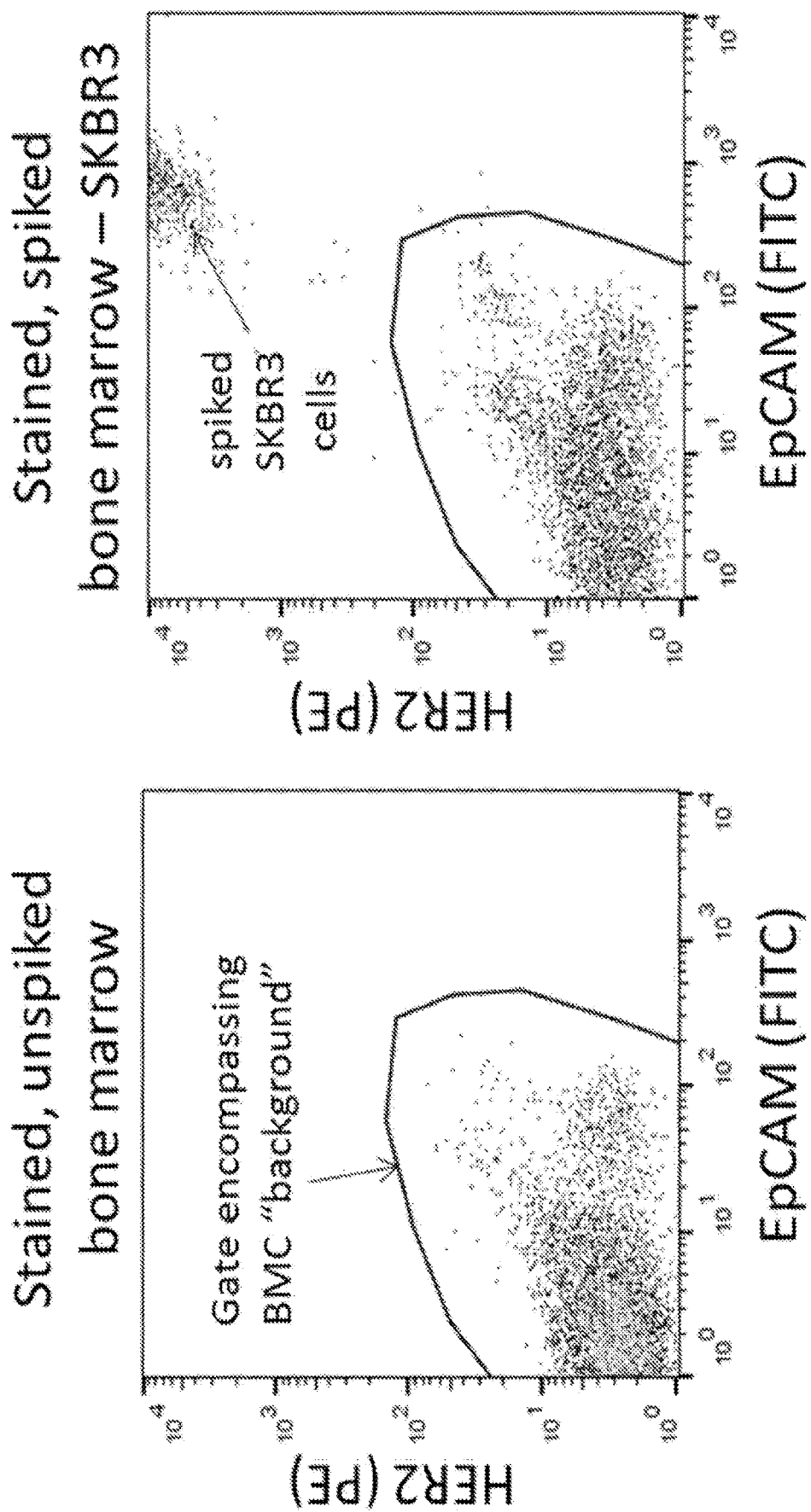
Figure 21:
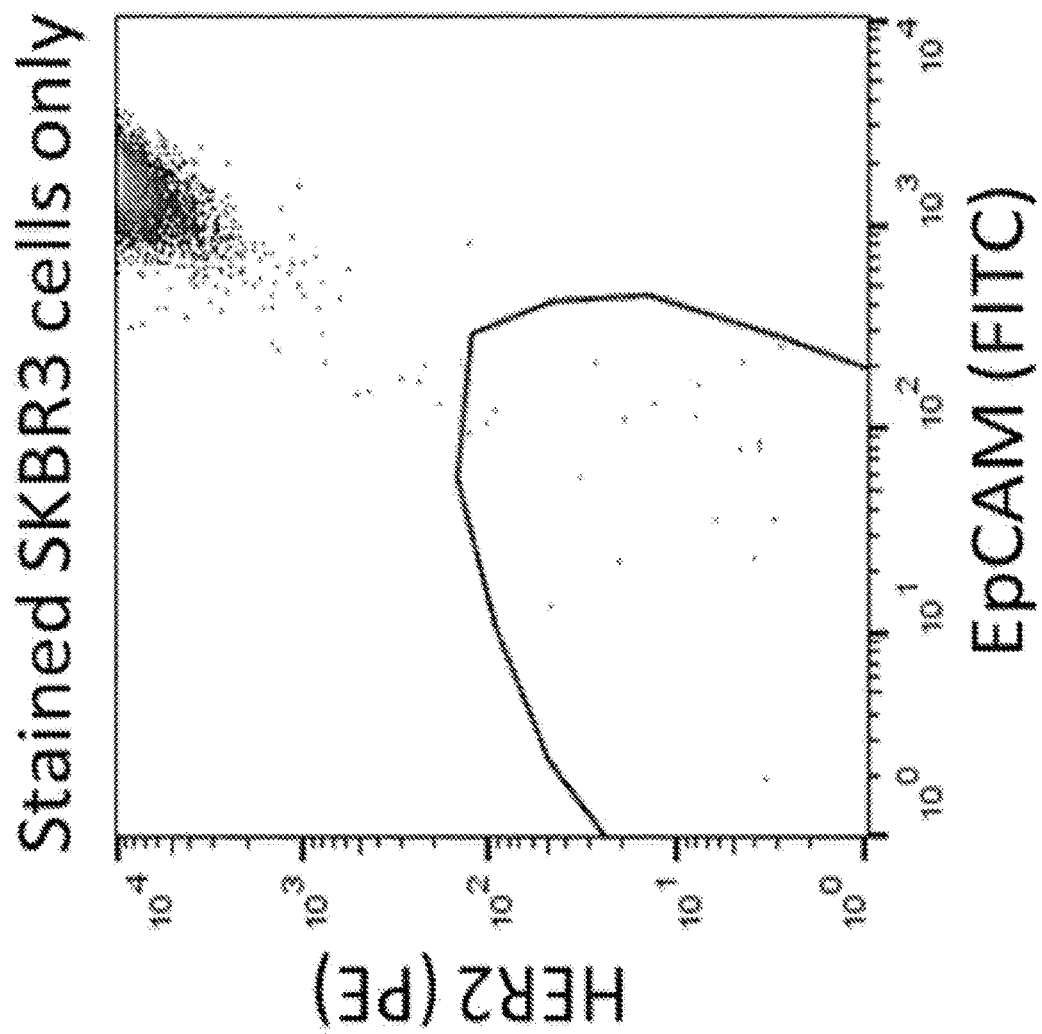

FIG. 21 depicts the results of exemplary experiments demonstrating detection of spiked 5000 SKBR3 human breast cancer cells (luminal, HER2-amplified) in donor bone marrow. HER2 vs. EpCAM dot plots include only DAPI-negative/CD45− negative events. A gate was drawn on dot plots of HER2 vs. EpCAM encompassing all DAPI-negative, CD45− negative bone marrow cells. Spiked tumor cells are identified as events which display outside of this gate (higher fluorescence intensity for EpCAM, HER2, or both markers).

Figure 22:
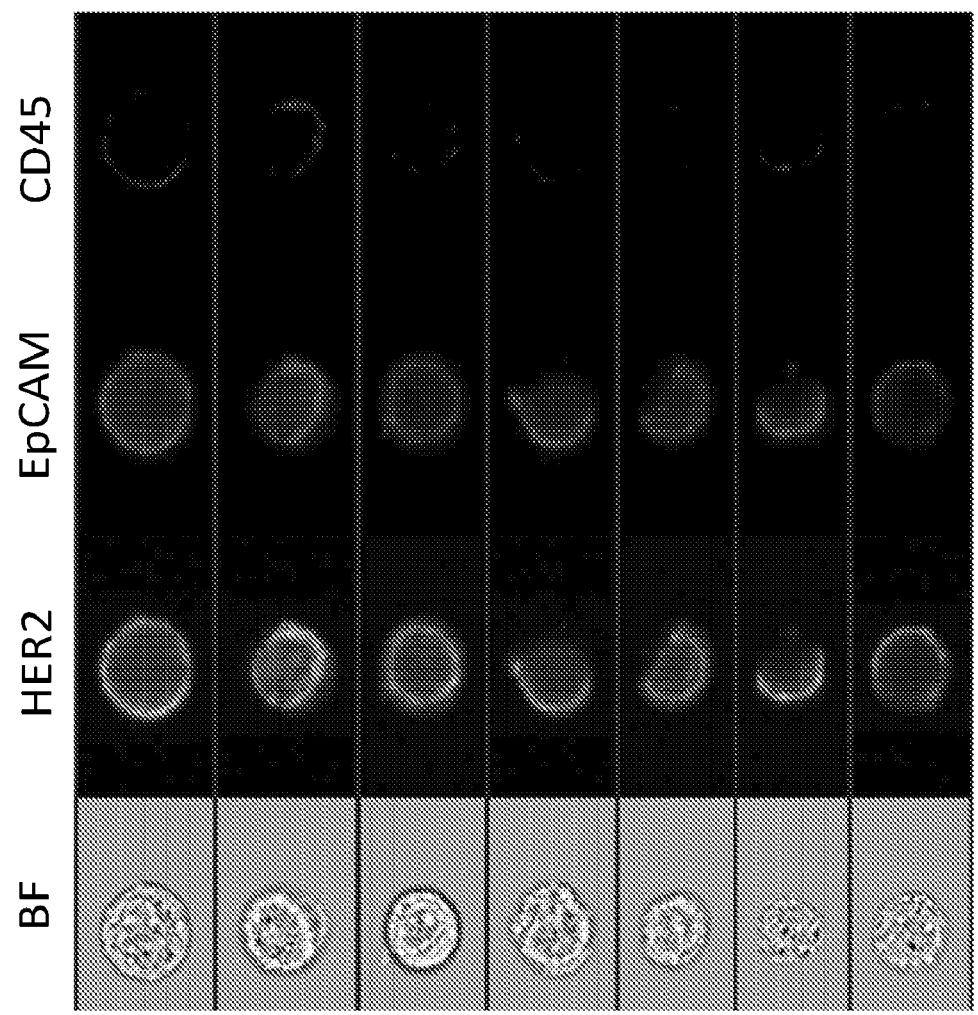

FIG. 22 depicts the results of exemplary experiments demonstrating detection of spiked MDA-MB-453 human breast cancer cells (luminal, HER2-amplified cell line) in donor bone marrow. Spiked tumor cells were identified and sorted as DAPI-negative, CD45− negative events with levels of HER2 and/or EpCAM above those found in unspiked bone marrow. The putative tumor cells sorted from spiked bone marrow samples were then analyzed using the ImageStream® imaging flow cytometer, which confirmed that the sorted cells were HER2-positive, EpCAM-positive, and CD45− negative. BF=Brightfield.

Figure 23:
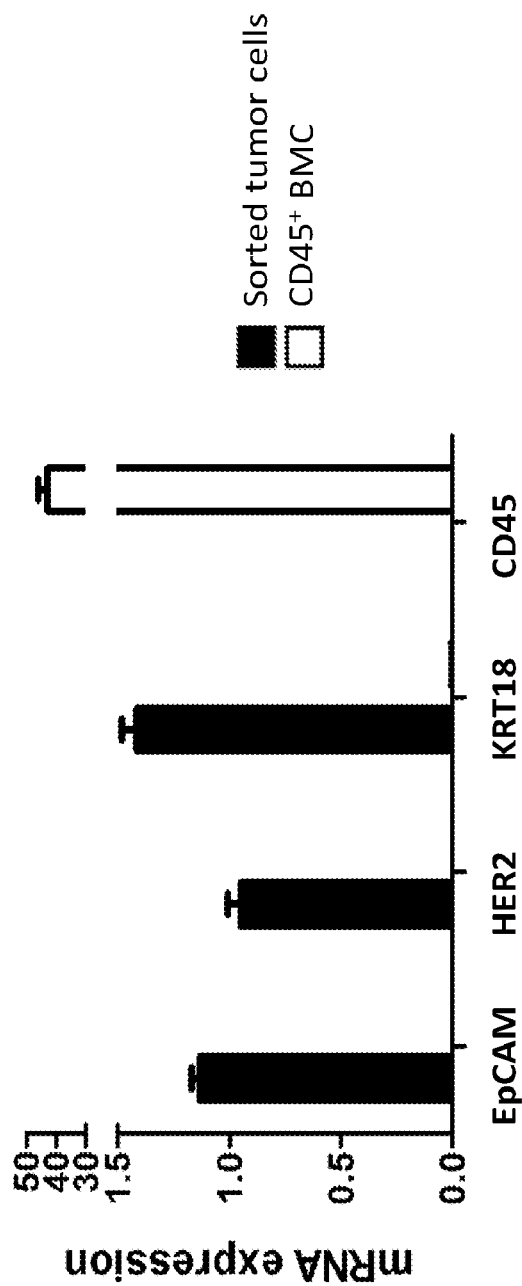

FIG. 23 depicts the results of exemplary experiments demonstrating qPCR analysis of sorted spiked tumor cells.

Figure 24:
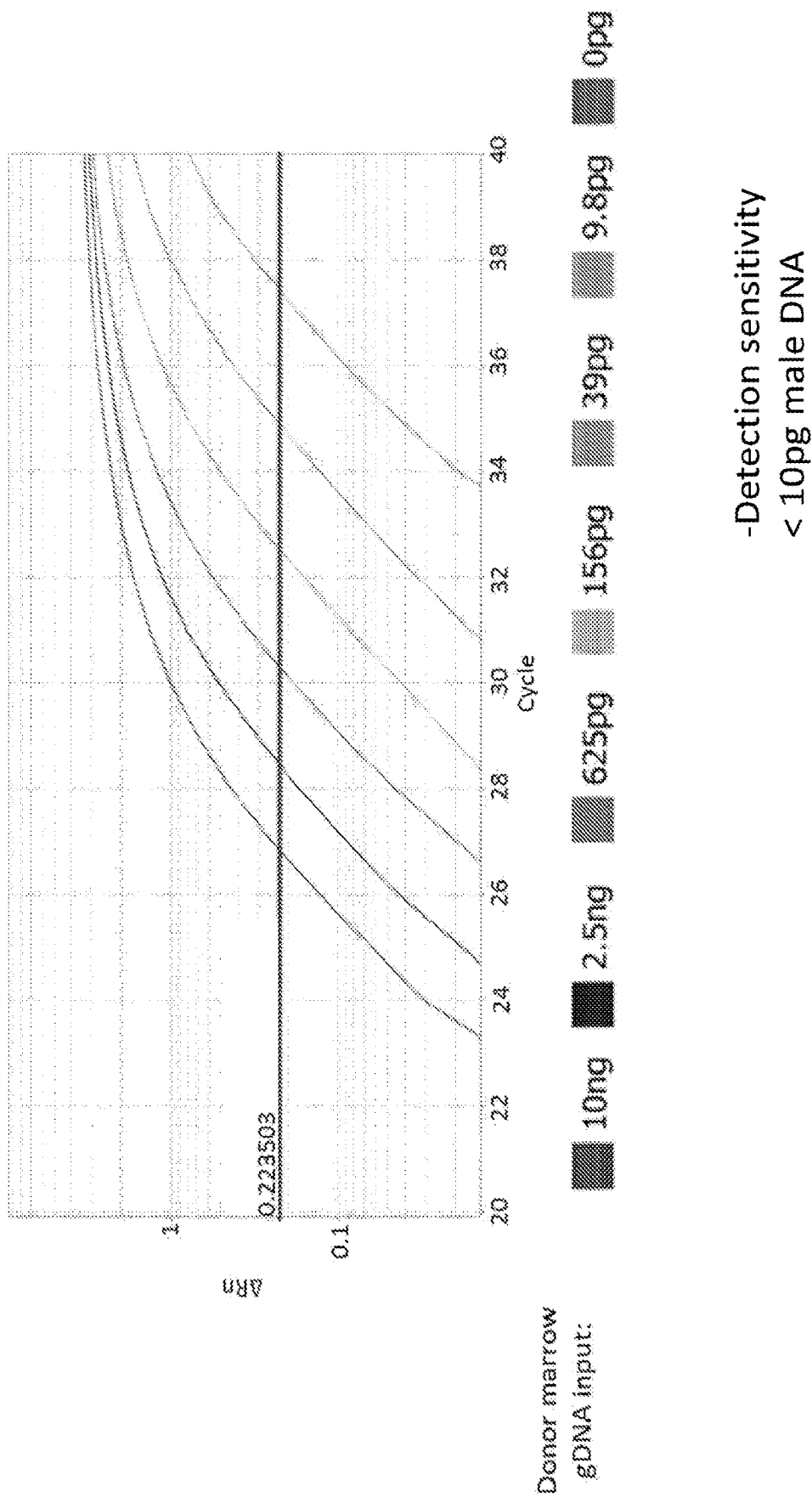
Figure 24:
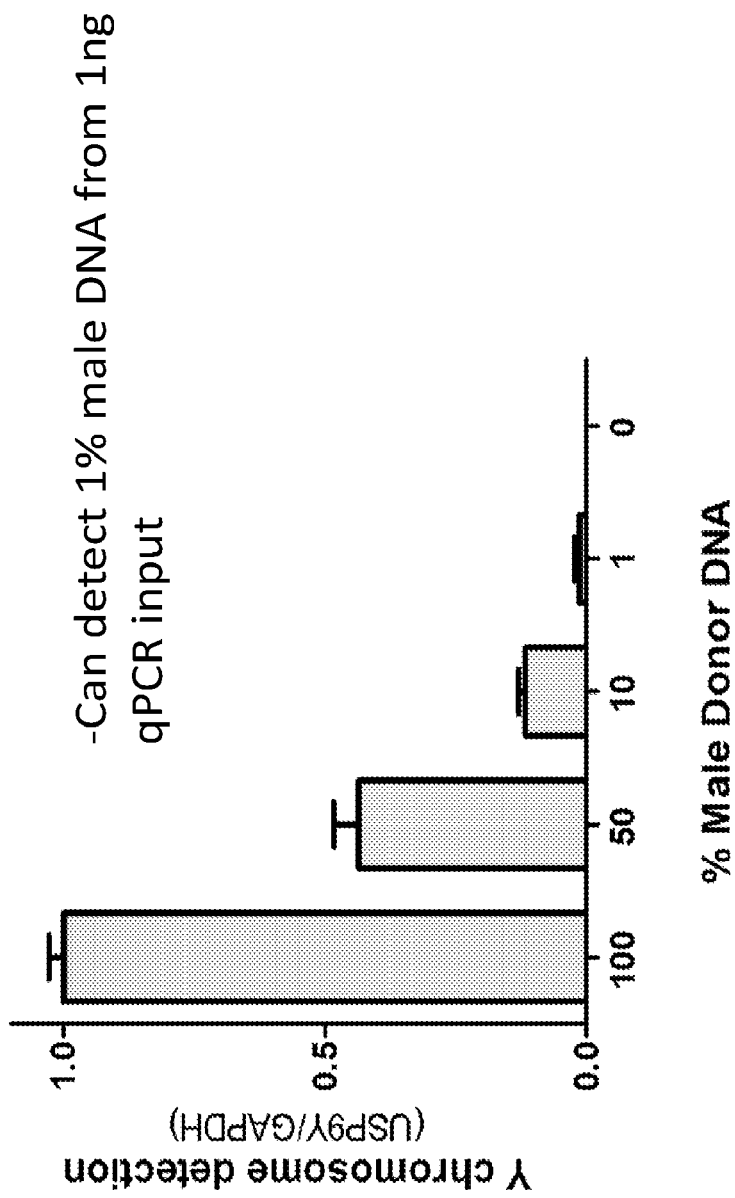

FIG. 24 depicts the results of exemplary experiments demonstrating an assessment of sorted tumor cell purity in spiking experiments for Y chromosome detection.

Figure 25:
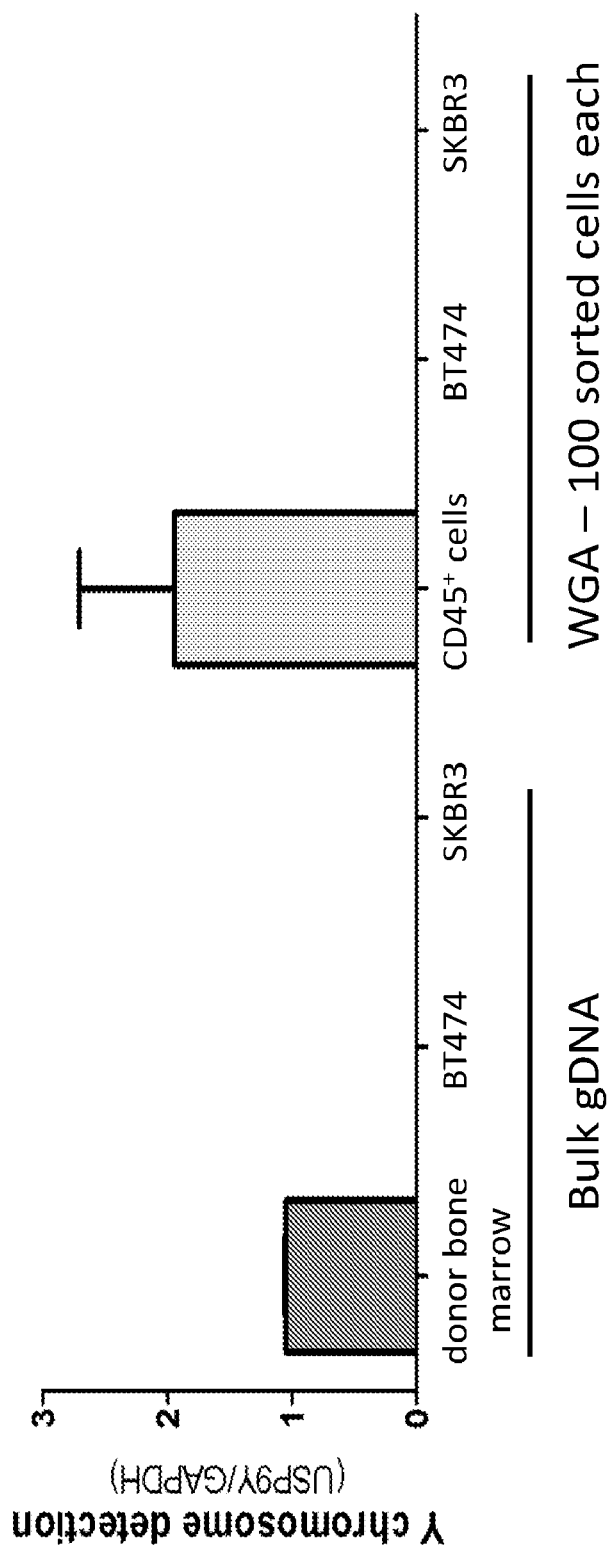

FIG. 25 depicts the results of exemplary experiments demonstrating an assessment of sorted DTC purity in spiking experiments for Y chromosome detection.

Figure 26:
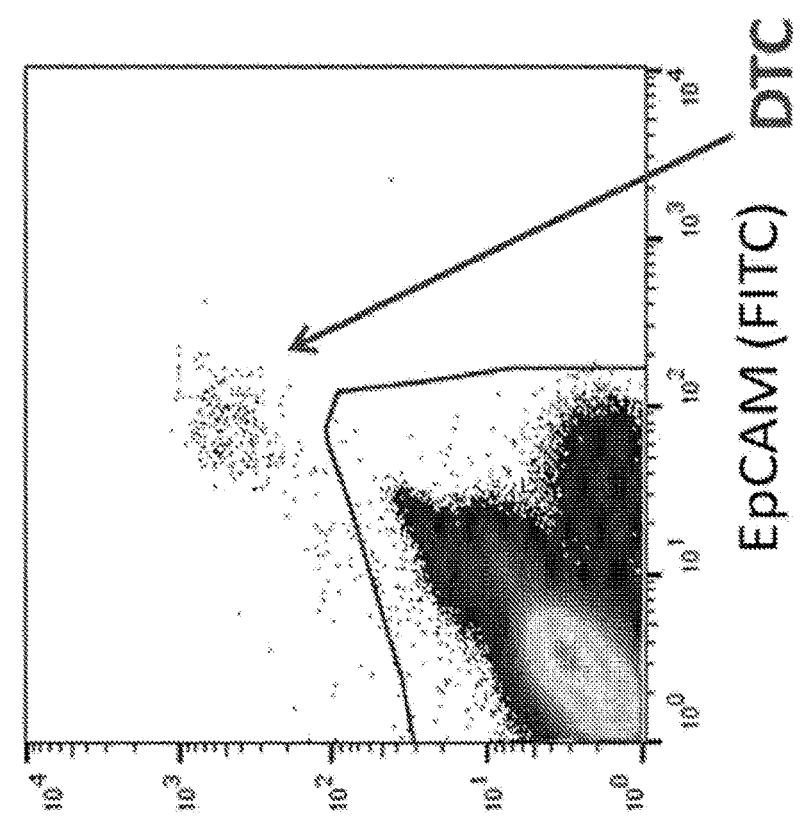
Figure 26:
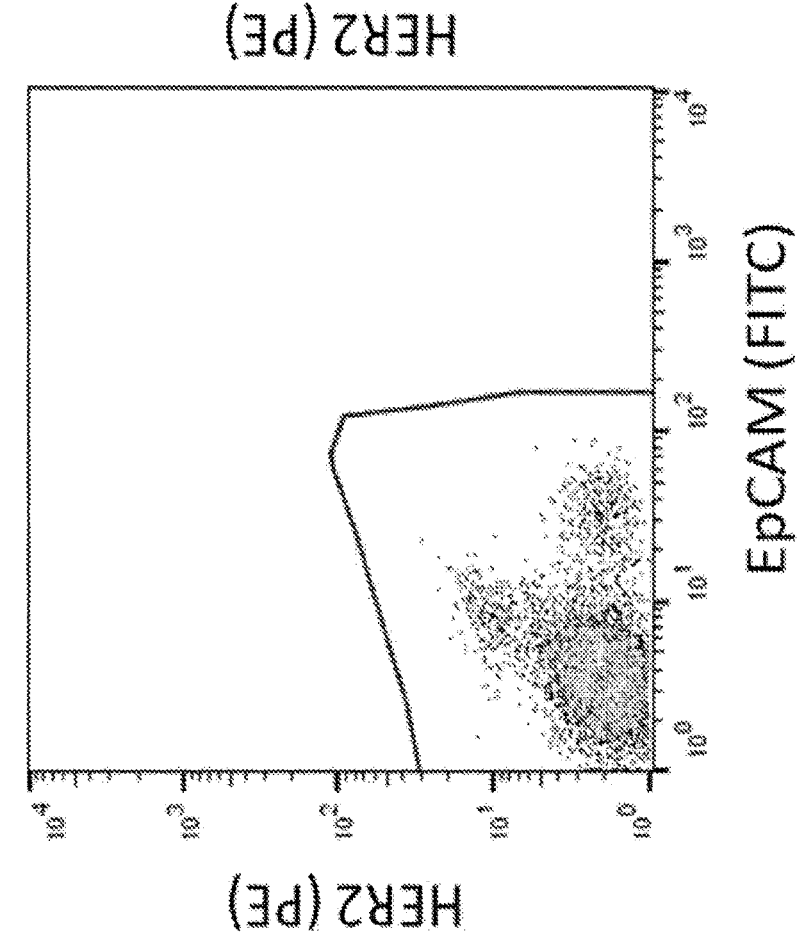

FIG. 26 depicts the results of exemplary experiments demonstrating detection of breast cancer DTCs in bone marrow aspirate from a patient with recurrent, metastatic disease.

Figure 27:
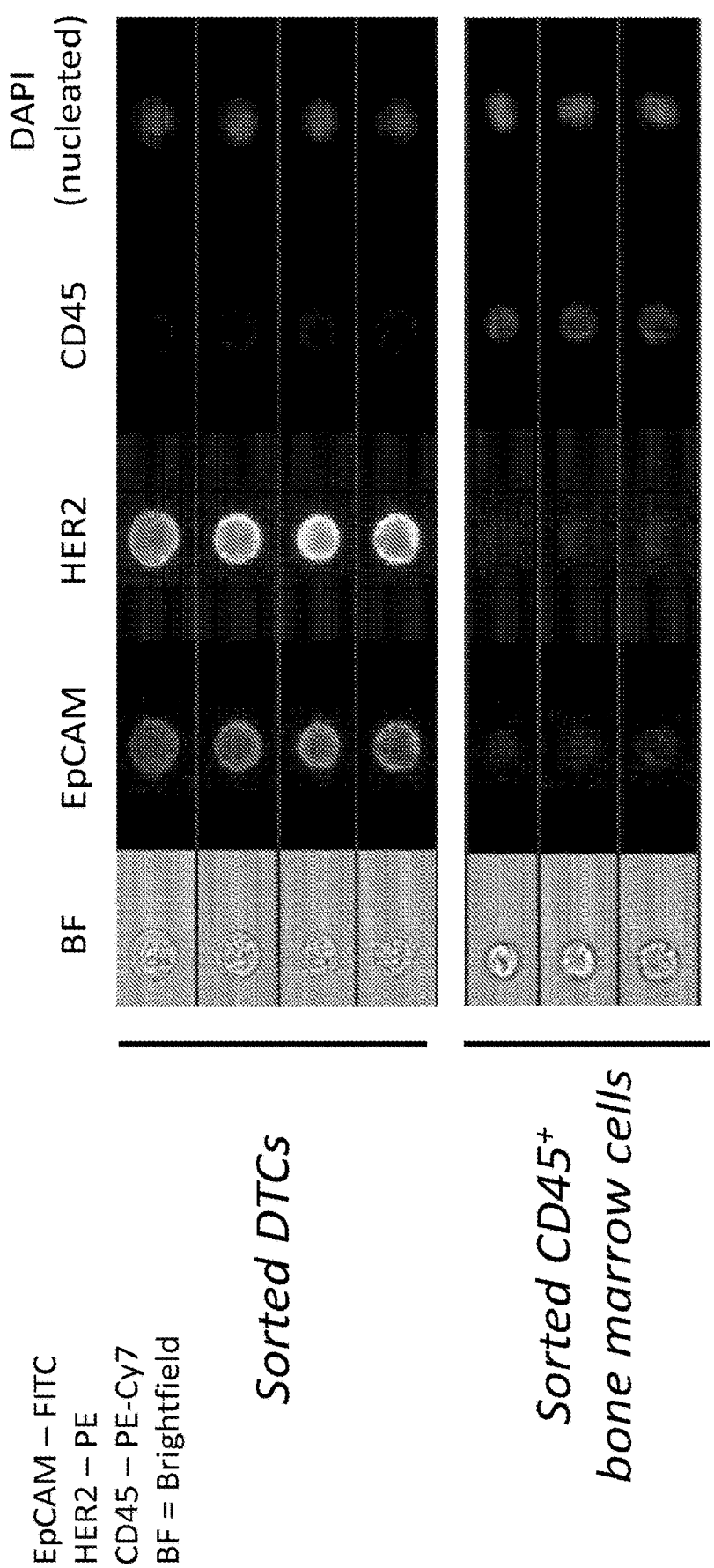

FIG. 27 depicts the results of exemplary experiments demonstrating an ImageStream® analysis confirming the tumor cell identity of sorted DTCs.

Figure 28:
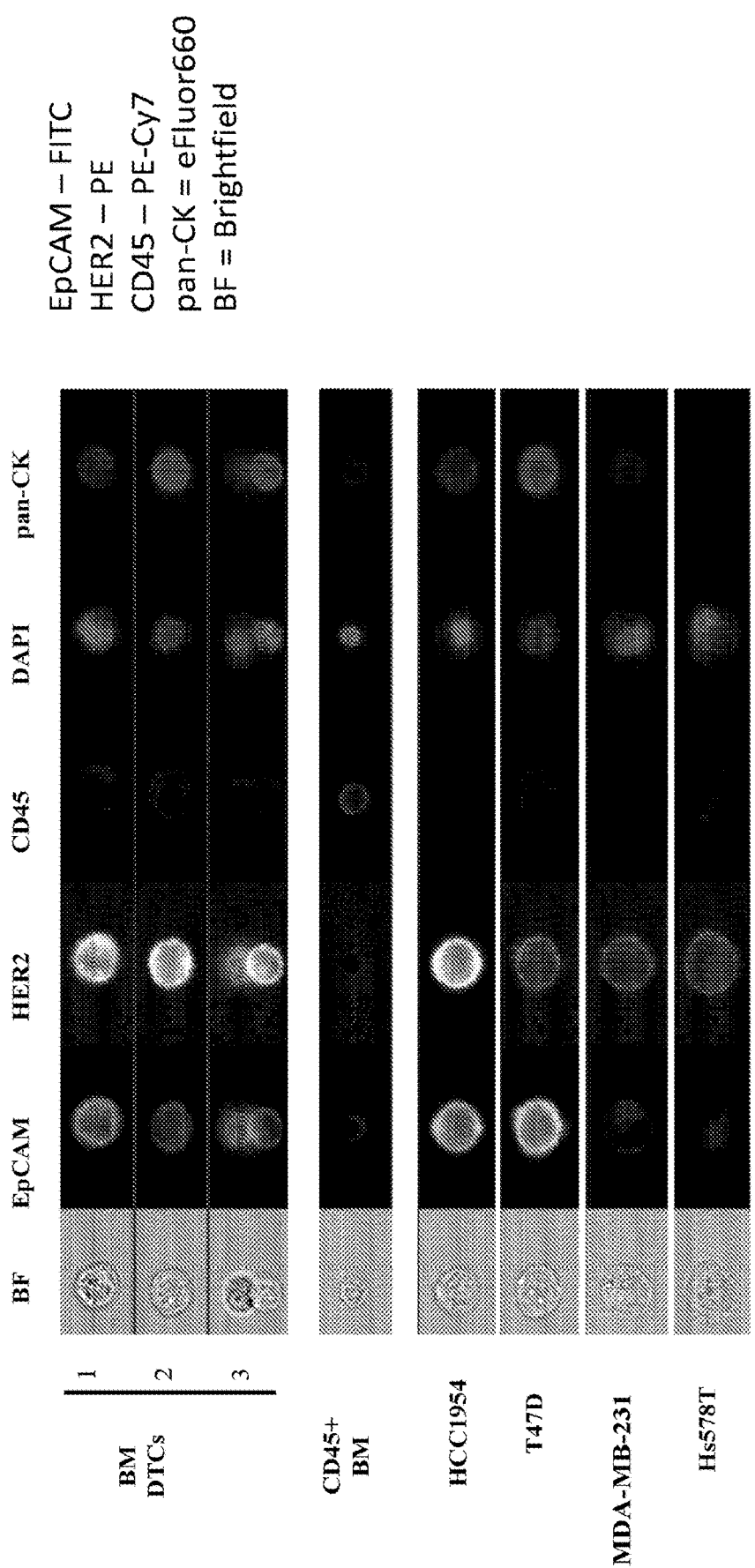

FIG. 28 depicts the results of exemplary experiments demonstrating an ImageStream® analysis confirming the cytokeratin expression of sorted breast cancer bone marrow DTCs.

Figure 29:
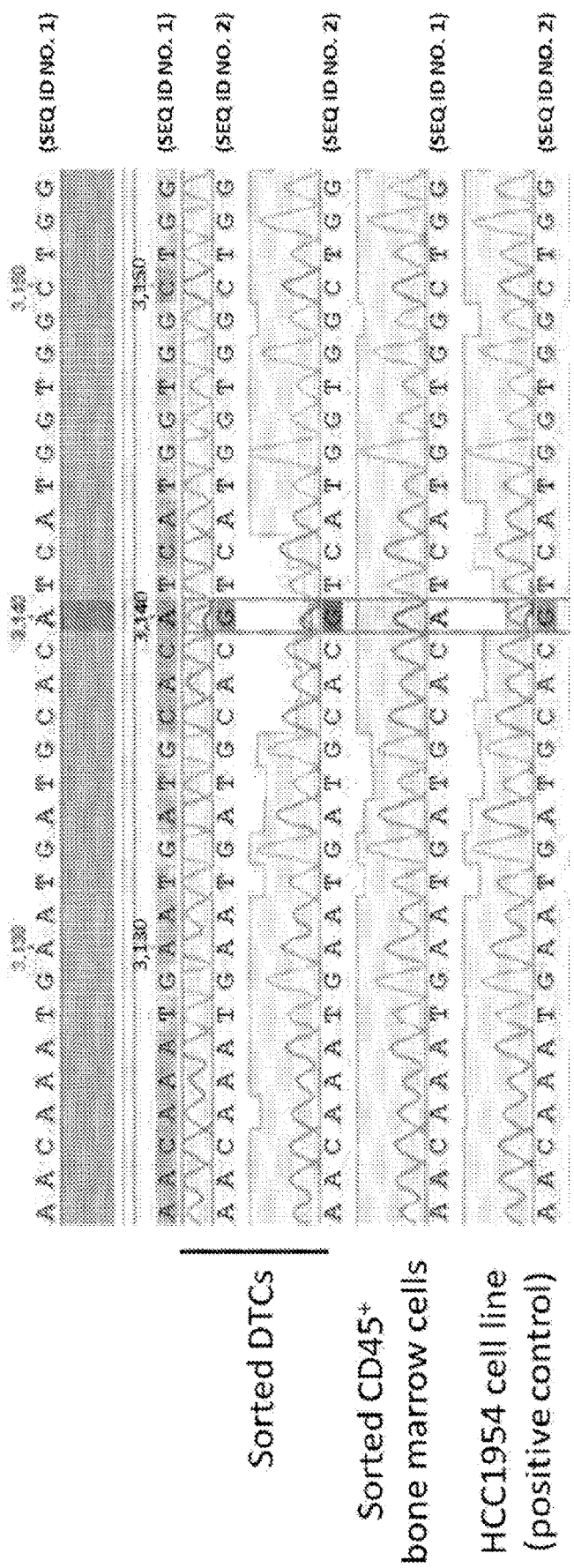

FIG. 29 depicts the results of exemplary experiments demonstrating a genomic analysis identifying a PIK3CA mutation in sorted DTCs.

Figure 30:
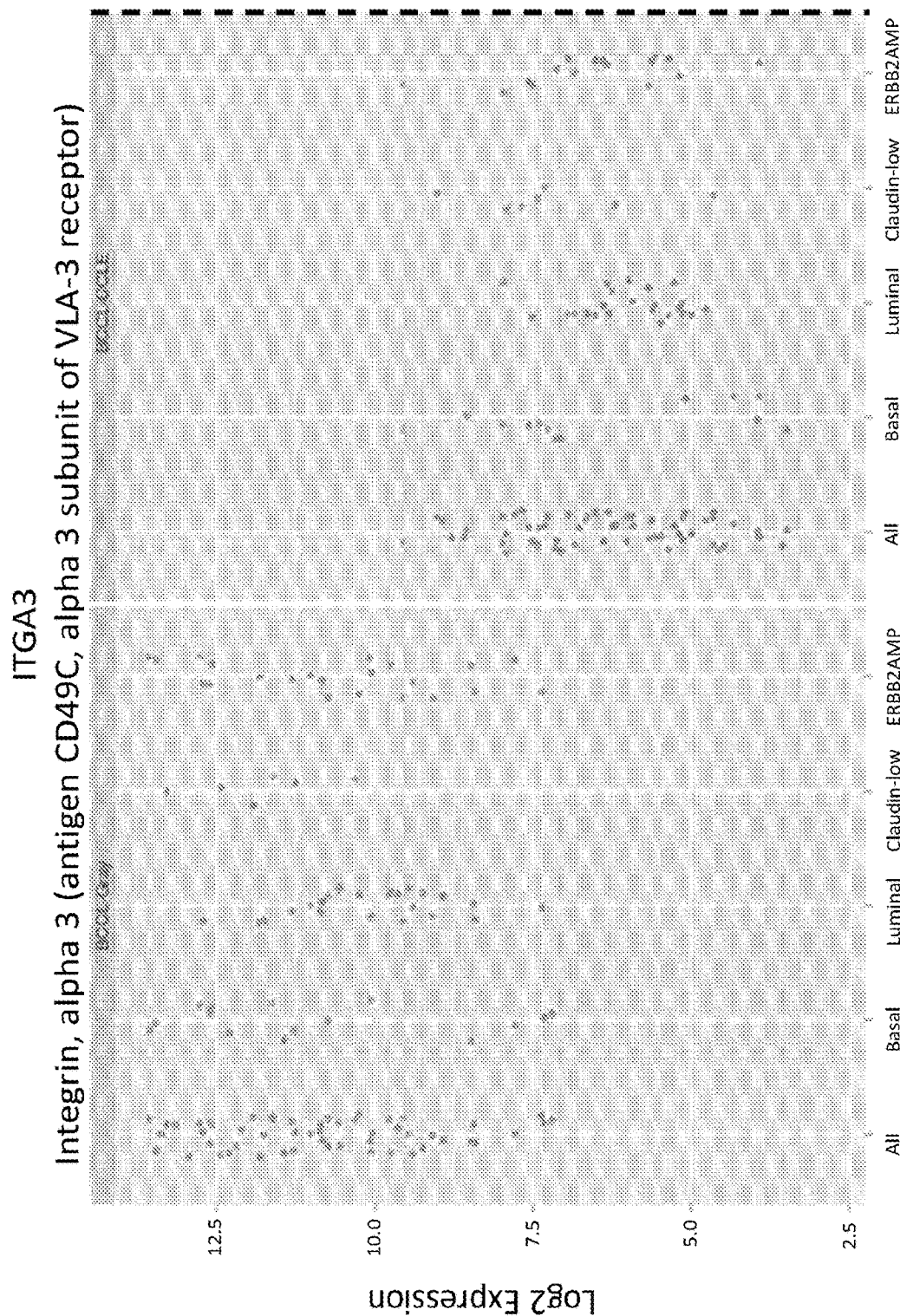
Figure 30:
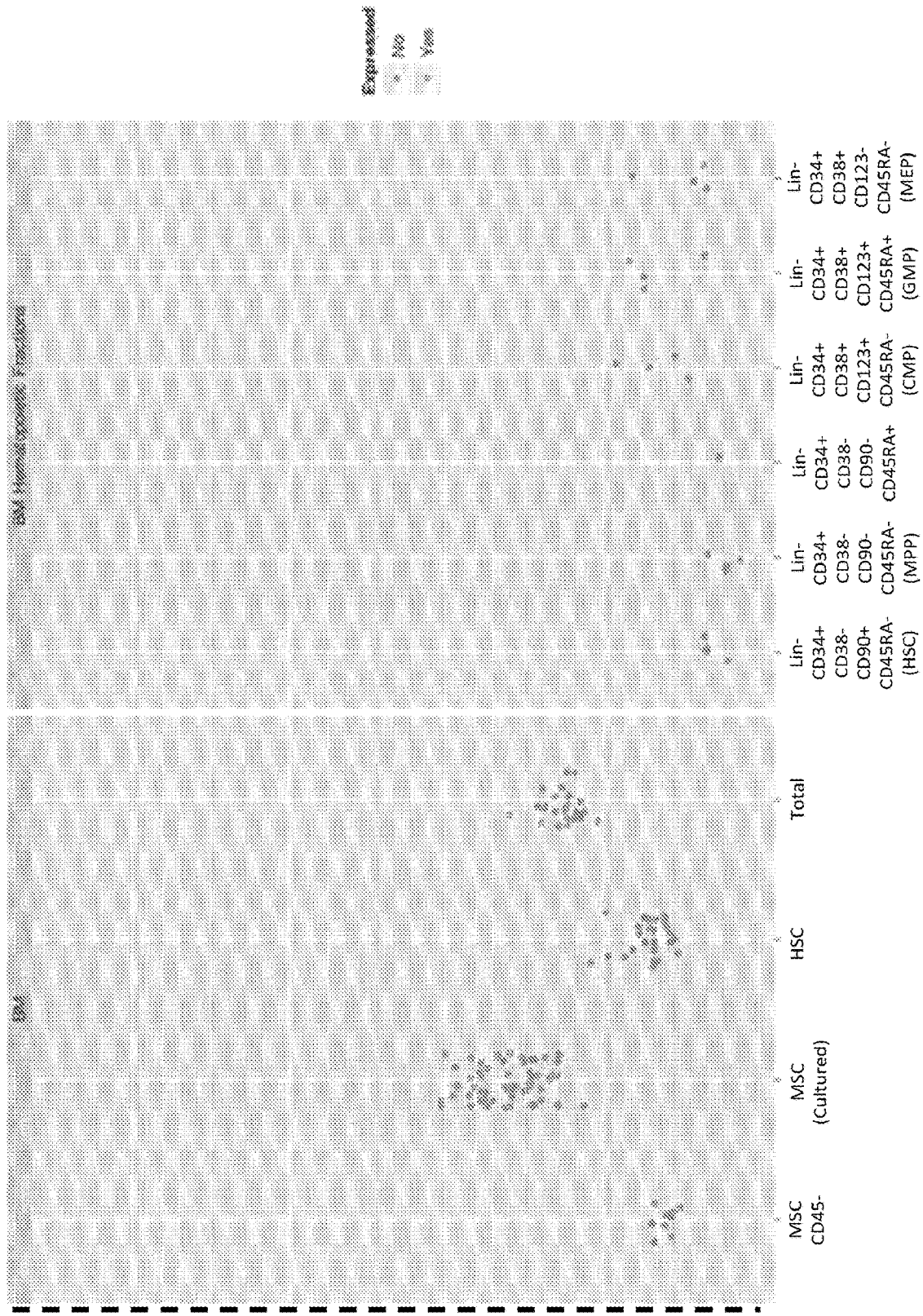

FIG. 30 depicts an analysis of the expression of CD49C across multiple breast cancer cell lines.

Figure 31:
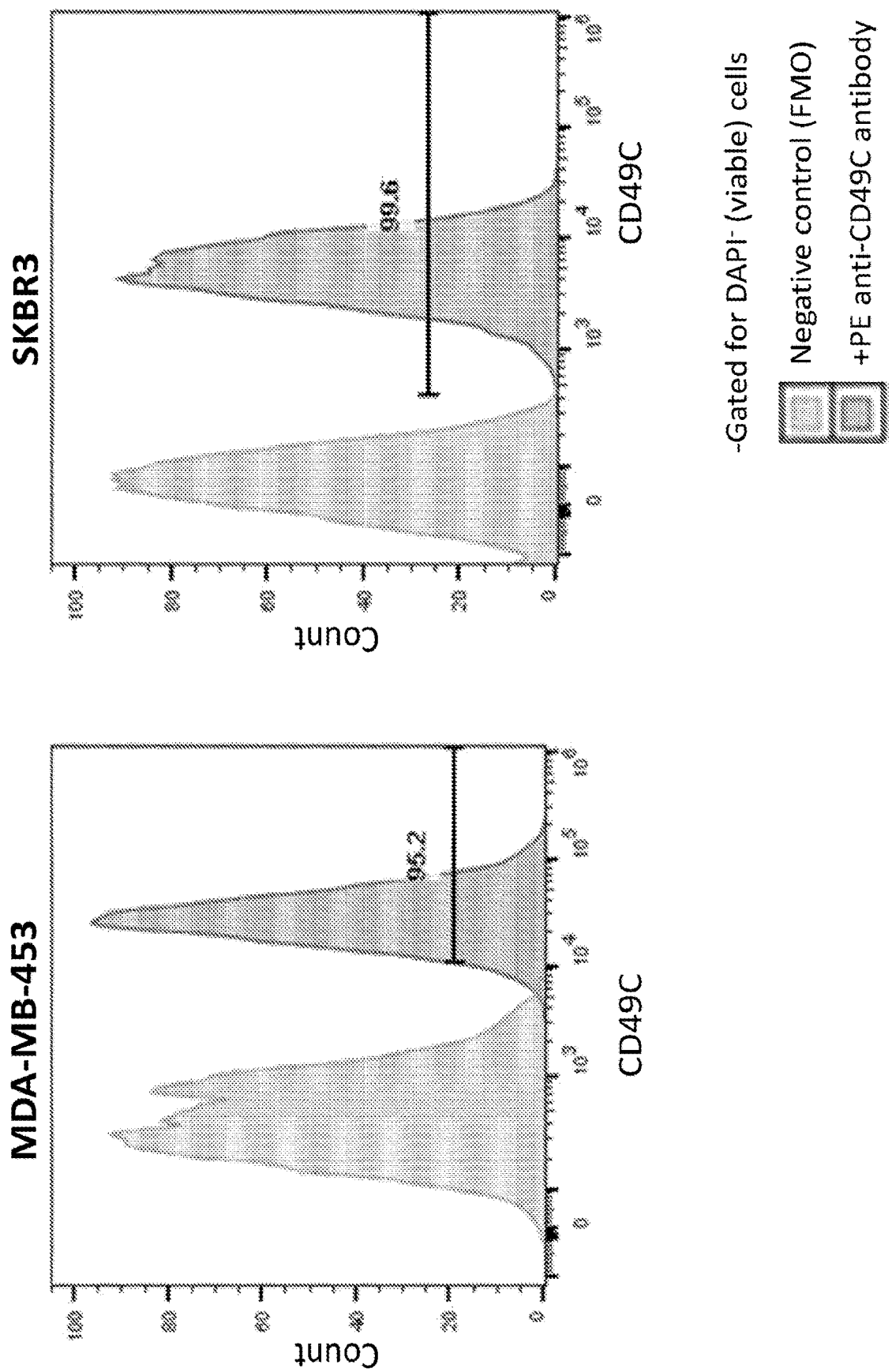

FIG. 31 depicts the results of exemplary experiments demonstrating CD49C labeling of luminal human breast cancer cell lines. BCC lines were stained with an anti-CD49C antibody conjugated to the fluorochrome PE. Histograms show PE-CD49C fluorescence intensity, as determined using an Attune NxT acoustic focusing flow cytometer (Gated for DAPI⁻ (viable) cells), compared to "fluorescence-minus-one" (FMO) negative controls, in which the PE anti-CD49C antibody was omitted from the staining reaction. Data analysis was performed using FlowJo analysis software.

Figure 32:
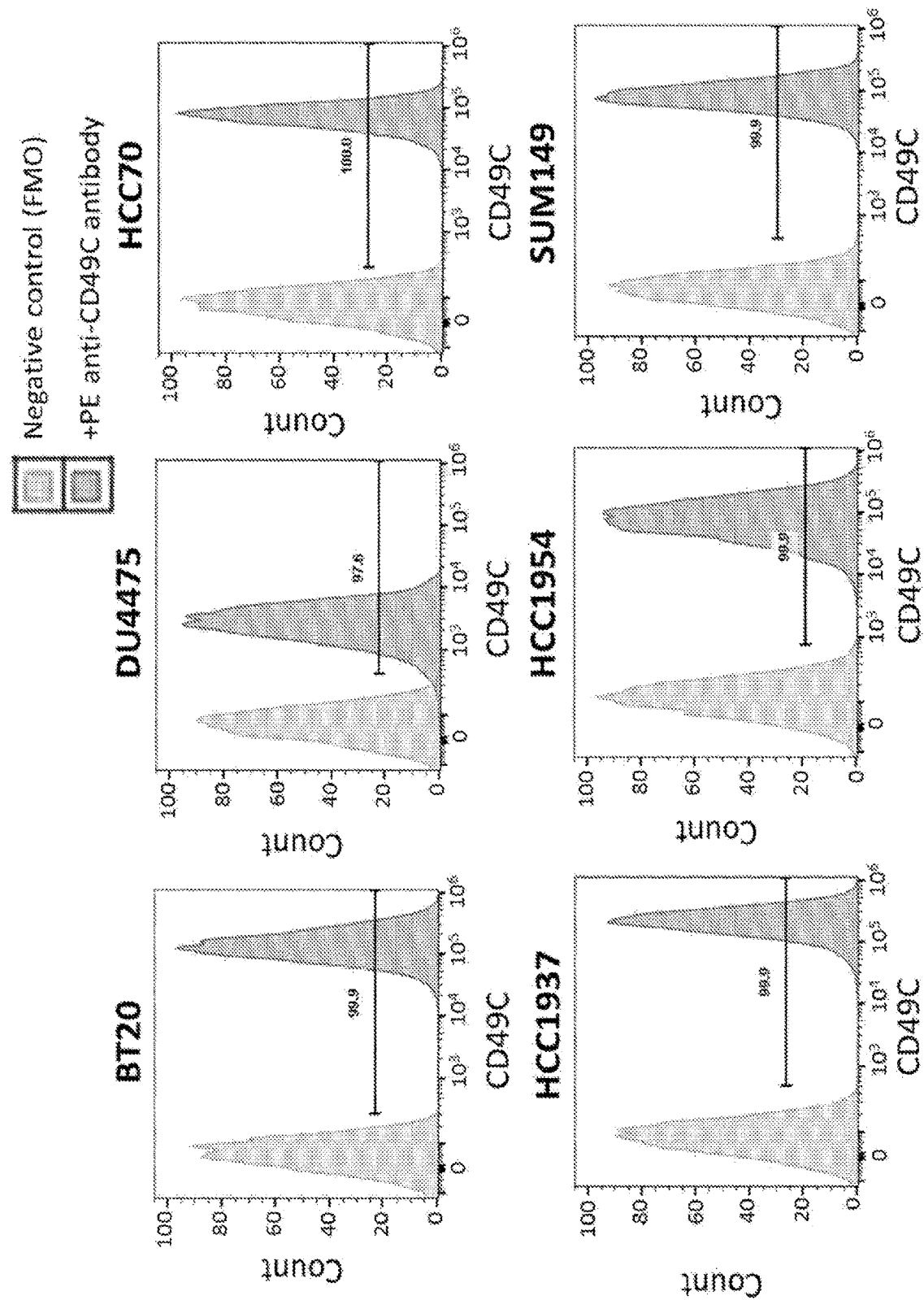

FIG. 32 depicts the results of exemplary experiments demonstrating CD49C labeling of basal human breast cancer cell lines. BCC lines were stained with an anti-CD49C antibody conjugated to the fluorochrome PE. Histograms show PE-CD49C fluorescence intensity, as determined using an Attune NxT acoustic focusing flow cytometer (Gated for DAPI⁻ (viable) cells), compared to "fluorescence-minus-one" (FMO) negative controls, in which the PE anti-CD49C antibody was omitted from the staining reaction. Data analysis was performed using FlowJo analysis software.

Figure 33:
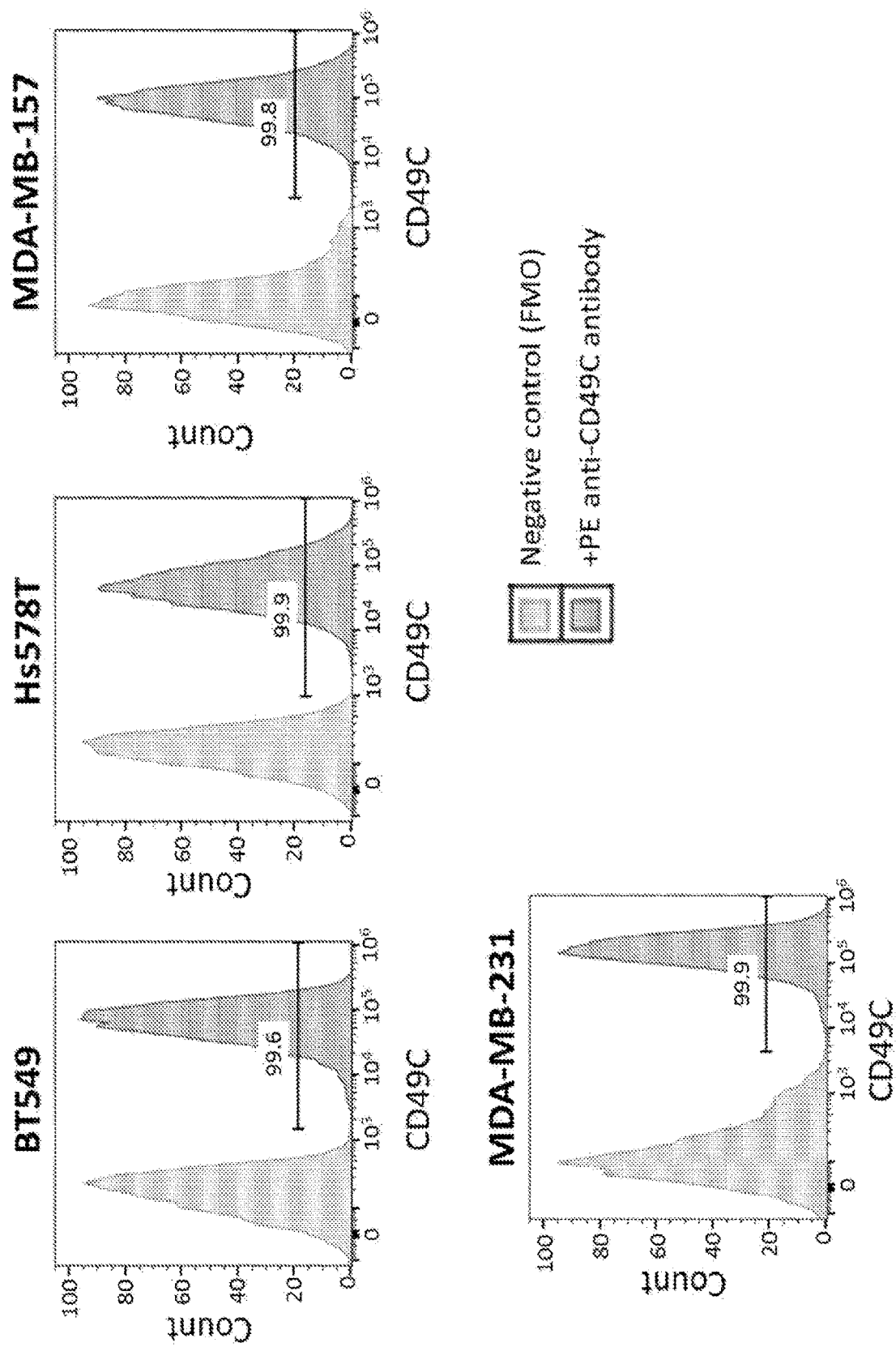

FIG. 33 depicts the results of exemplary experiments demonstrating CD49C labeling of claudin-low human breast cancer cell lines. BCC lines were stained with an anti-CD49C antibody conjugated to the fluorochrome PE. Histograms show PE-CD49C fluorescence intensity, as determined using an Attune NxT acoustic focusing flow cytometer (Gated for DAPI⁻ (viable) cells), compared to "fluorescence-minus-one" (FMO) negative controls, in which the PE anti-CD49C antibody was omitted from the staining reaction. Data analysis was performed using FlowJo analysis software.

Figure 34:
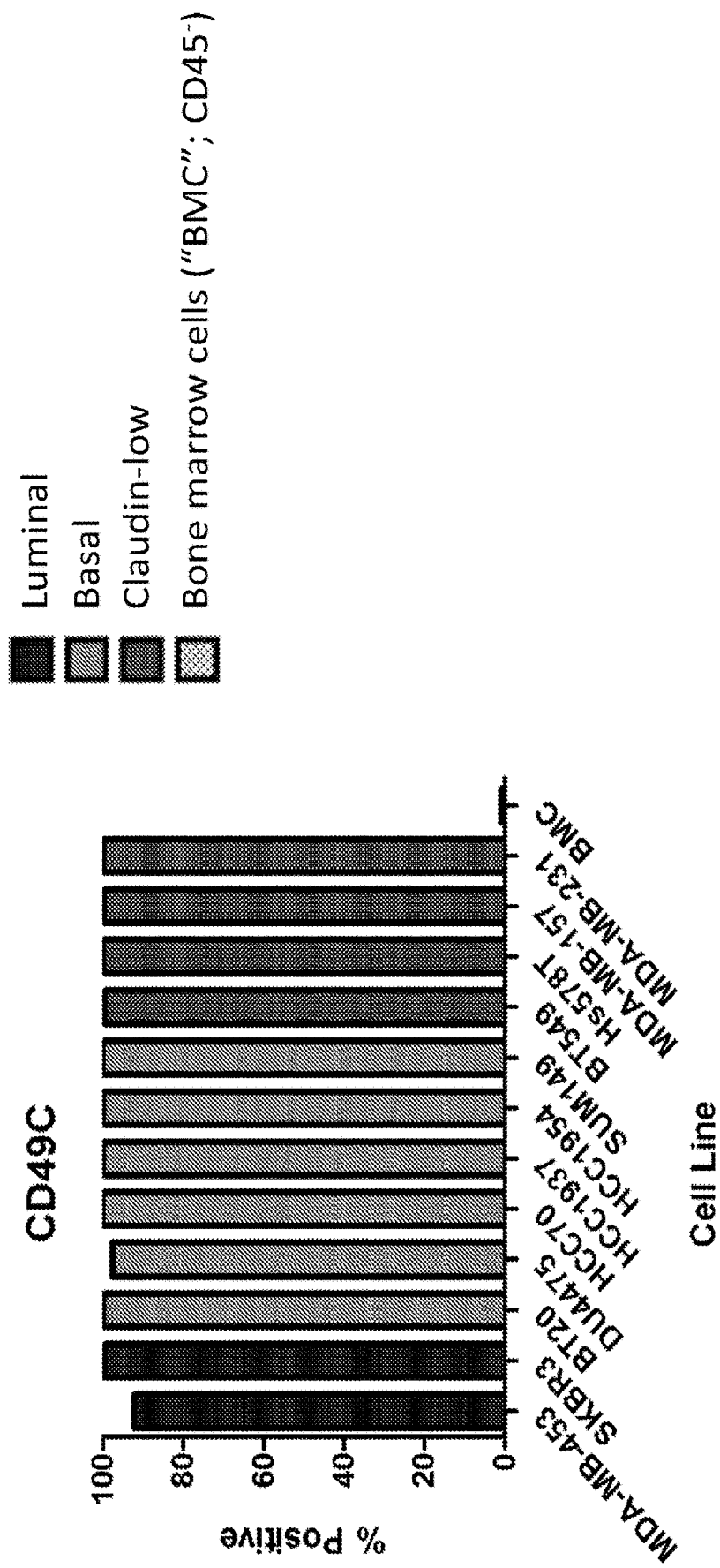

FIG. 34 depicts a summary of the results of exemplary experiments presented in FIG. 31 through FIG. 33 demonstrating the percentage of positive CD49C labeling of human breast cancer cell lines.

Figure 35:
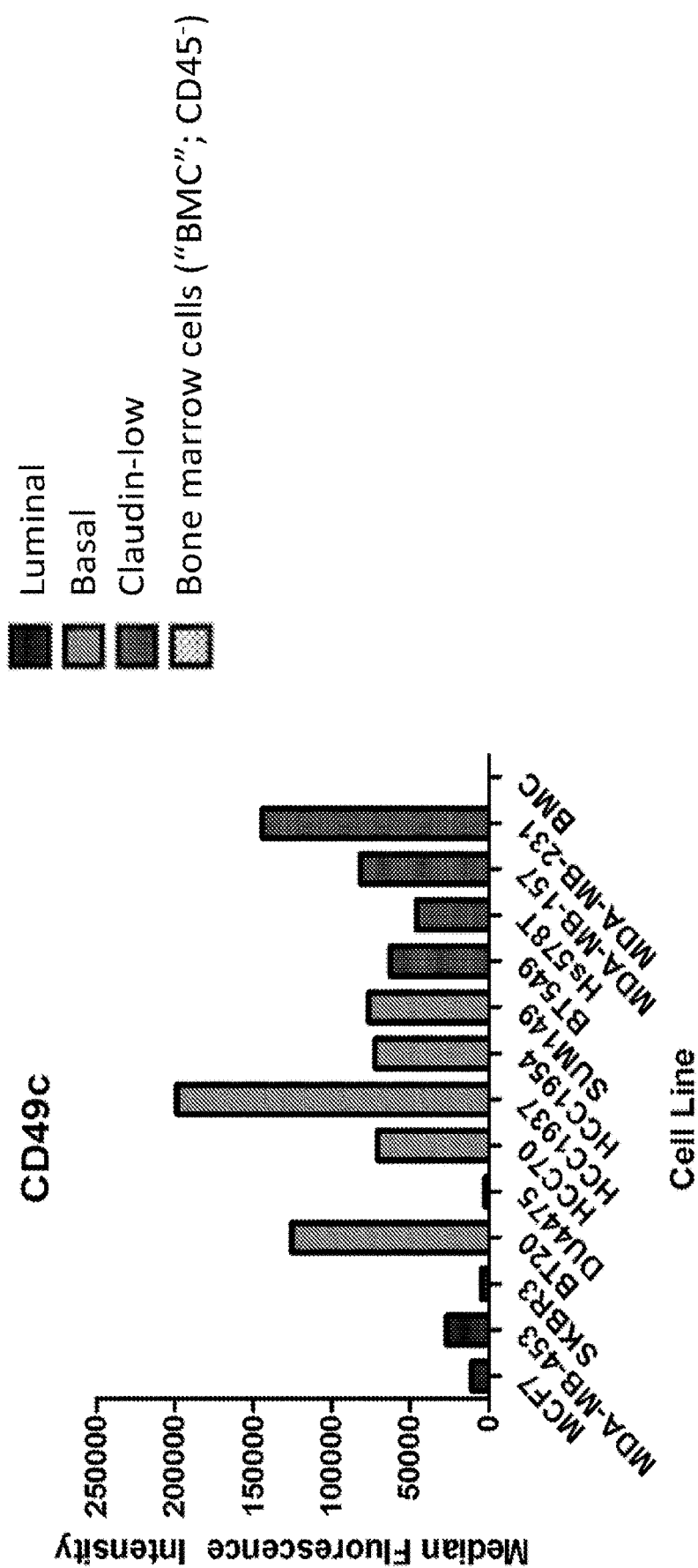

FIG. 35 depicts a summary of the results of exemplary experiments presented in FIG. 31 through FIG. 33 demonstrating the median fluorescence intensity of CD49C labeled cells for different human breast cancer cell lines.

Figure 36:
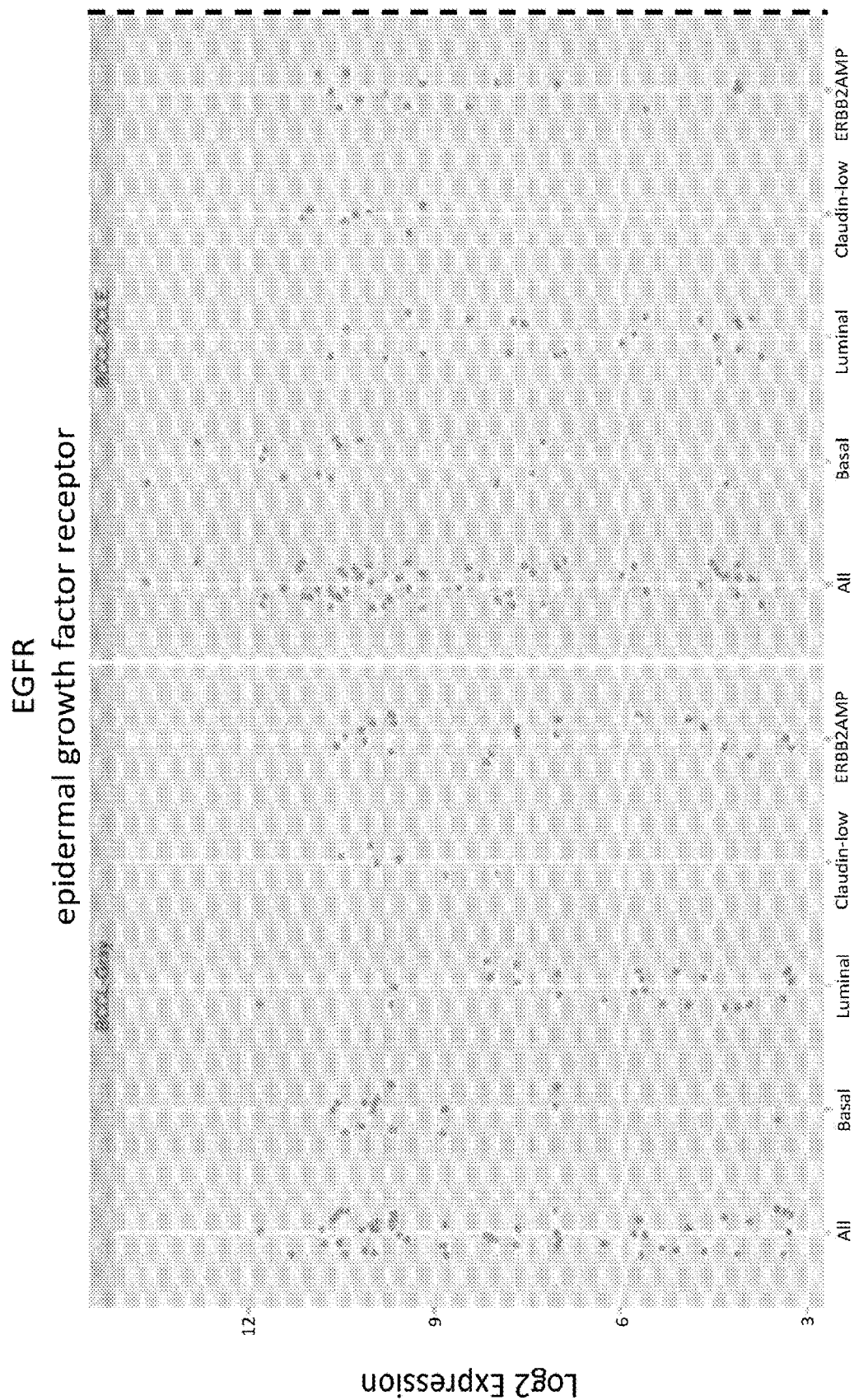
Figure 36:
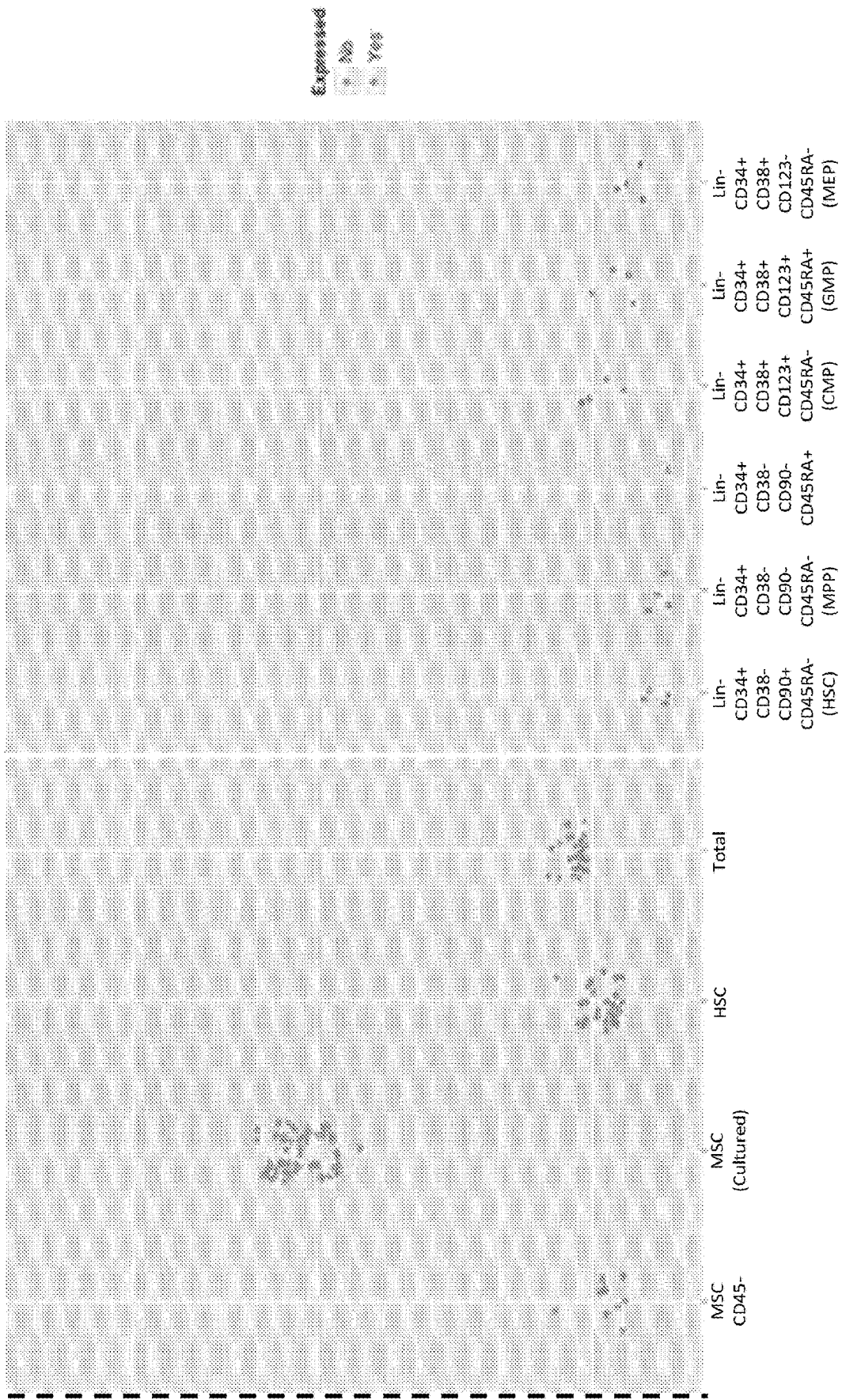

FIG. 36 depicts an analysis of the expression of EGFR across multiple breast cancer cell lines.

Figure 37:
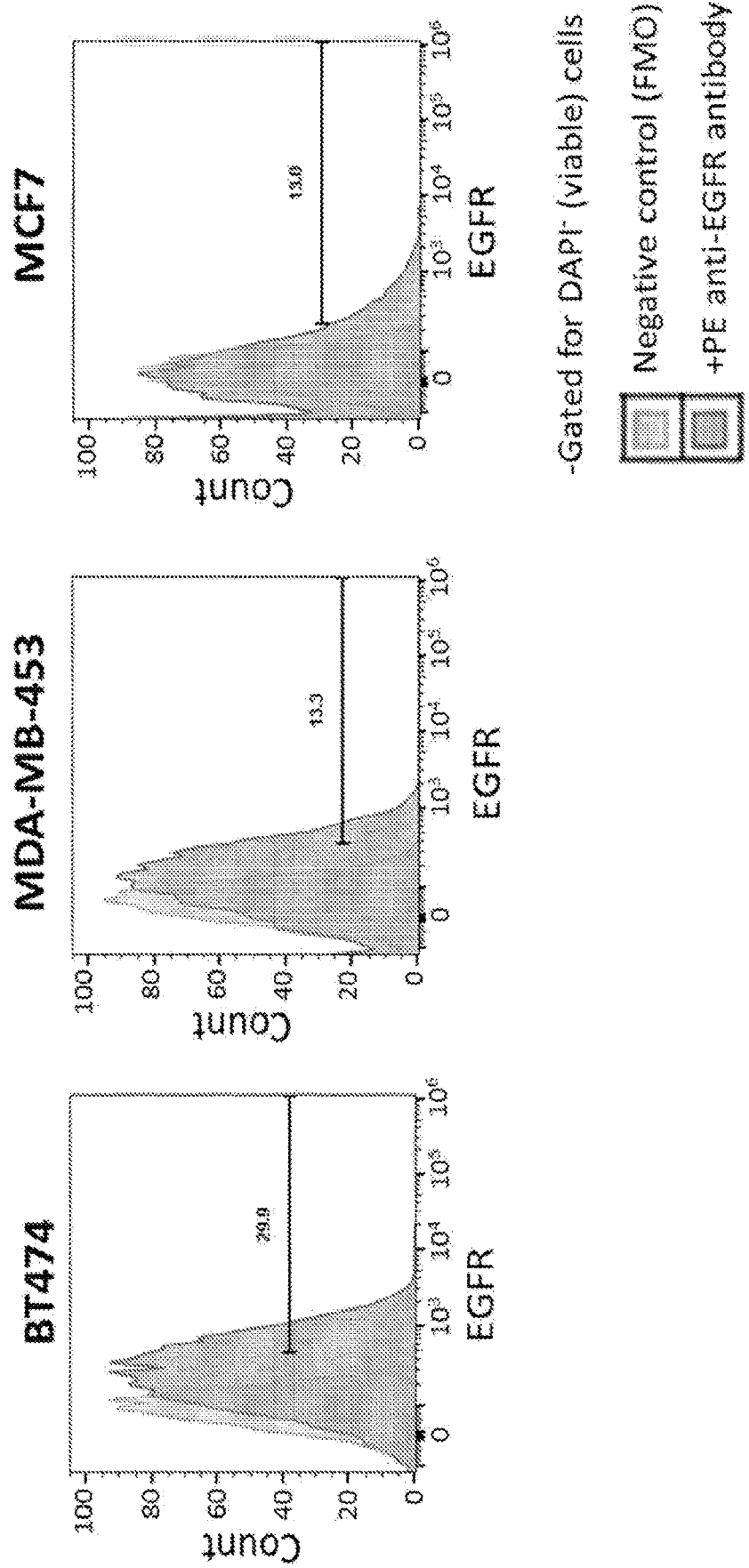

FIG. 37 depicts the results of exemplary experiments demonstrating EGFR labeling of luminal human breast cancer cell lines. BCC lines were stained with an anti-EGFR antibody conjugated to the fluorochrome PE. Histograms show PE-EGFR fluorescence intensity, as determined using an Attune NxT acoustic focusing flow cytometer (Gated for DAPI⁻ (viable) cells), compared to "fluorescence-minus-one" (FMO) negative controls, in which the PE anti-EGFR antibody was omitted from the staining reaction. Data analysis was performed using FlowJo analysis software.

Figure 38:
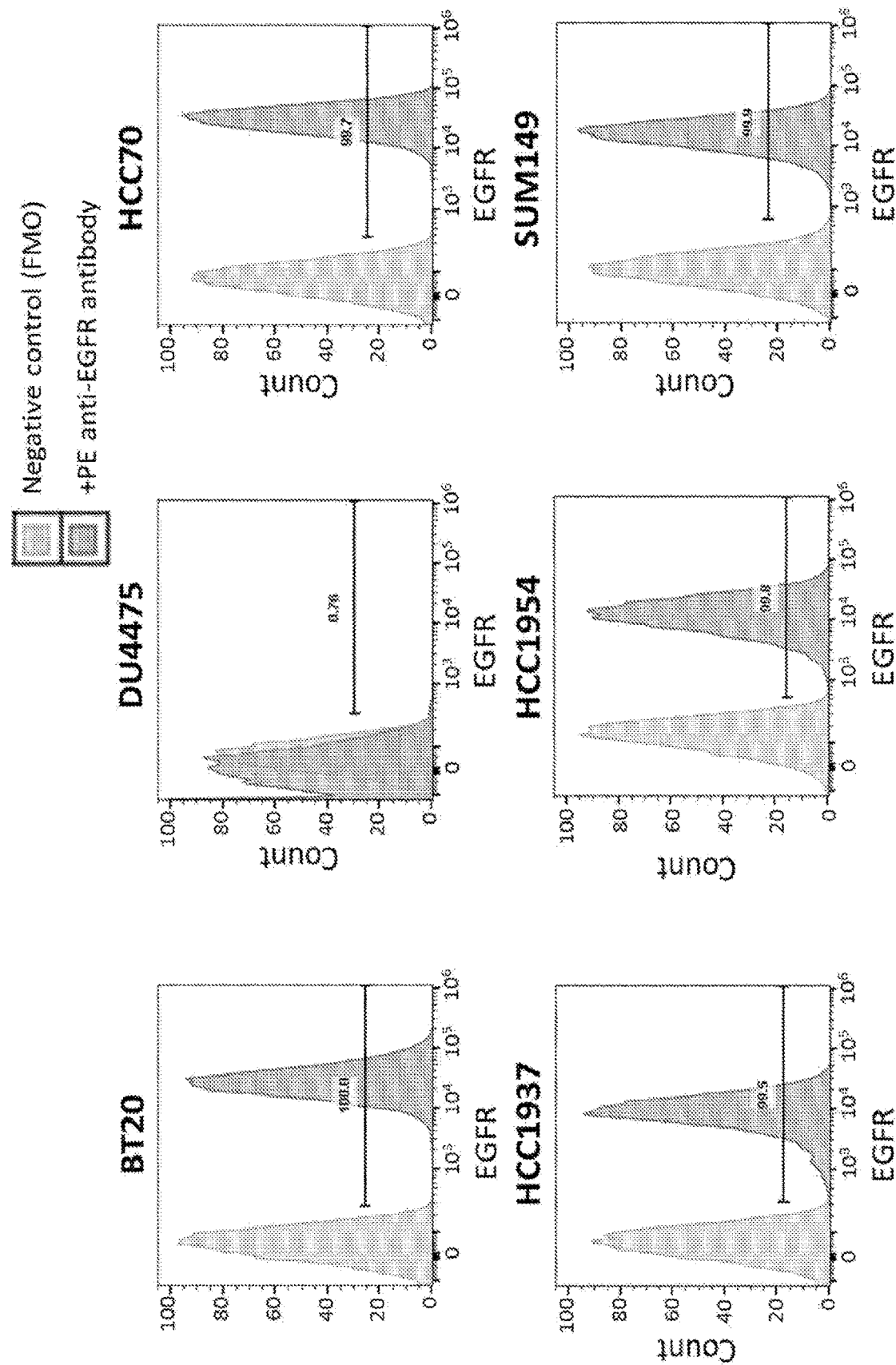

FIG. 38 depicts the results of exemplary experiments demonstrating EGFR labeling of basal human breast cancer cell lines. BCC lines were stained with an anti-EGFR antibody conjugated to the fluorochrome PE. Histograms show PE-EGFR fluorescence intensity, as determined using an Attune NxT acoustic focusing flow cytometer (Gated for DAPI⁻ (viable) cells), compared to "fluorescence-minus-one" (FMO) negative controls, in which the PE anti-EGFR antibody was omitted from the staining reaction. Data analysis was performed using FlowJo analysis software.

Figure 39:
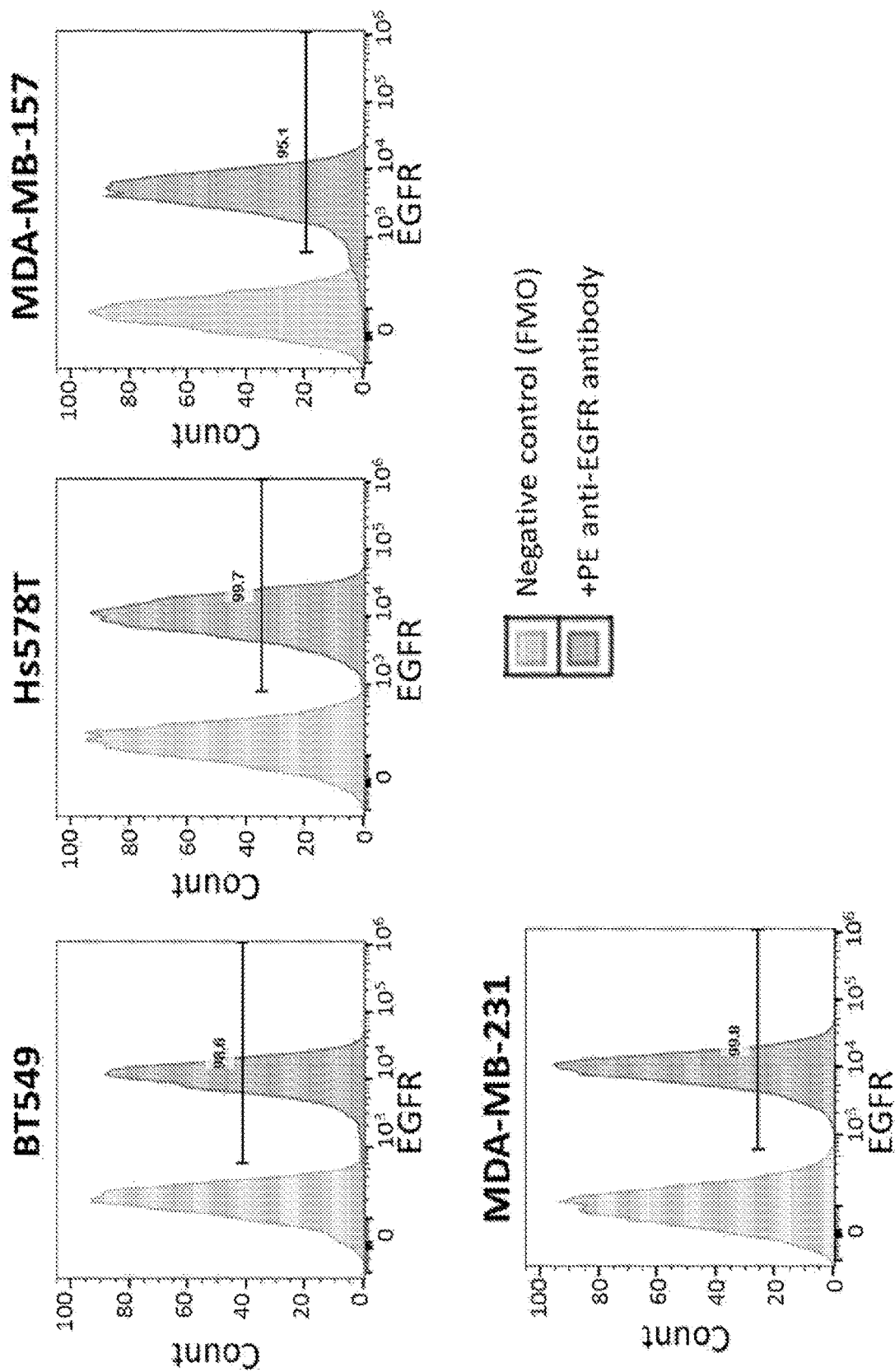

FIG. 39 depicts the results of exemplary experiments demonstrating EGFR labeling of claudin-low human breast cancer cell lines. BCC lines were stained with an anti-EGFR antibody conjugated to the fluorochrome PE. Histograms show PE-EGFR fluorescence intensity, as determined using an Attune NxT acoustic focusing flow cytometer (Gated for DAPI⁻ (viable) cells), compared to "fluorescence-minus-one" (FMO) negative controls, in which the PE anti-EGFR antibody was omitted from the staining reaction. Data analysis was performed using FlowJo analysis software.

Figure 40:
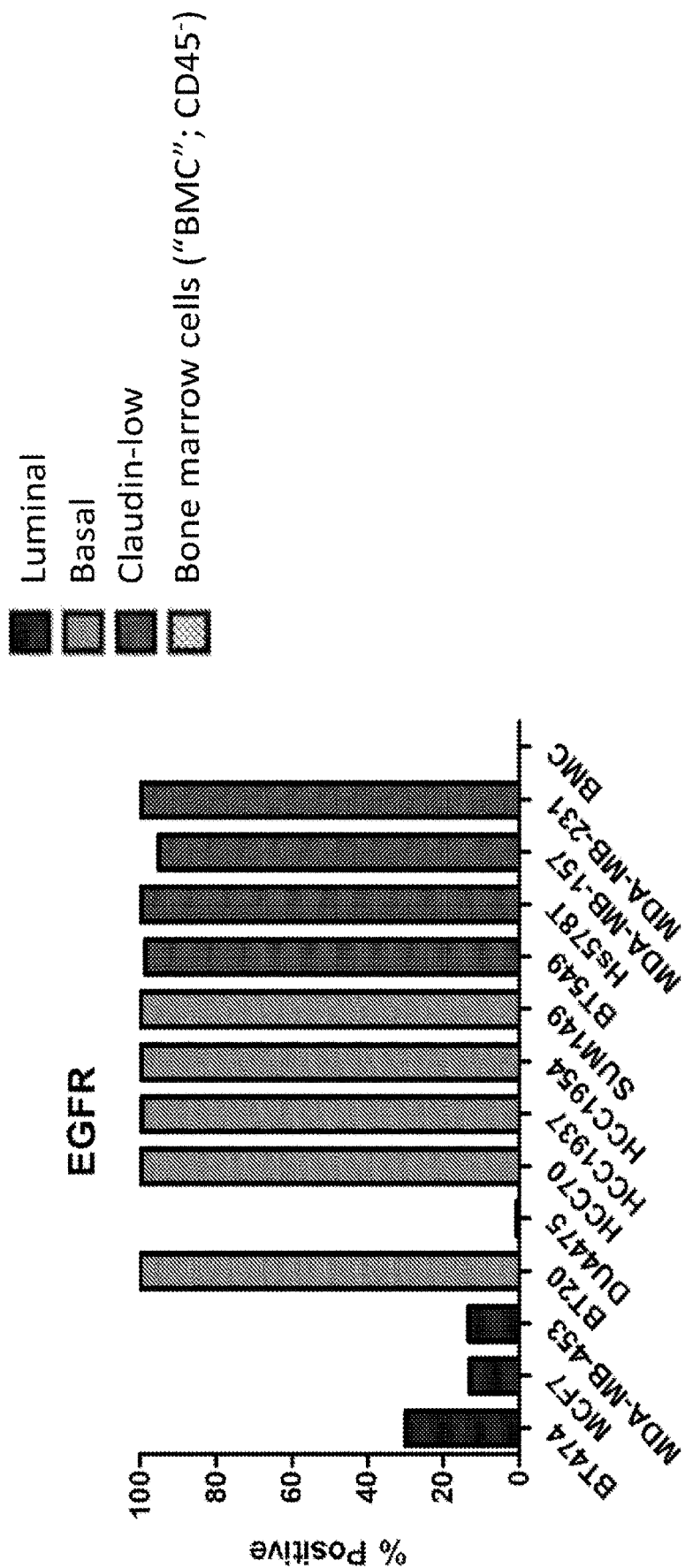

FIG. 40 depicts a summary of the results of exemplary experiments presented in FIG. 37 through FIG. 39 demonstrating the percentage of positive EGFR labeling of human breast cancer cell lines.

Figure 41:
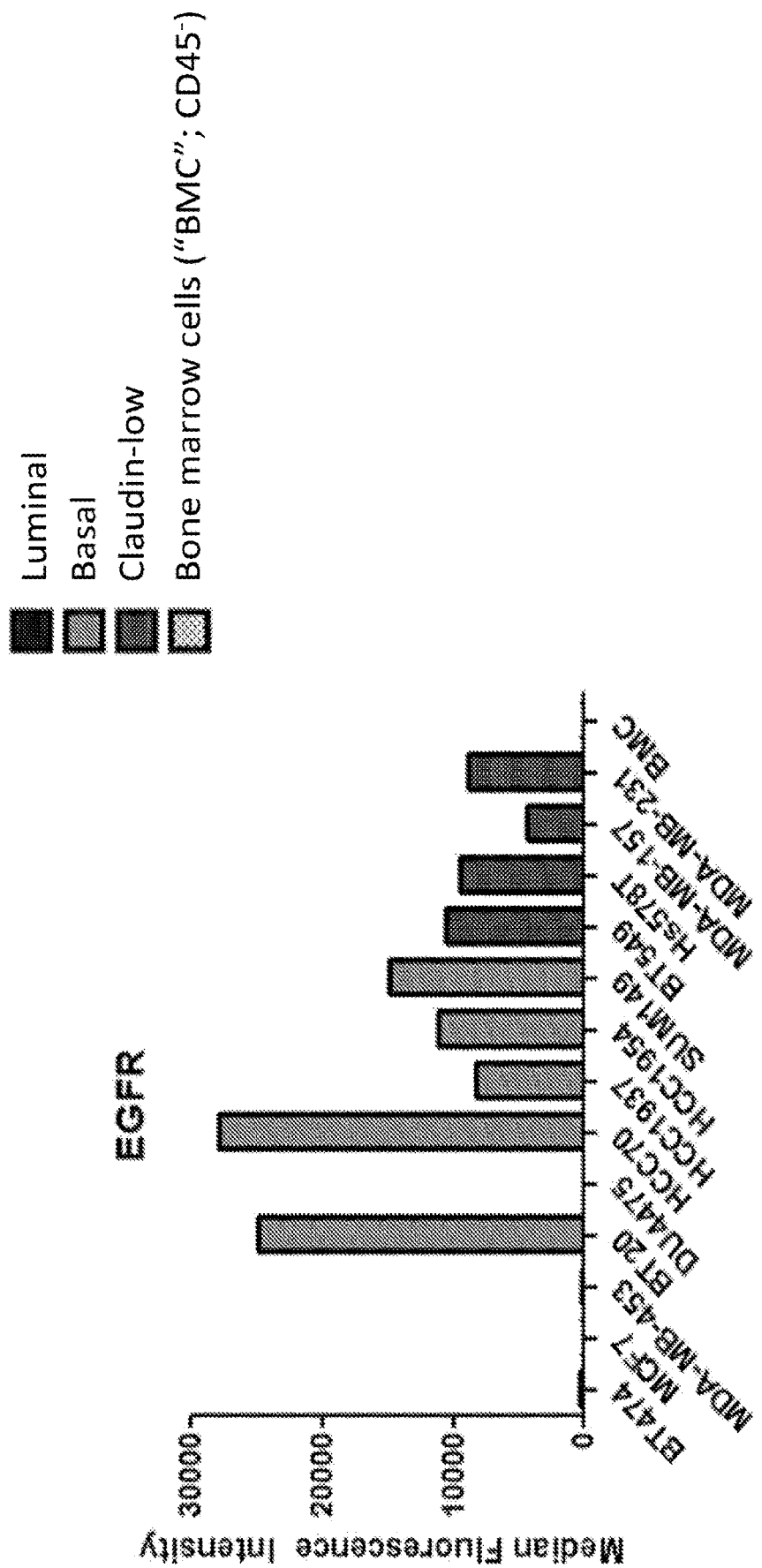

FIG. 41 depicts a summary of the results of exemplary experiments presented in FIG. 37 through FIG. 39 demonstrating the median fluorescence intensity of EGFR labeled cells for different human breast cancer cell lines.

Figure 42:
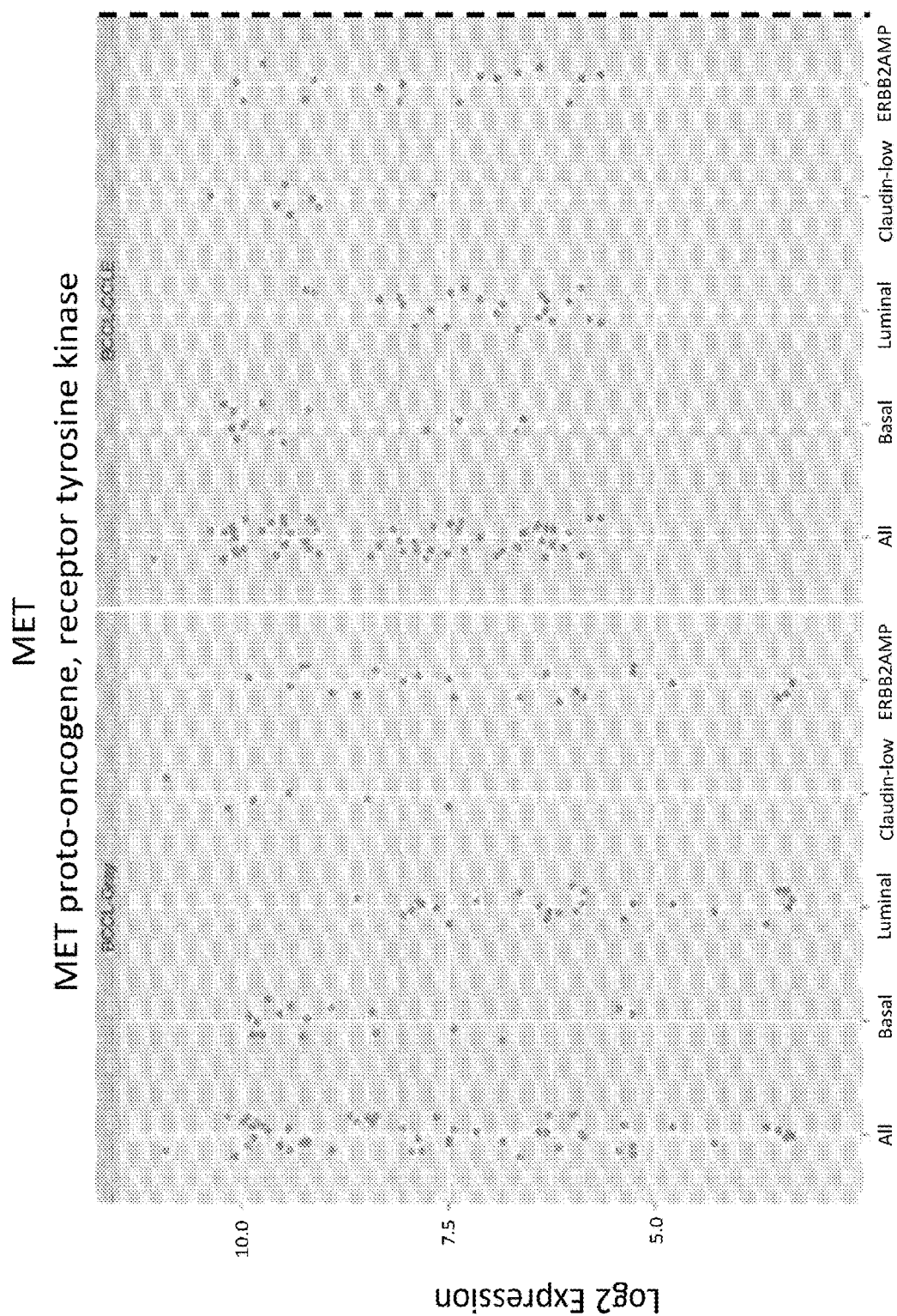
Figure 42:
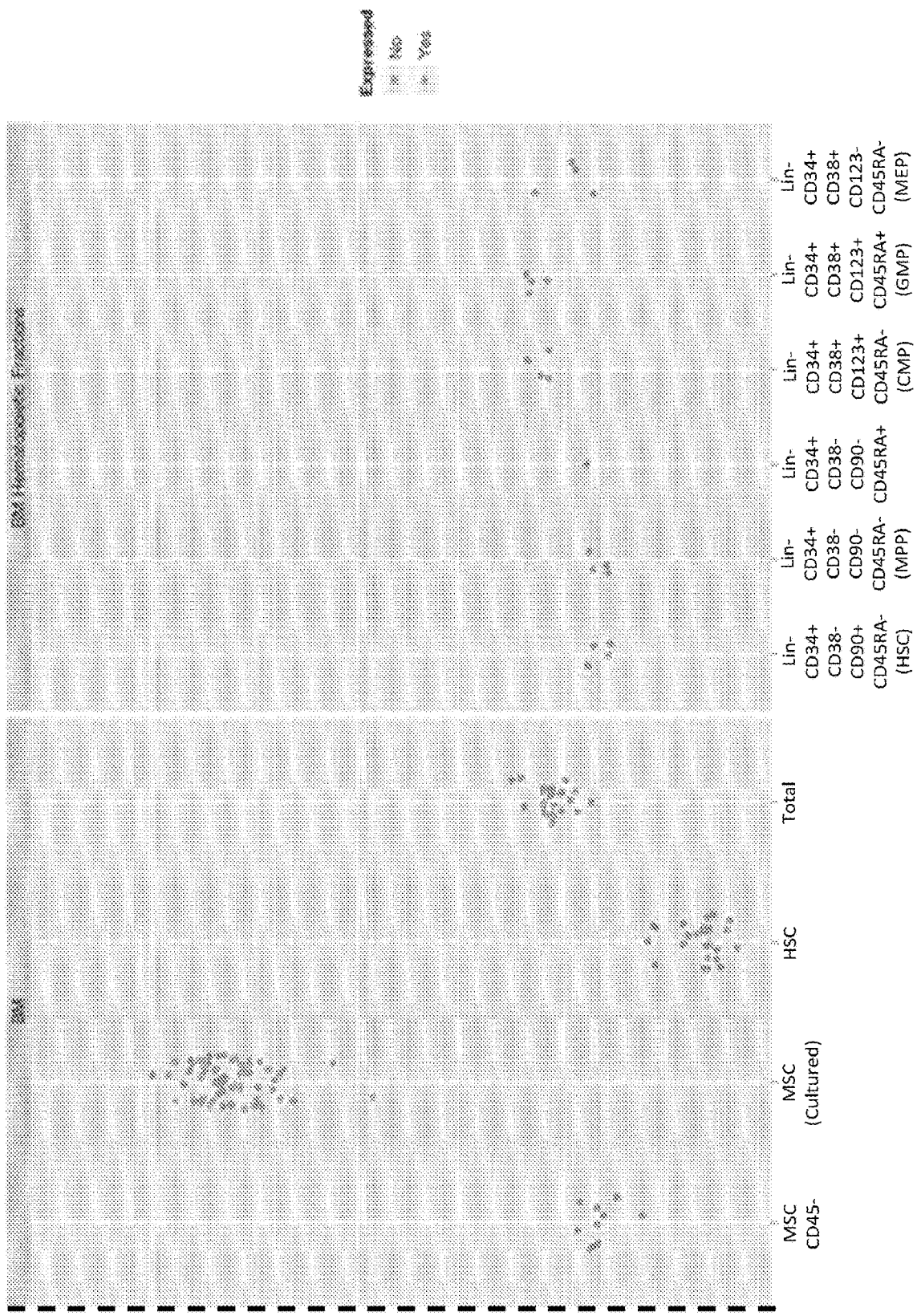

FIG. 42 depicts an analysis of the expression of c-Met across multiple breast cancer cell lines.

Figure 43:
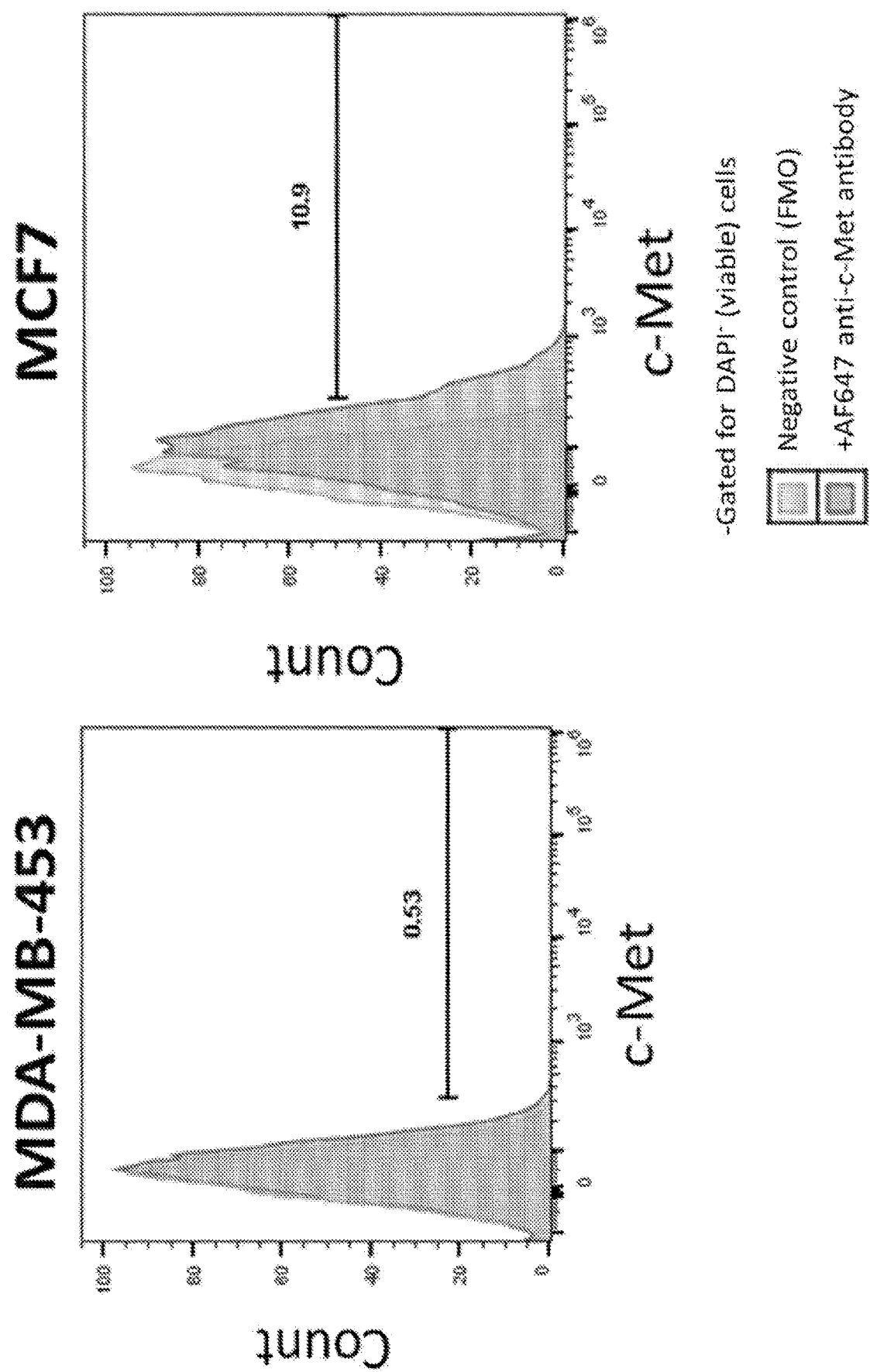

FIG. 43 depicts the results of exemplary experiments demonstrating c-Met labeling of luminal human breast cancer cell lines. BCC lines were stained with an anti-c-Met antibody conjugated to the fluorochrome Alexa Fluor 647 (AF647). Histograms show AF647-c-Met fluorescence intensity, as determined using an Attune NxT acoustic focusing flow cytometer (Gated for DAPI⁻ (viable) cells), compared to "fluorescence-minus-one" (FMO) negative controls, in which the AF647 anti-c-Met antibody was omitted from the staining reaction. Data analysis was performed using FlowJo analysis software.

Figure 44:
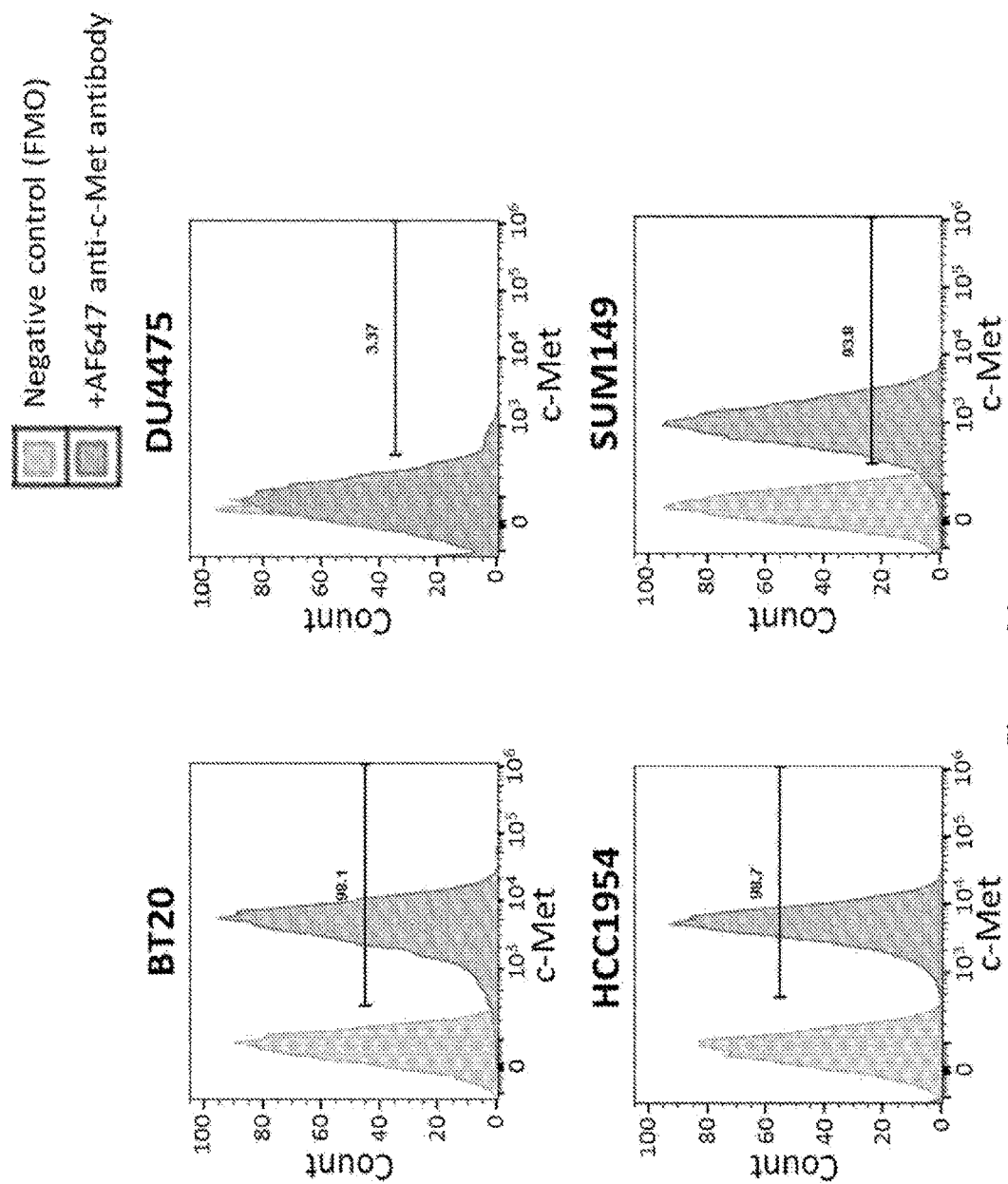

FIG. 44 depicts the results of exemplary experiments demonstrating c-Met labeling of basal human breast cancer cell lines. BCC lines were stained with an anti-c-Met antibody conjugated to the fluorochrome AF647. Histograms show AF647-c-Met fluorescence intensity, as determined using an Attune NxT acoustic focusing flow cytometer (Gated for DAPI⁻ (viable) cells), compared to "fluorescence-minus-one" (FMO) negative controls, in which the AF647 anti-c-Met antibody was omitted from the staining reaction. Data analysis was performed using FlowJo analysis software.

Figure 45:
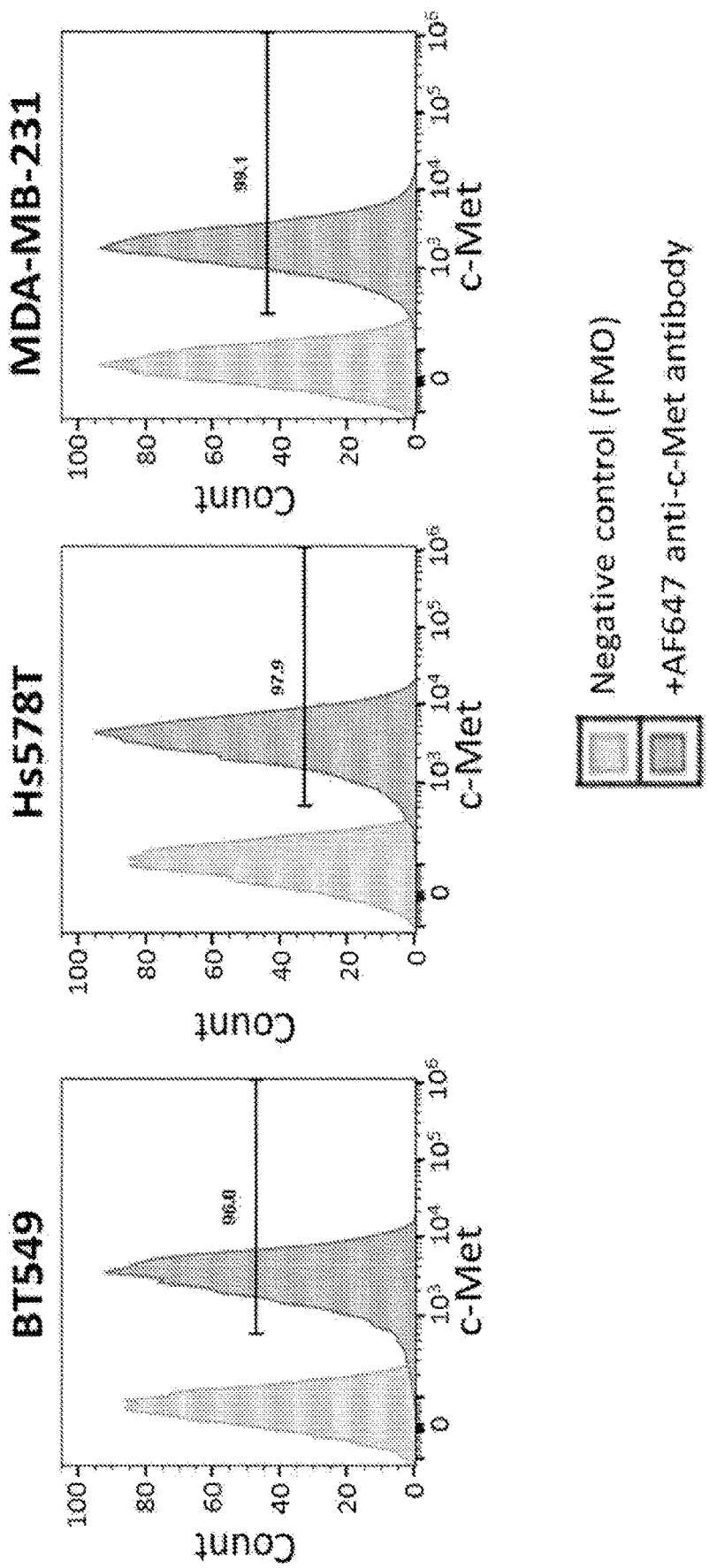

FIG. 45 depicts the results of exemplary experiments demonstrating c-Met labeling of claudin-low human breast cancer cell lines. BCC lines were stained with an anti-c-Met antibody conjugated to the fluorochrome AF647. Histograms show AF647-c-Met fluorescence intensity, as determined using an Attune NxT acoustic focusing flow cytometer (Gated for DAPI⁻ (viable) cells), compared to "fluorescence-minus-one" (FMO) negative controls, in which the AF647 anti-c-Met antibody was omitted from the staining reaction. Data analysis was performed using FlowJo analysis software.

Figure 46:
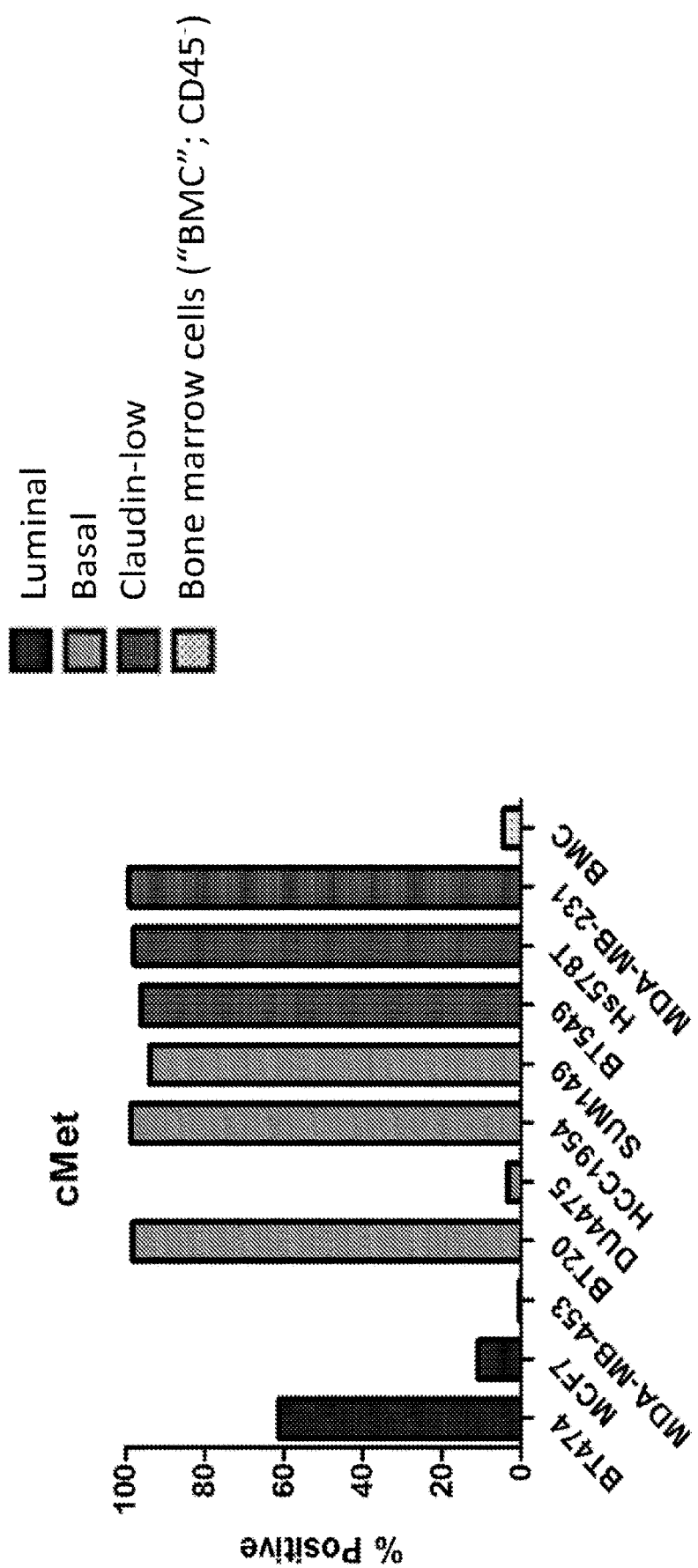

FIG. 46 depicts a summary of the results of exemplary experiments presented in FIG. 43 through FIG. 45 demonstrating the percentage of positive c-Met labeling of human breast cancer cell lines.

Figure 47:
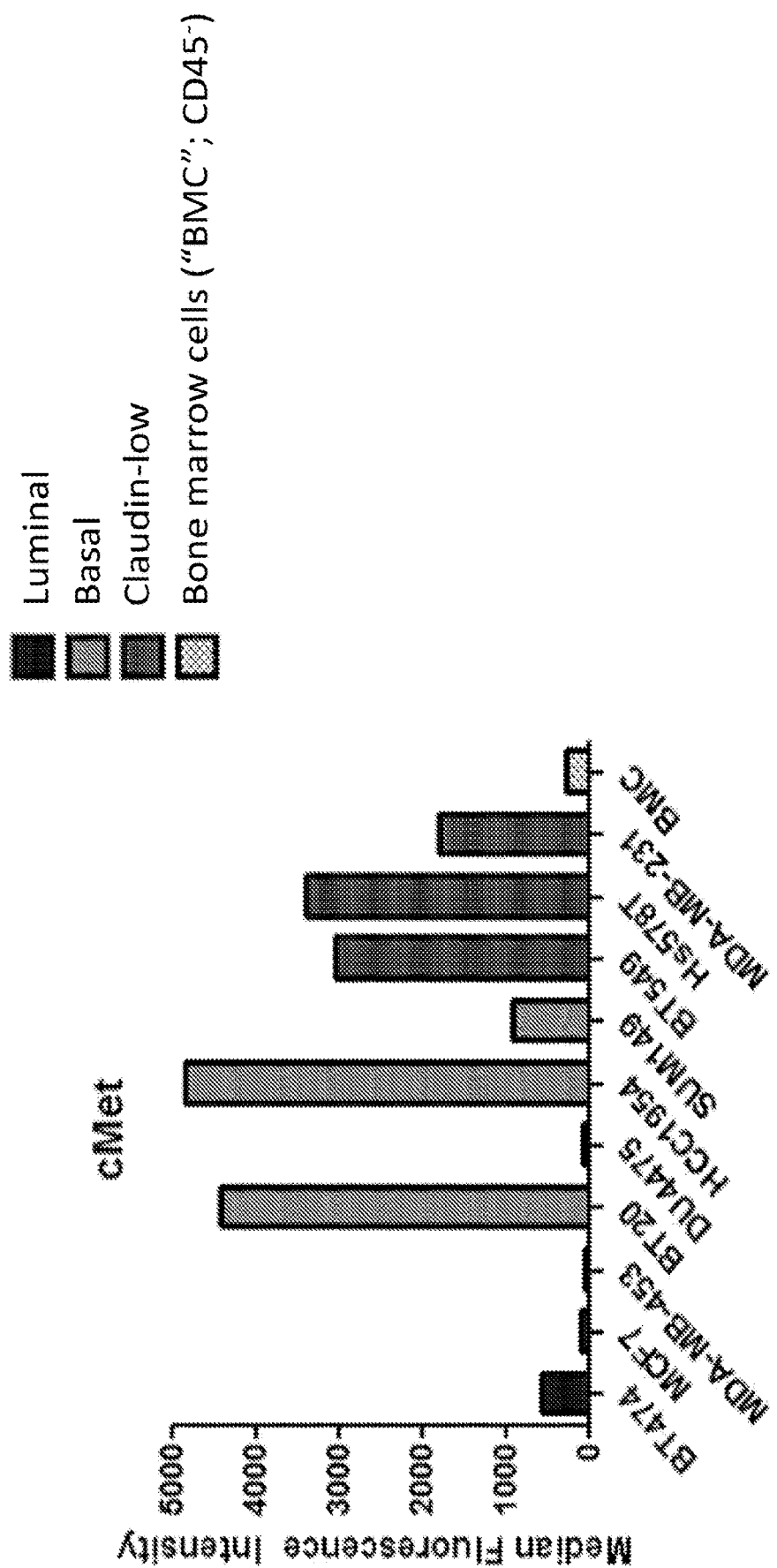

FIG. 47 depicts a summary of the results of exemplary experiments presented in FIG. 43 through FIG. 45 demonstrating the median fluorescence intensity of c-Met labeled cells for different human breast cancer cell lines.

Figure 48:
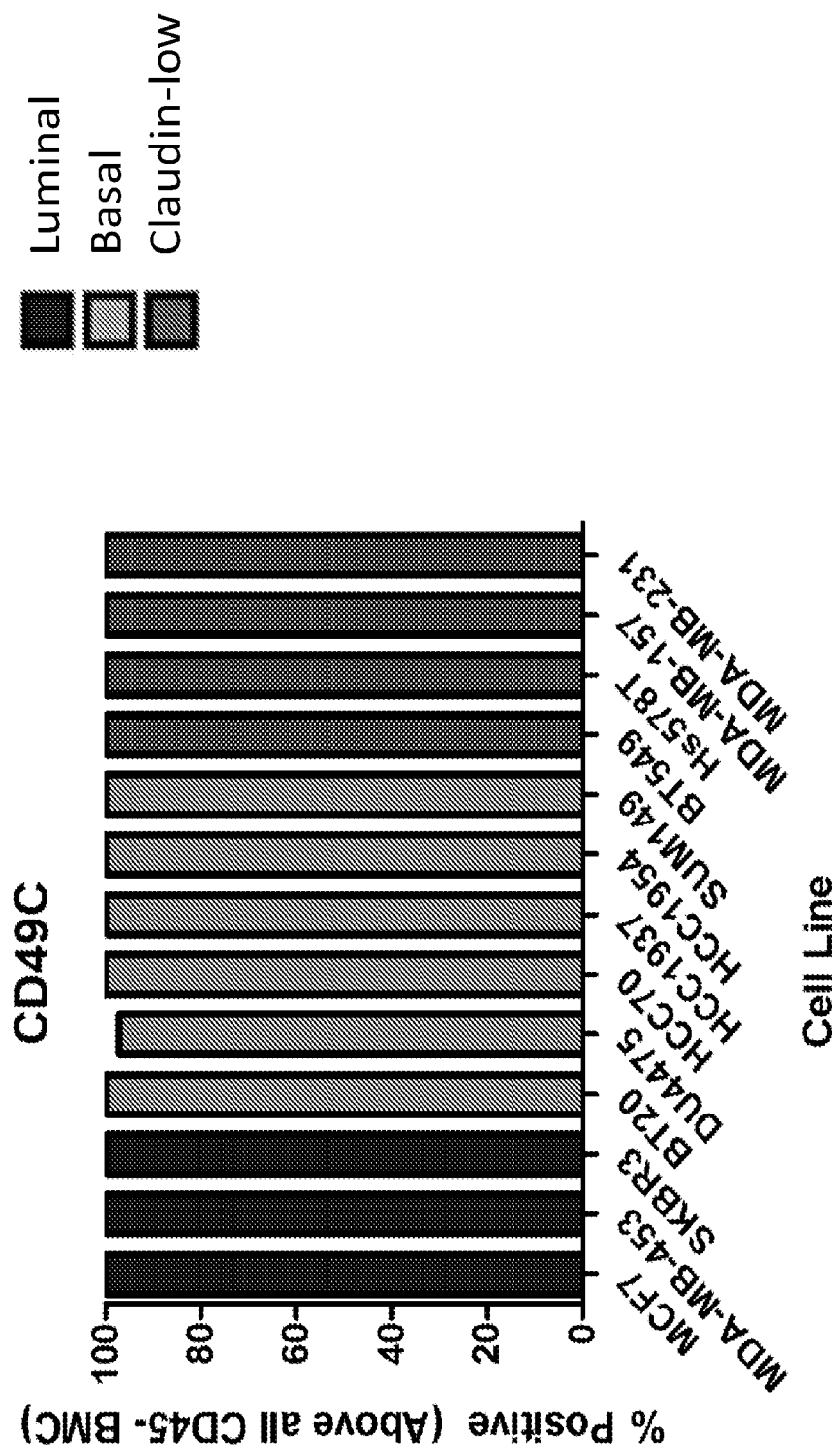

FIG. 48 depicts the results of exemplary experiments demonstrating the percentage of positive CD49C labeling of human breast cancer cell lines vs. donor bone marrow. Data shown are presented as the percentage of cells within each breast cancer cell line which have higher cell surface expression levels of CD49C than are found in CD45− negative bone marrow cells from healthy donors.

Figure 49:
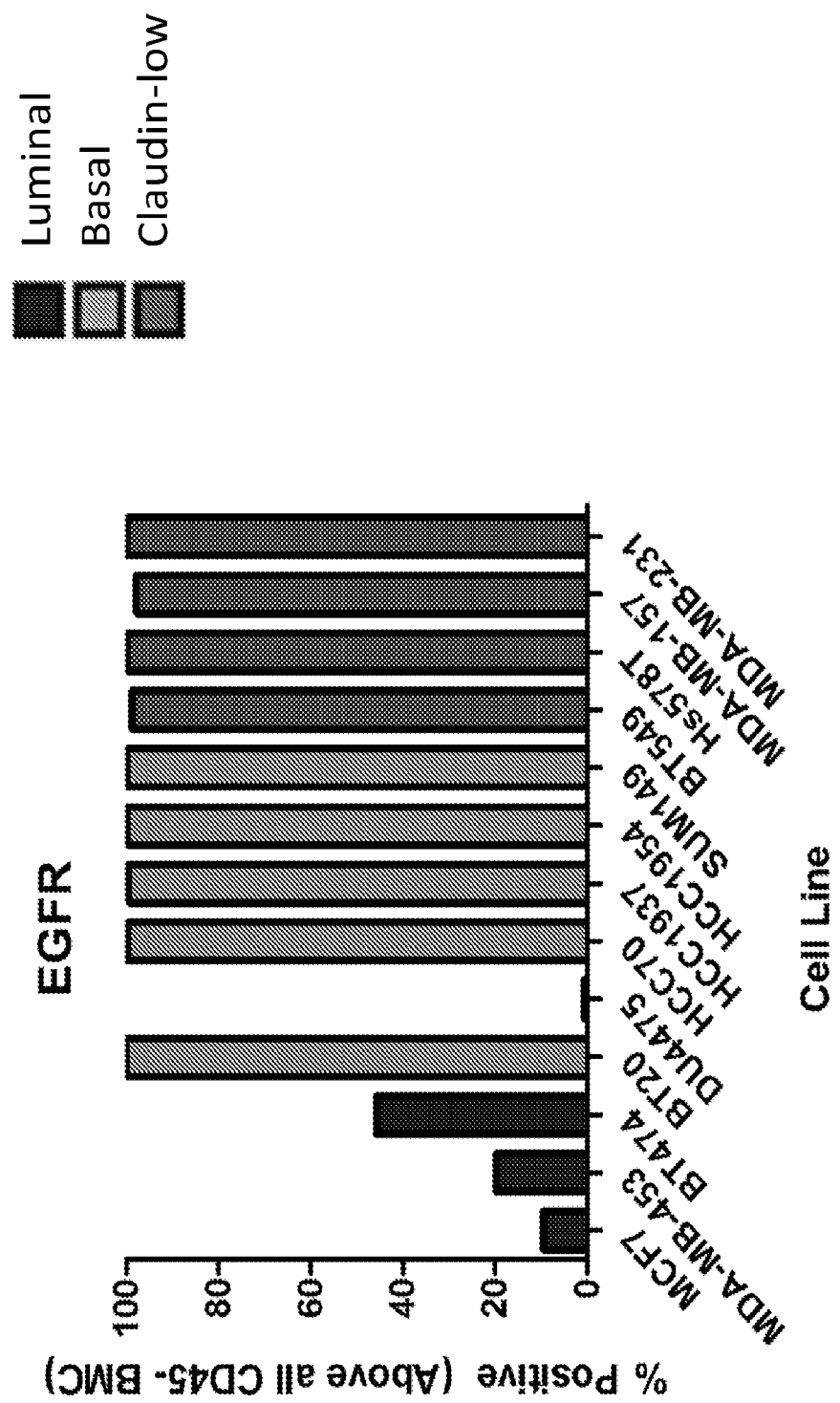

FIG. 49 depicts the results of exemplary experiments demonstrating the percentage of positive EGFR labeling of human breast cancer cell lines vs. donor bone marrow. Data shown are presented as the percentage of cells within each breast cancer cell line which have higher cell surface expression levels of EGFR than are found in CD45− negative bone marrow cells from healthy donors.

Figure 50:
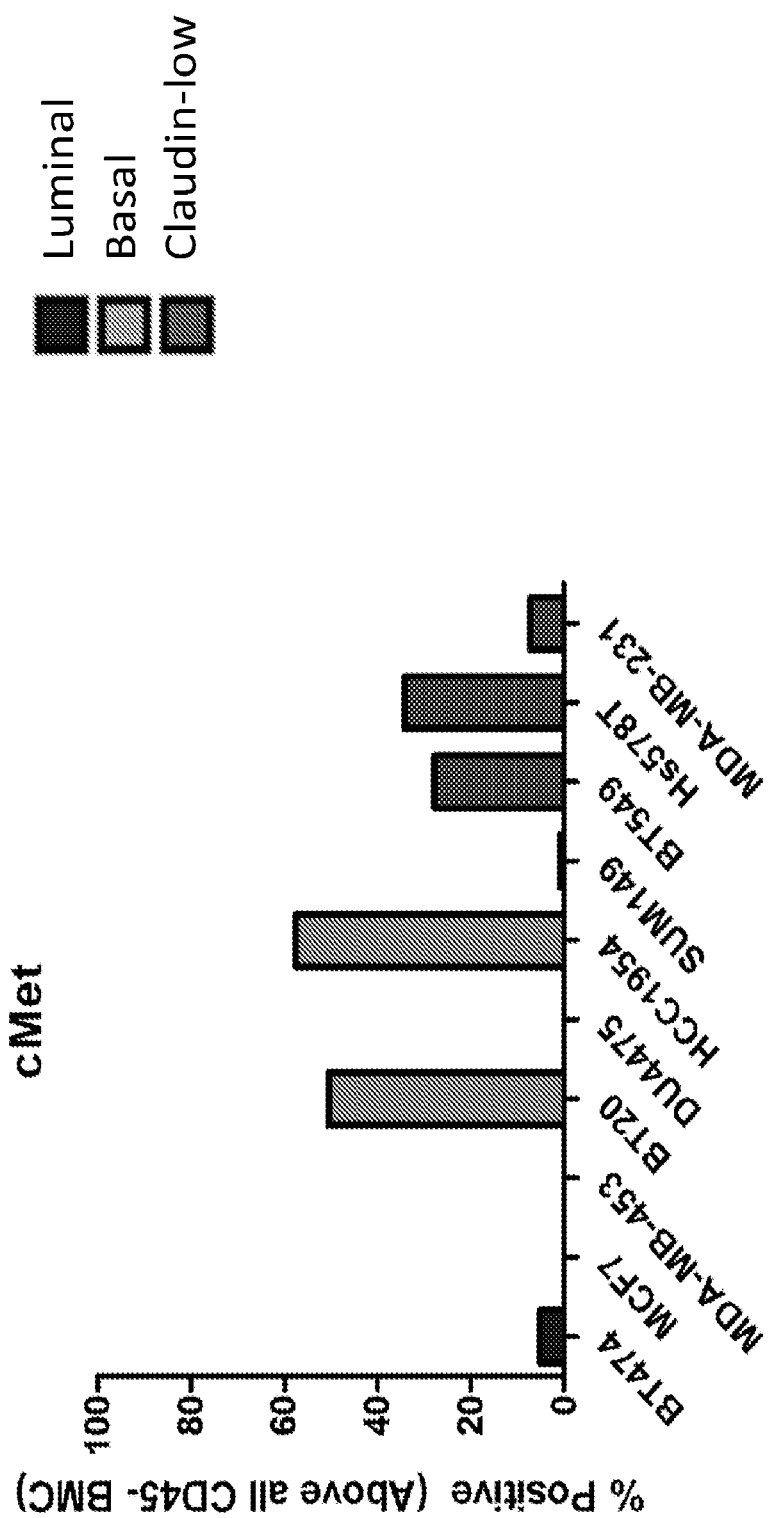

FIG. 50 depicts the results of exemplary experiments demonstrating the percentage of positive c-Met labeling of human breast cancer cell lines vs. donor bone marrow. Data shown are presented as the percentage of cells within each breast cancer cell line which have higher cell surface expression levels of c-Met than are found in CD45− negative bone marrow cells from healthy donors.

Figure 51:
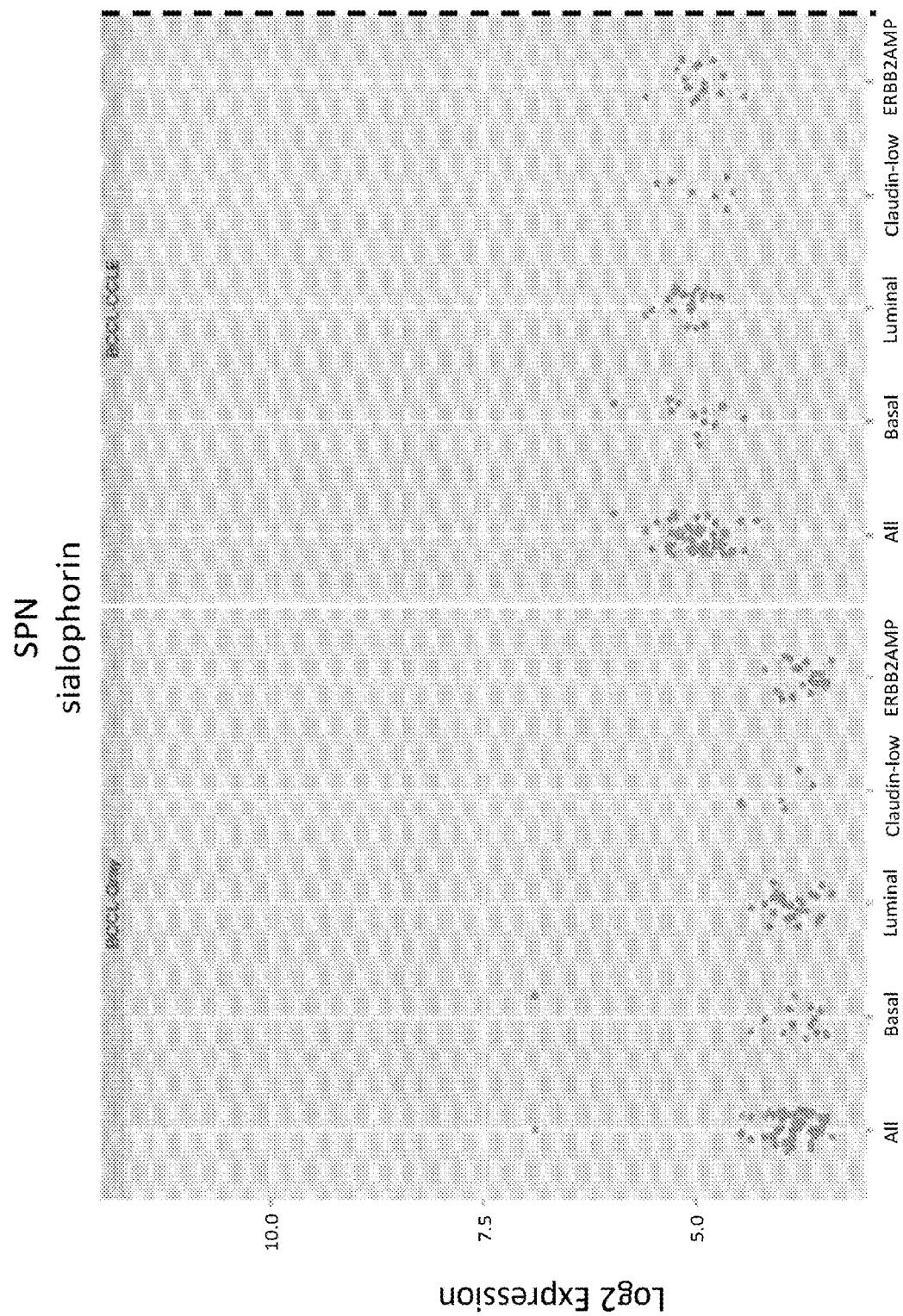
Figure 51:
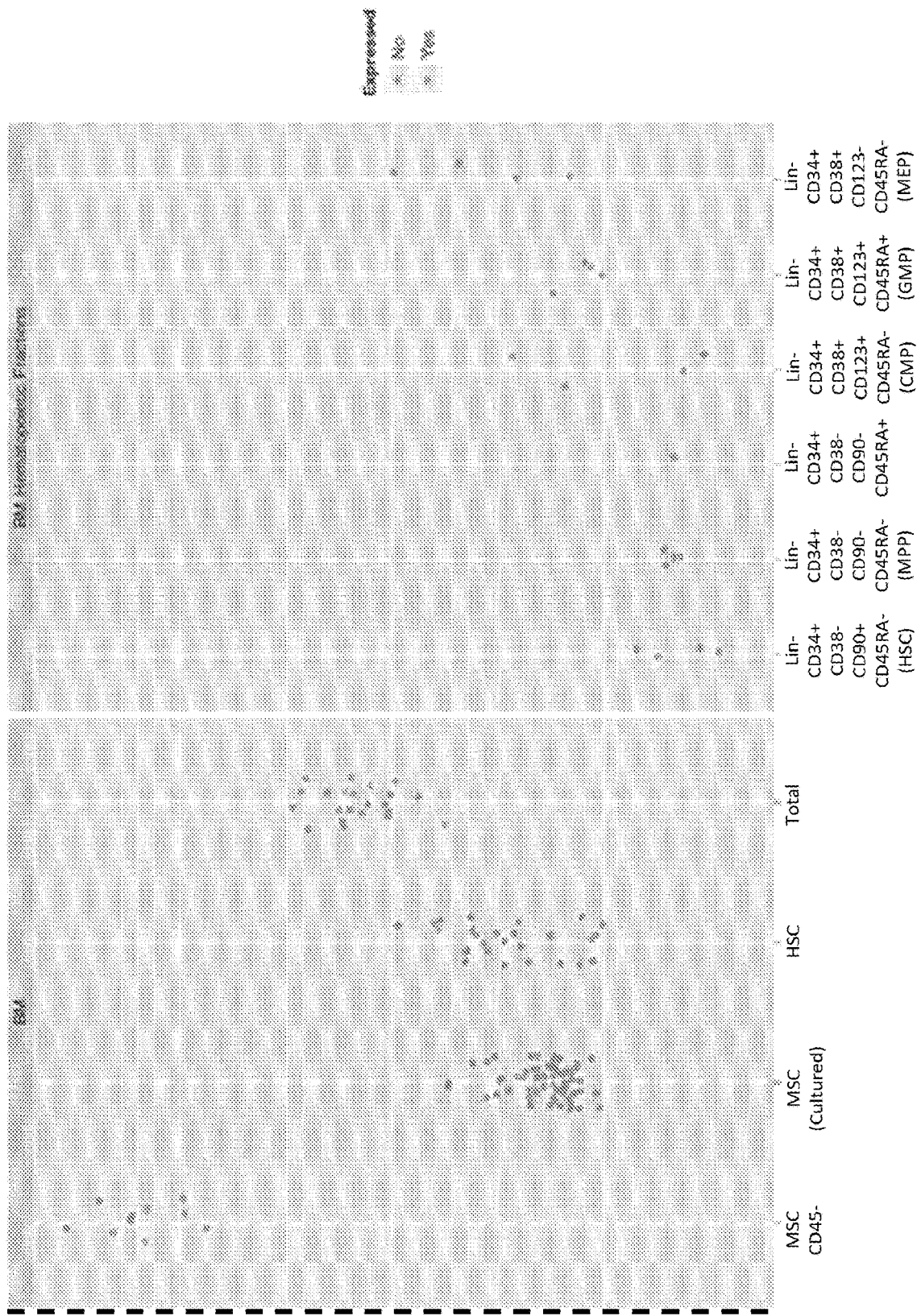

FIG. 51 depicts an analysis of the expression of CD43 across multiple breast cancer cell lines and bone marrow cell populations.

Figure 52:
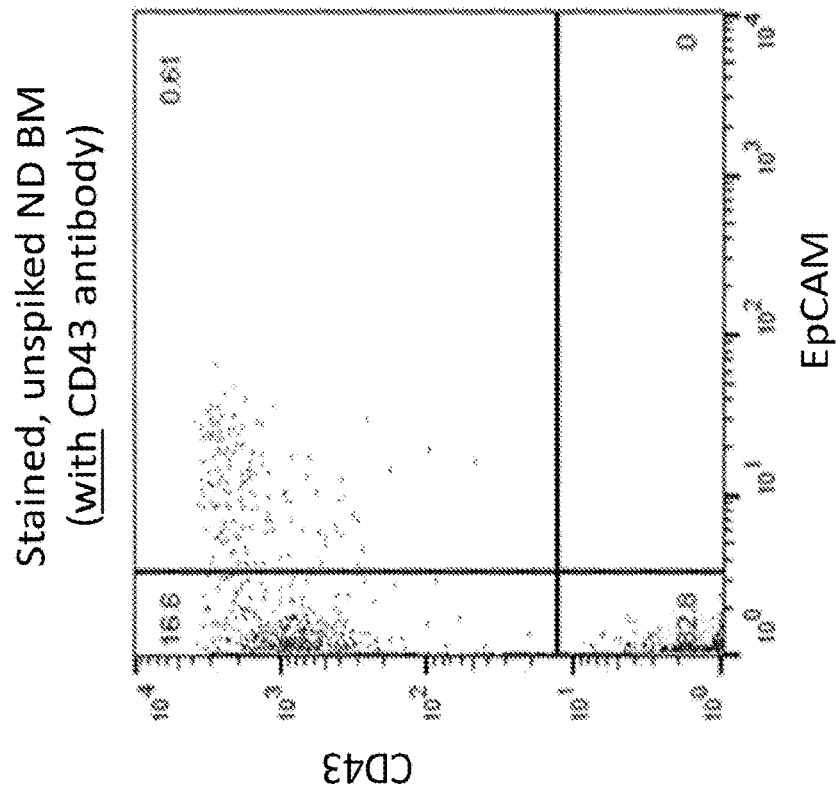

FIG. 52 depicts the results of exemplary experiments demonstrating staining with the candidate bone marrow cell marker CD43. Bone marrow cells were stained using antibodies recognizing CD45, EpCAM, and CD43, as well as DAPI to identify viable (DAPI-negative) cells. The experiments were gated for DAPI⁻/non-debris/CD45⁻ events.

Figure 53:
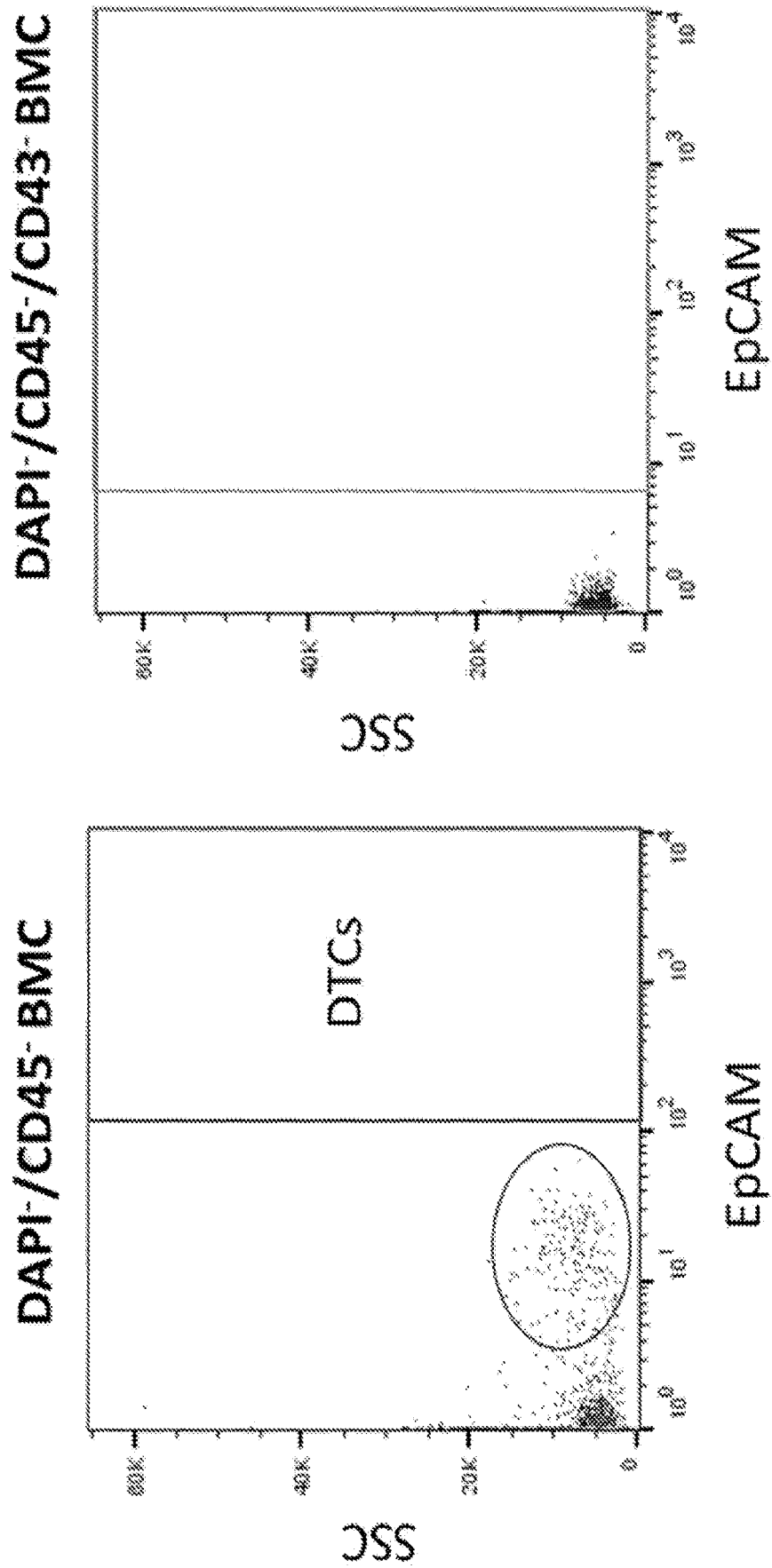

FIG. 53 depicts the results of exemplary experiments demonstrating adding CD43 negative selection reduces EpCAM "background" in unspiked bone marrow.

Figure 54:
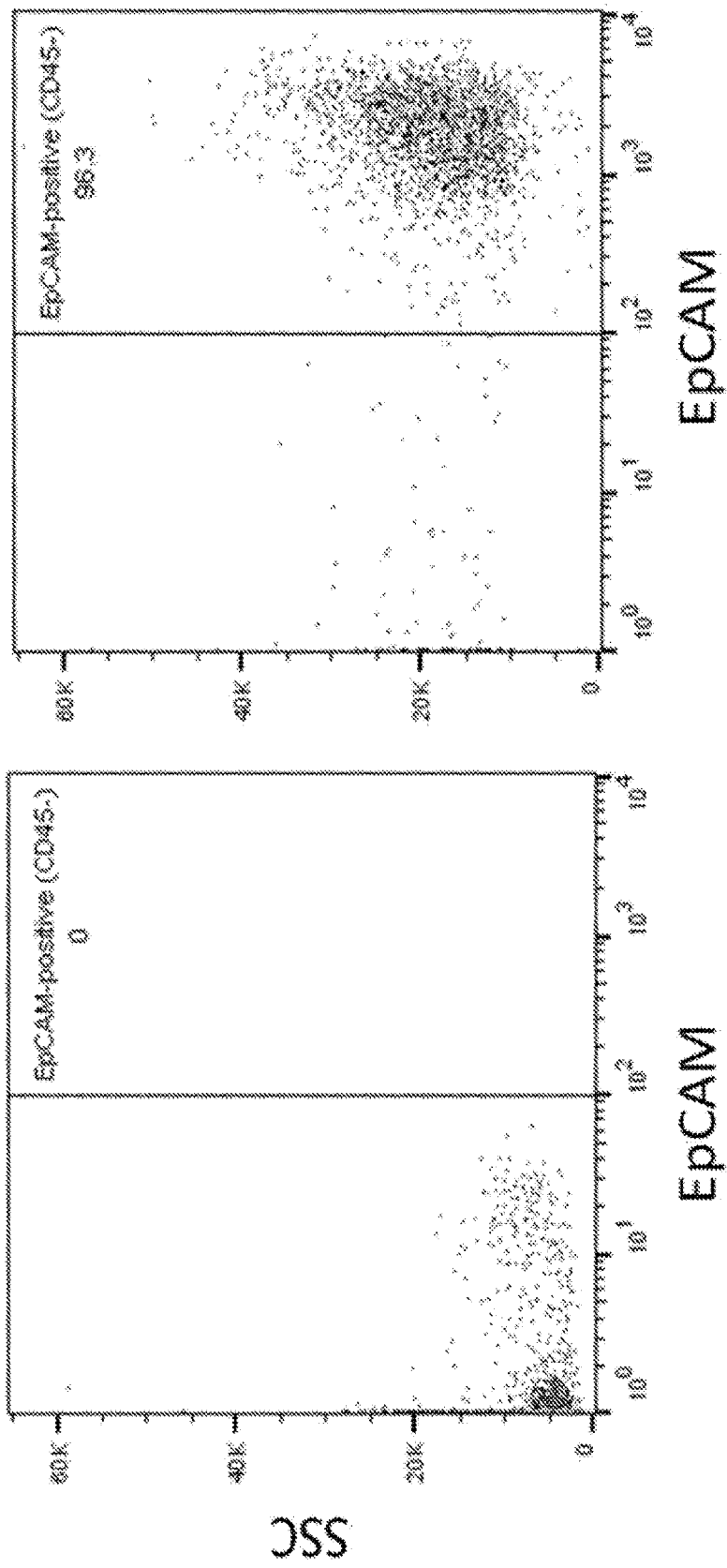
Figure 54:
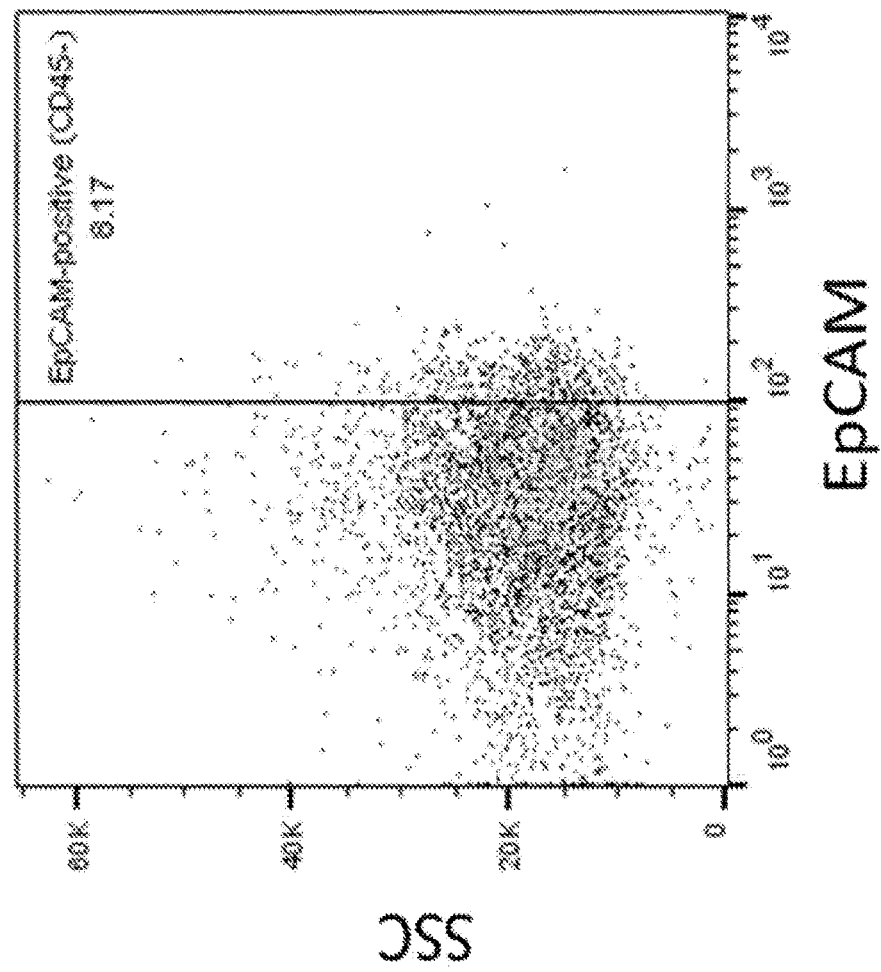

FIG. 54 depicts the results of exemplary experiments demonstrating DAPI−/CD45− negative selection results in EpCAM "background" in unspiked bone marrow.

Figure 55:
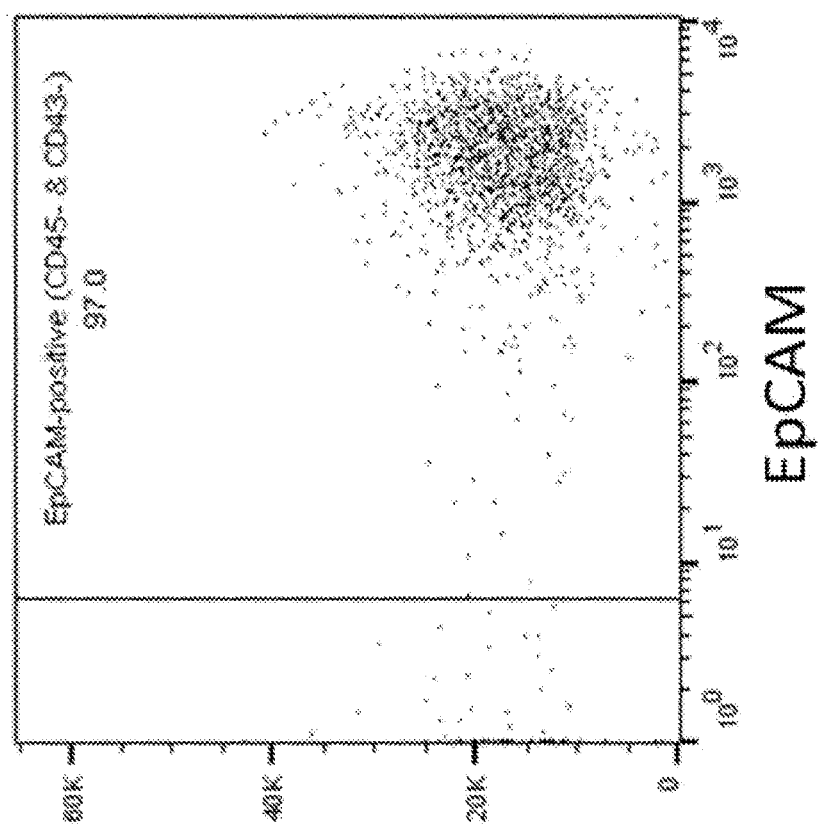
Figure 55:
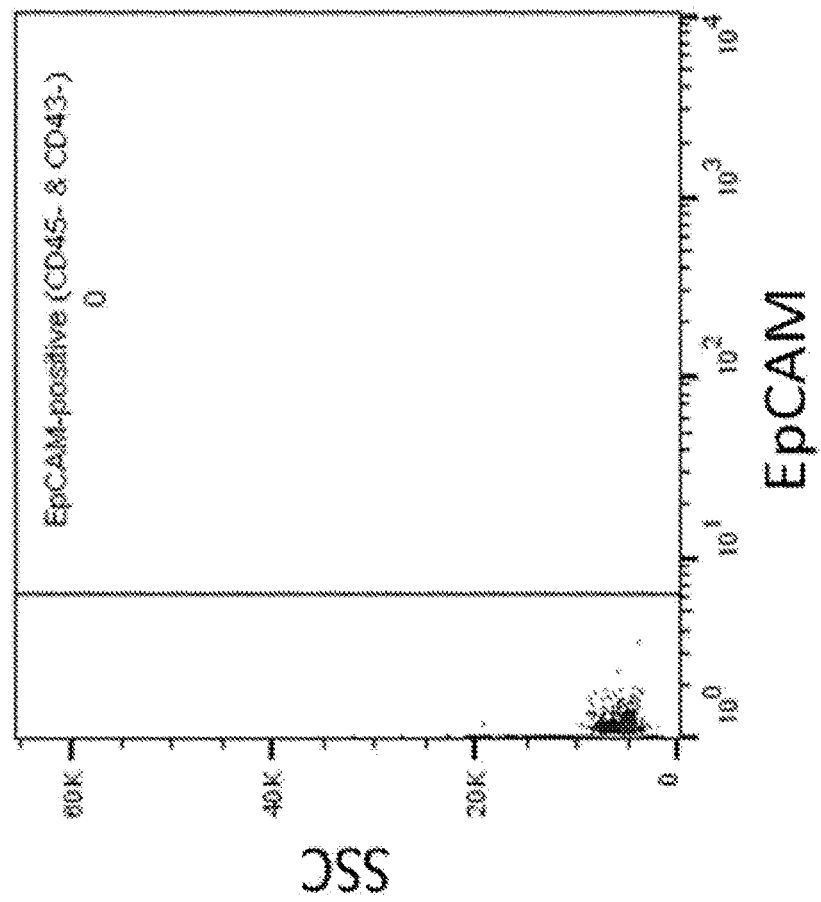
Figure 55:
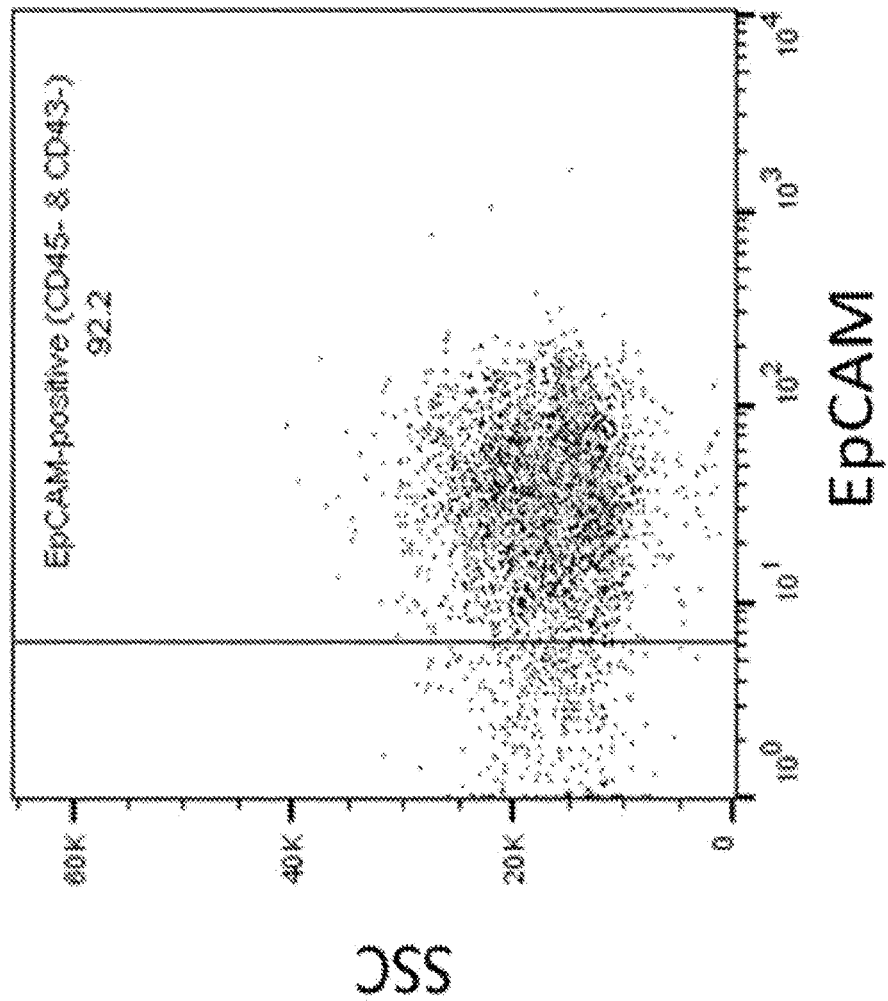

FIG. 55 depicts the results of exemplary experiments demonstrating DAPI−/CD45−/CD43− negative selection lowers EpCAM "background" in unspiked bone marrow.

Figure 56:
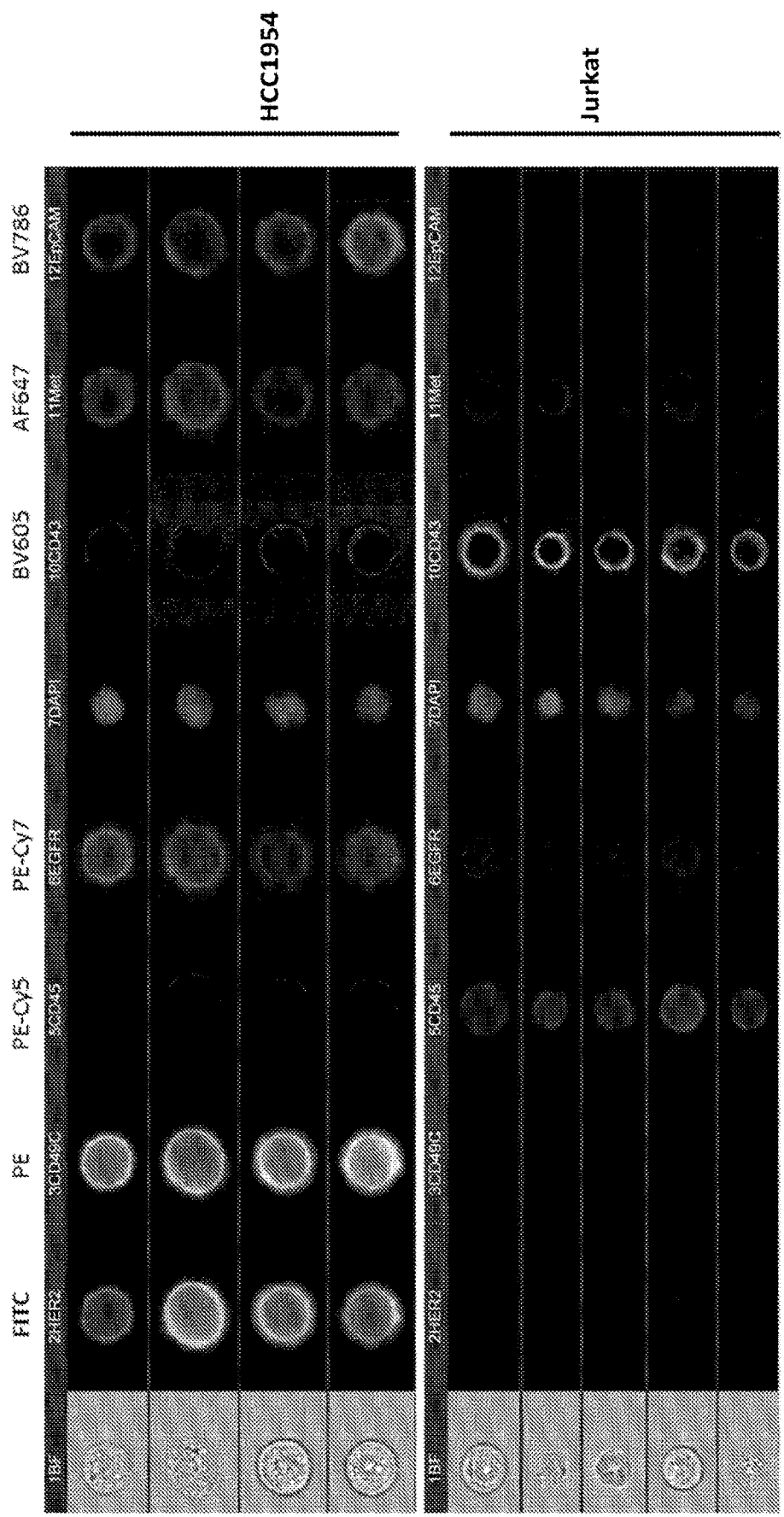

FIG. 56 depicts the results of exemplary experiments demonstrating an ImageStream® analysis of an 8-color DTC staining panel.

Figure 57:
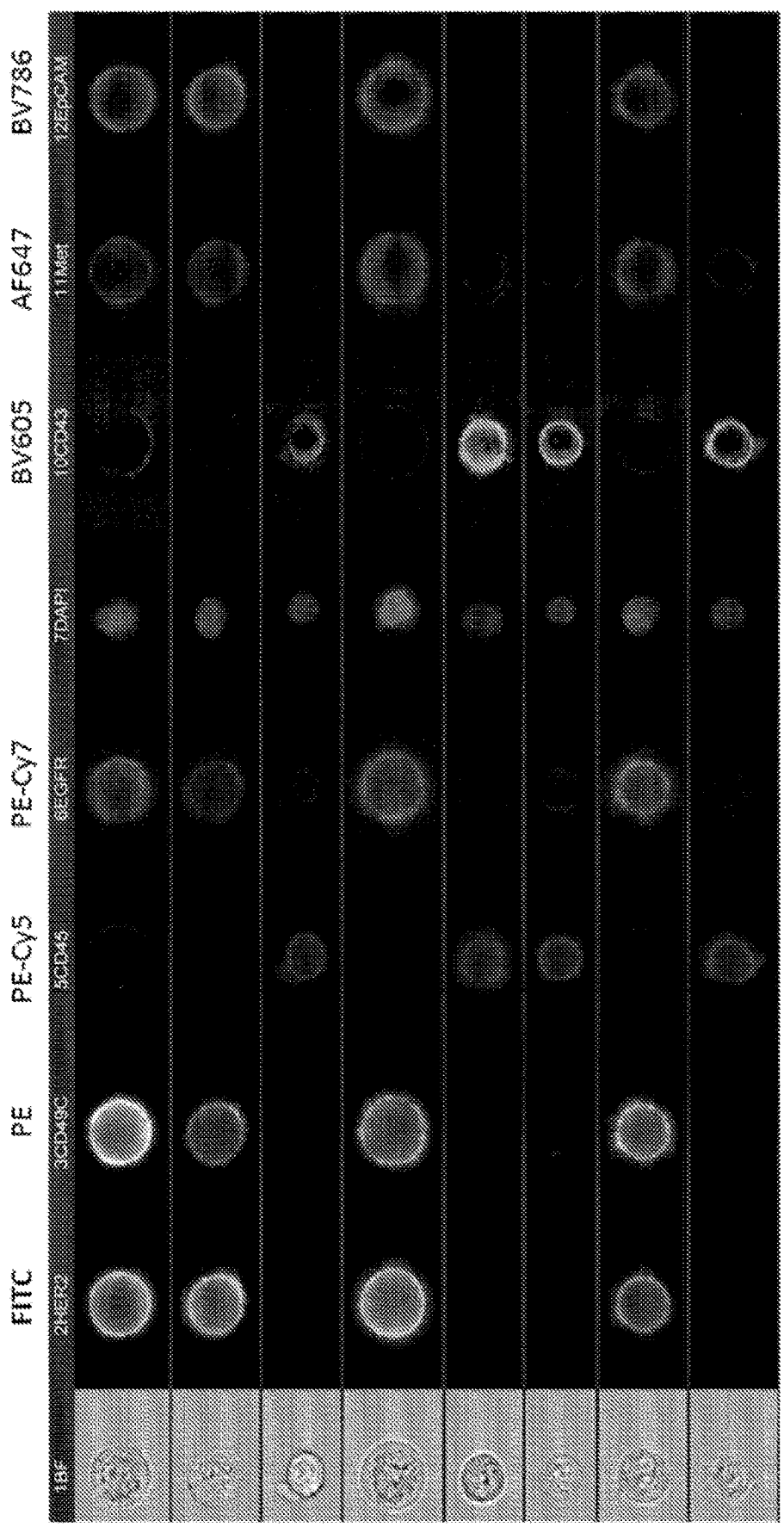
Figure 57:
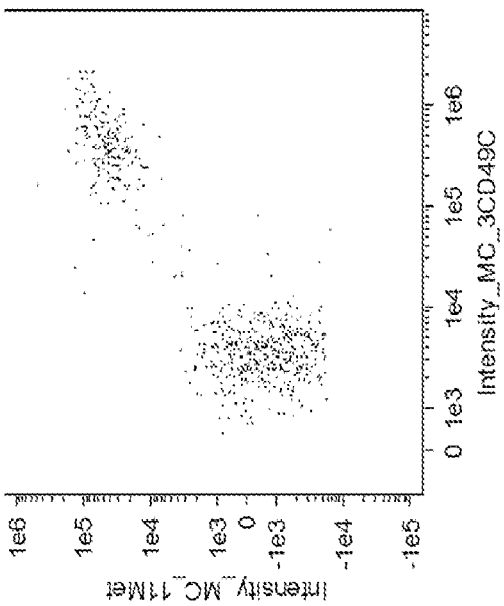
Figure 57:
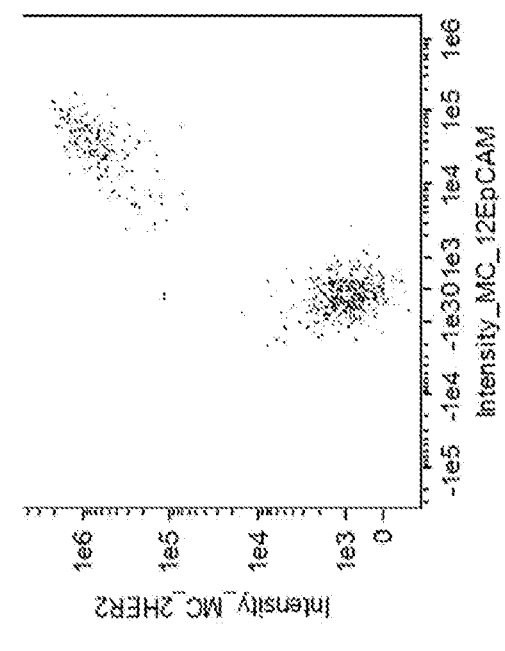
Figure 57:
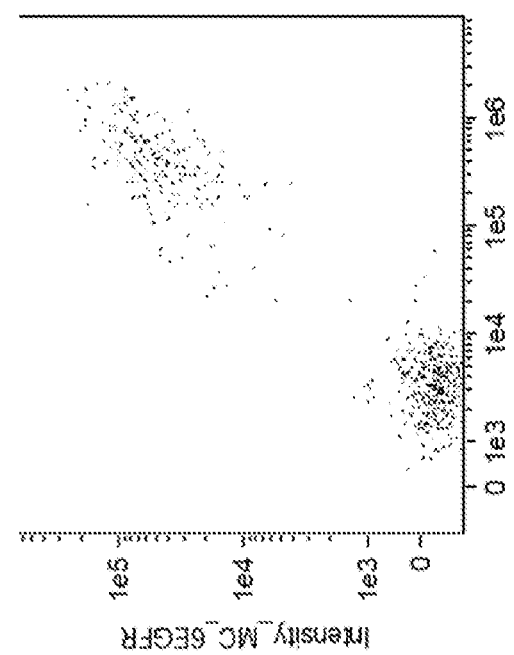

FIG. 57 depicts the results of exemplary experiments demonstrating an ImageStream® analysis of an 8-color DTC staining panel is able to distinguish between cell types.

Figure 58:
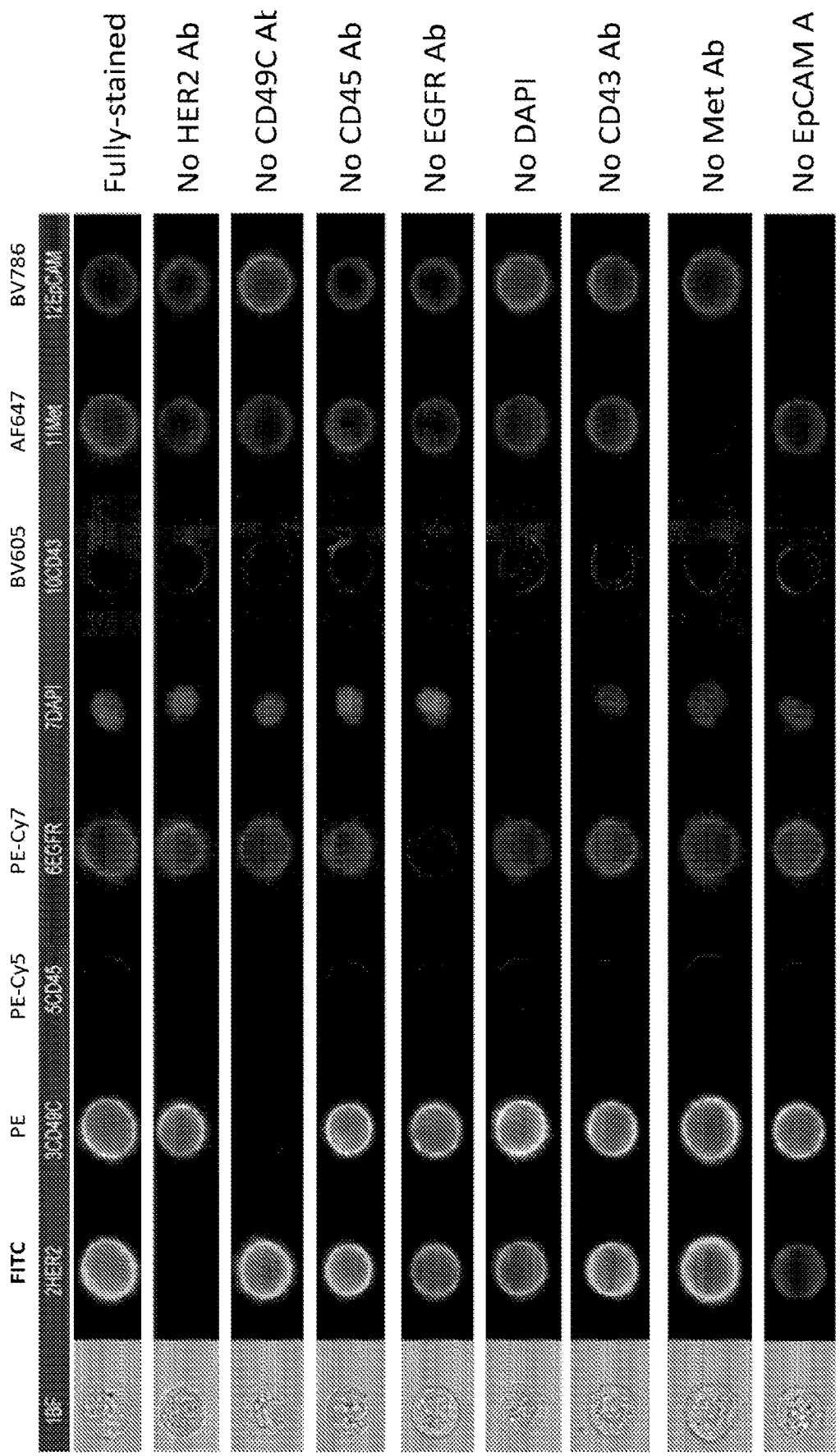

FIG. 58 depicts the results of exemplary experiments demonstrating the specificity of the 8-color DTC staining panel on HCC1954 cells.

Figure 59:
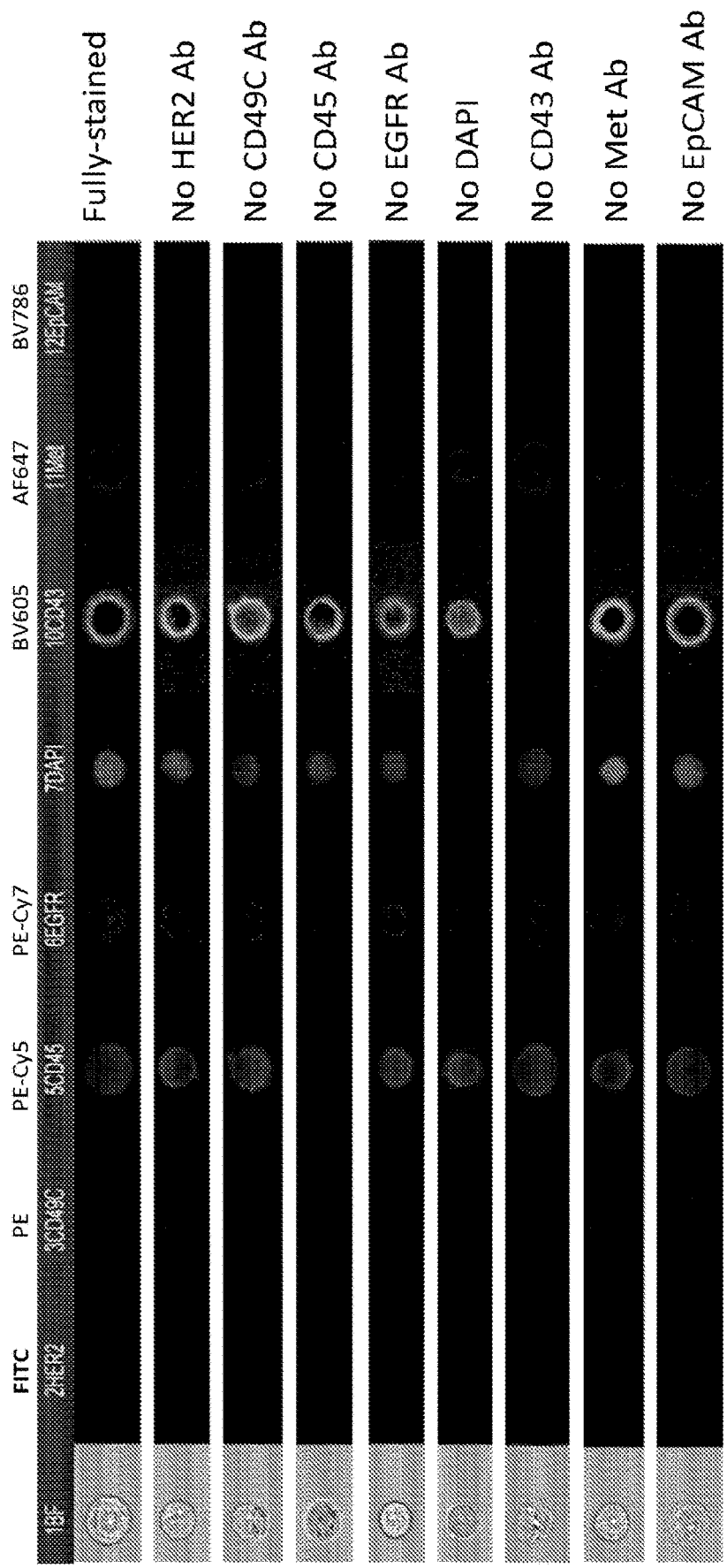

FIG. 59 depicts the results of exemplary experiments demonstrating the specificity of the 8-color DTC staining panel on Jurkat cells.

Figure 60:
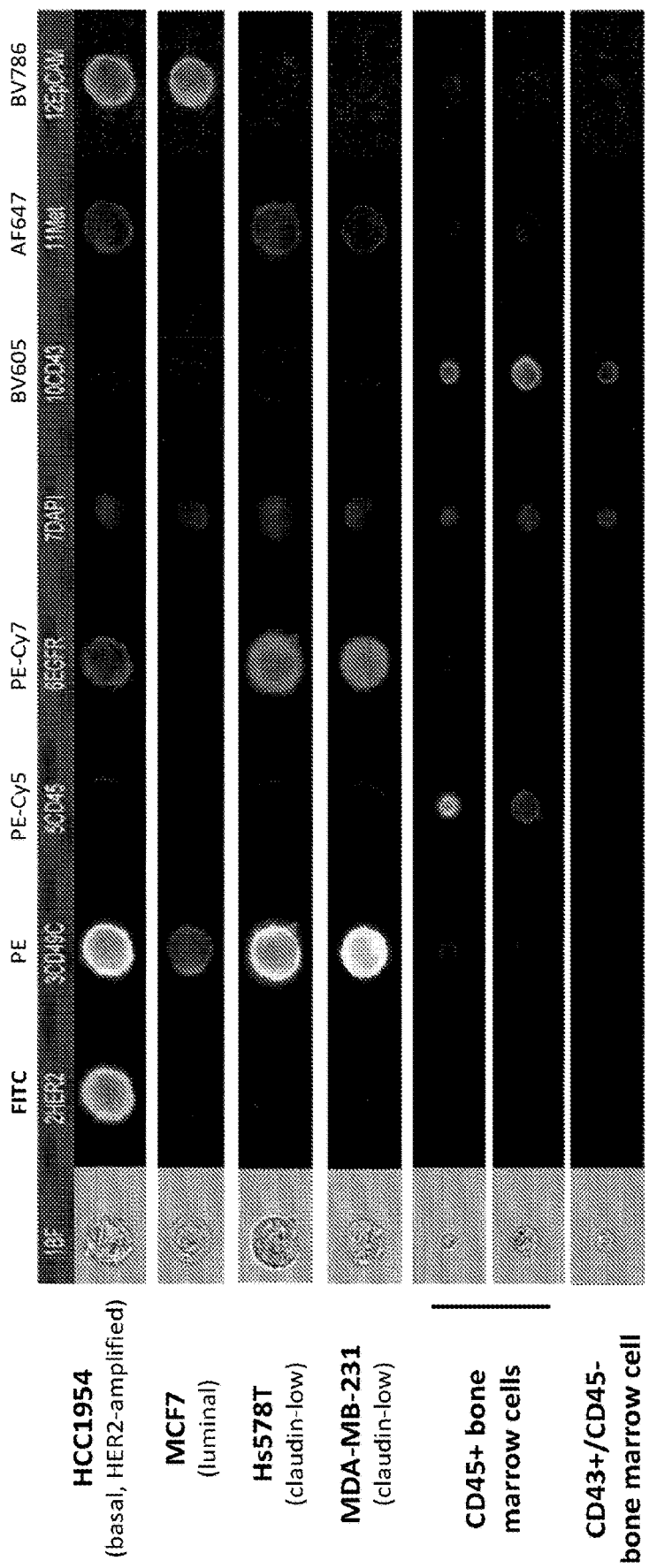

FIG. 60 depicts the results of exemplary experiments demonstrating an ImageStream® analysis of breast cancer cells of multiple subtypes using an 8-color DTC staining panel.

Figure 61:
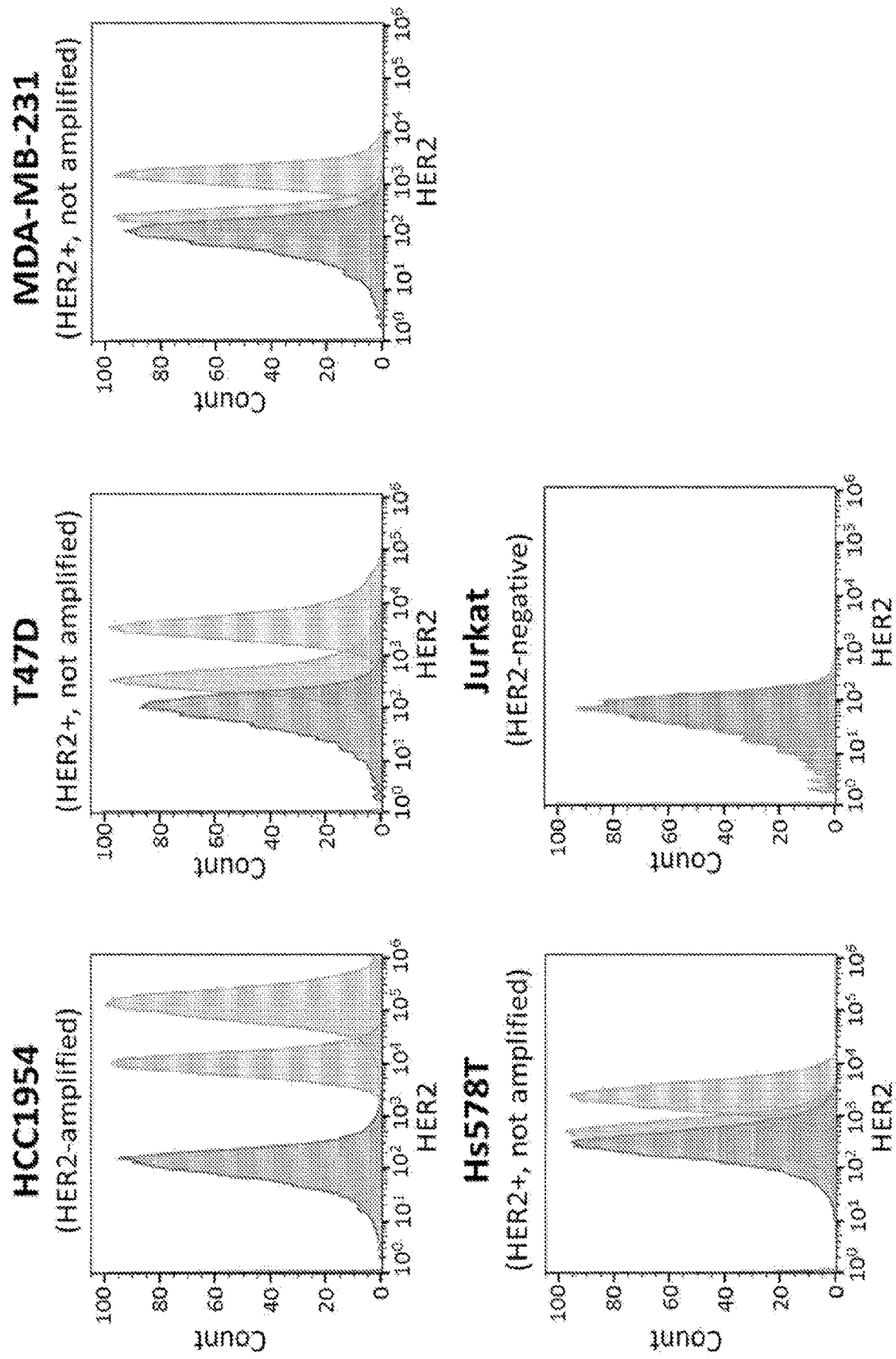

FIG. 61 depicts the results of exemplary experiments demonstrating staining using BB515 anti-HER2 (custom conjugate) vs. FITC anti-HER2. Red=unstained control; blue=FITC anti-HER2; orange=BB515 anti-HER2.

Figure 62:
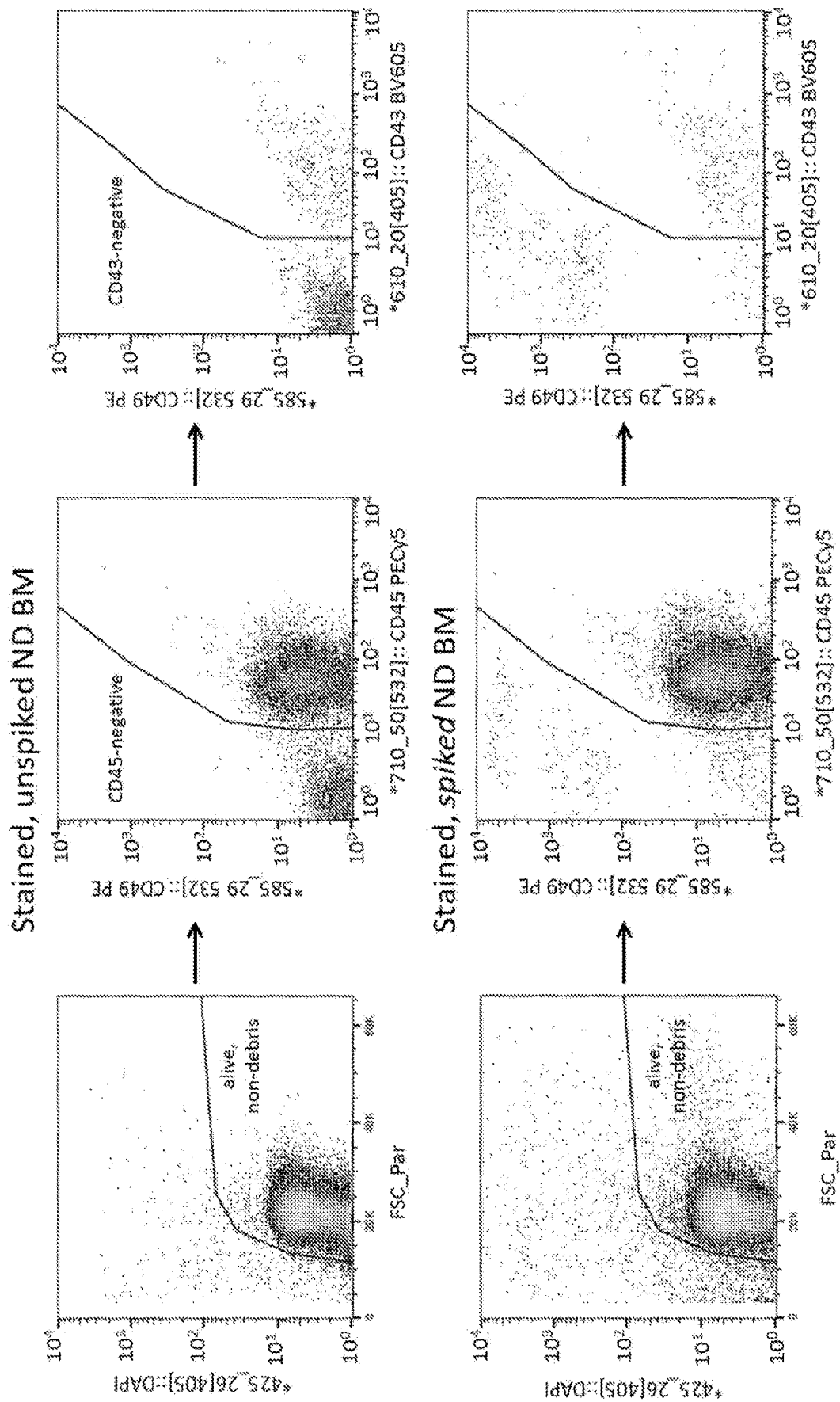

FIG. 62 depicts the results of exemplary experiments demonstrating the gating strategy used for flow cytometry experiments testing the 8-color DTC panel.

Figure 63:
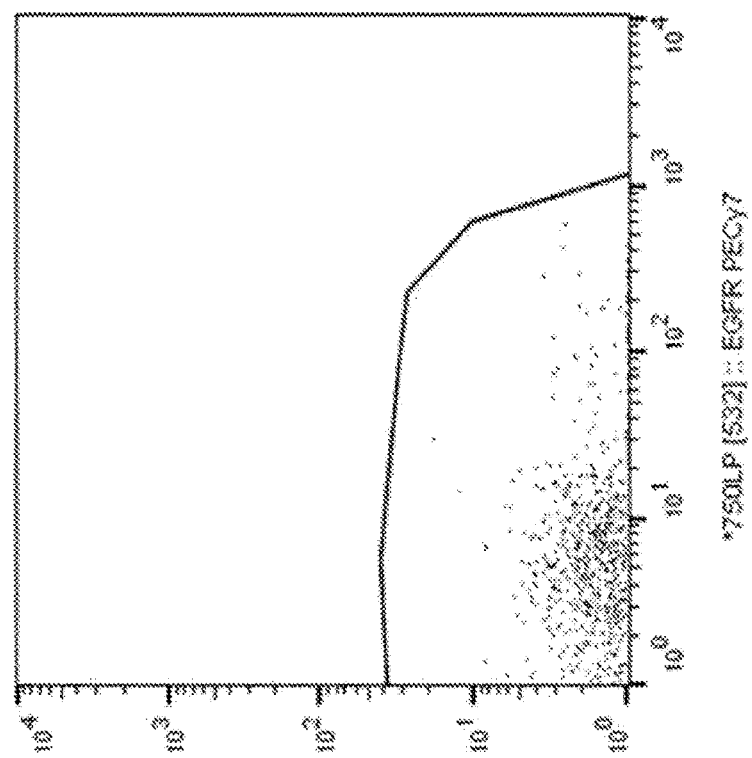
Figure 63:
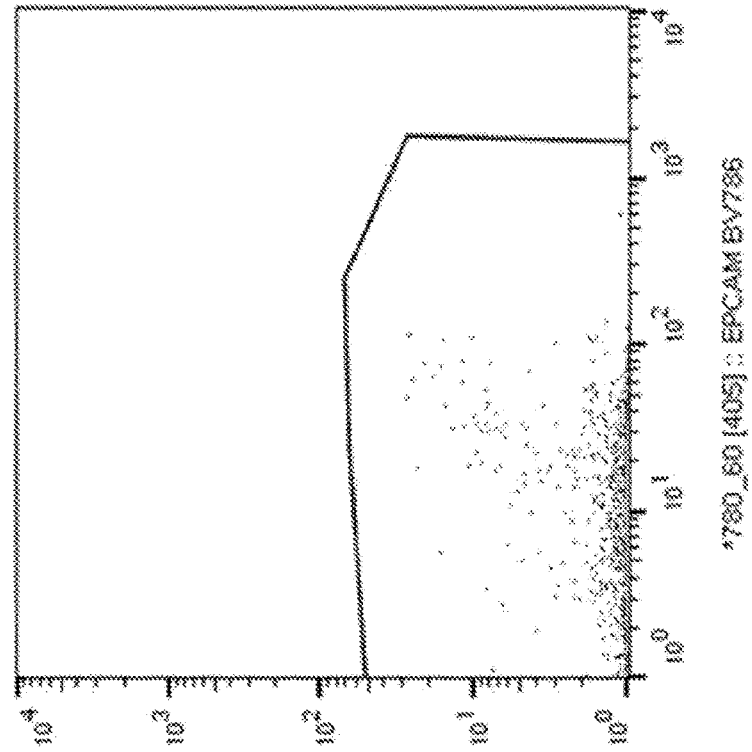
Figure 63:
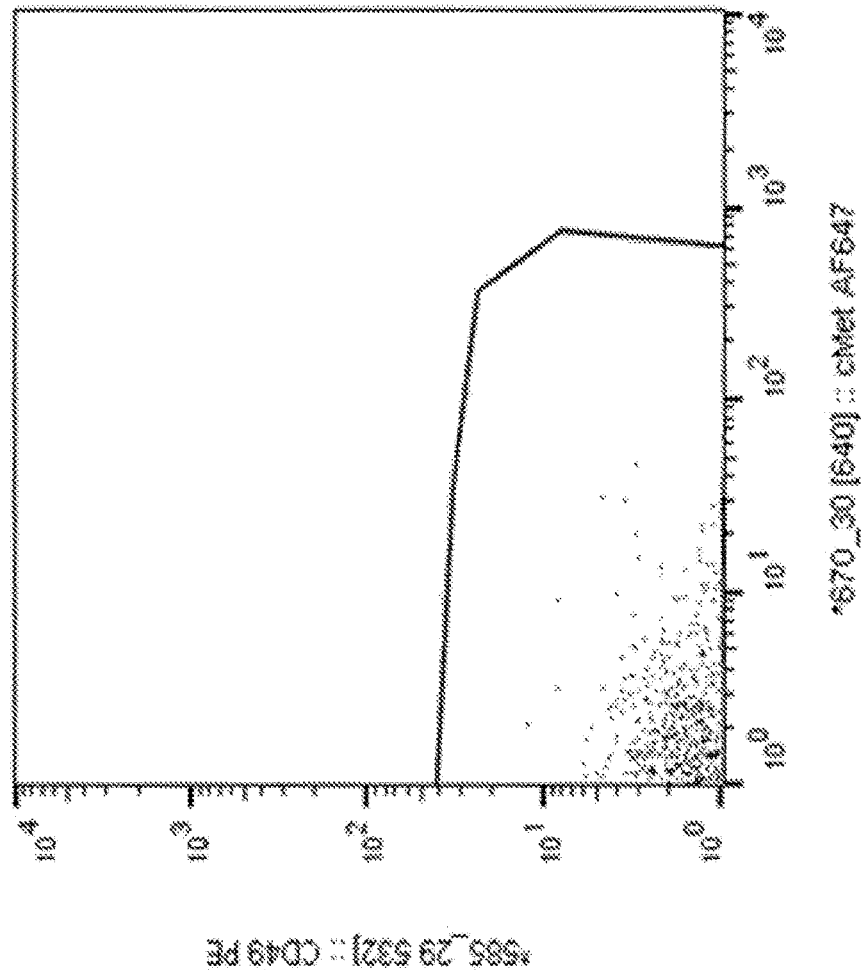

FIG. 63 depicts the results of exemplary experiments demonstrating the background expression of the 8-color DTC panel on bone marrow from a healthy donor.

Figure 64:
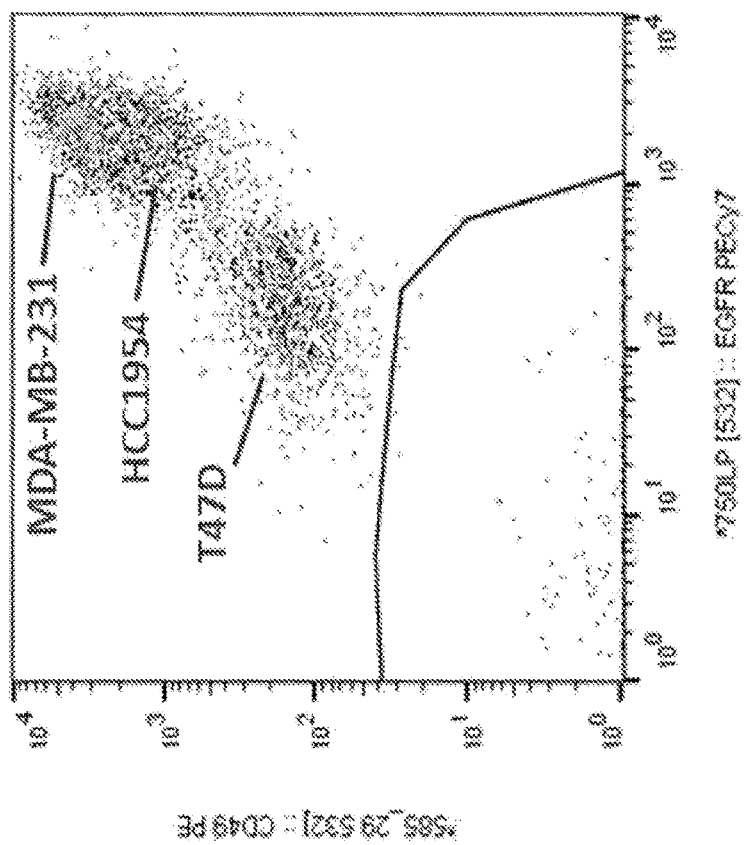
Figure 64:
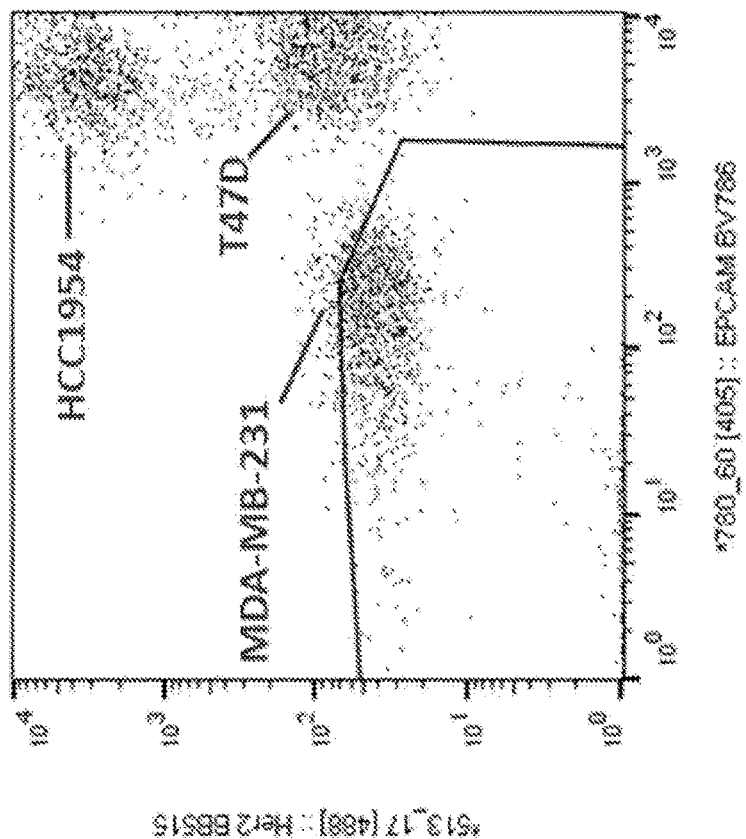
Figure 64:
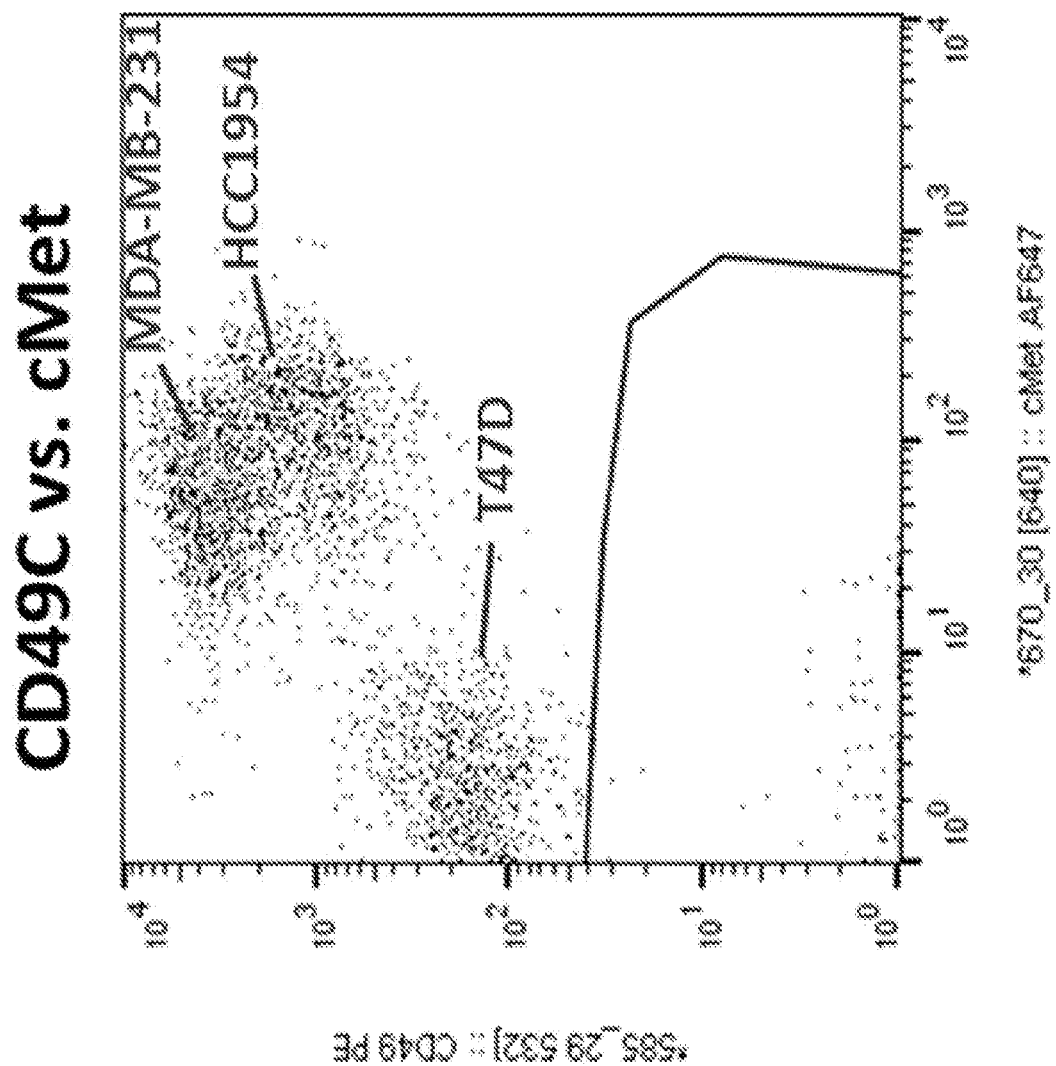

FIG. 64 depicts the results of exemplary experiments demonstrating the use of the 8-color DTC panel to identify breast cancer cells in a spiked sample.

DETAILED DESCRIPTION

In one aspect, the present invention provides compositions for detecting the presence of disseminated tumor cells (DTC) in a sample from a subject. In certain embodiments, the composition of the invention may be used for diagnosing breast cancer or breast cancer risk in the subject.

In one embodiment, the composition comprises at least one labeled molecule, for example, a labeled antibody, for detecting at least one marker expressed by a DTC. In one embodiment, the marker is at least one of HER2, EpCAM, CD49C, EGFR, c-Met, and pan-cytokeratin.

In one embodiment, the composition comprises at least one labeled molecule, for example, a labeled antibody, for detecting a marker that is not expressed by a DTC. In one embodiment, the marker is expressed by a bone marrow cell or a bone marrow progenitor cell. In one embodiment, the marker is at least one of CD43 and CD45.

In one embodiment, the composition comprises a combination of at least two labeled molecules, for example, at least two labeled antibody, for detecting at least one marker expressed by a DTC and at least one marker that is not expressed by a DTC. In one embodiment, the at least two labeled molecules detect at least one of HER2, EpCAM, CD49C, EGFR, c-Met, and pan-cytokeratin and at least one of CD43 and CD45.

In certain embodiments, the present invention provides methods for detecting the presence of a DTC in a sample from a subject. In one embodiment, the method comprises contacting a sample from a subject with a composition for detecting at least one positive or negative selection marker of the invention. In one embodiment, the positive selection marker of the invention is a marker that is expressed on DTCs, whereas the negative selection marker of the invention is a marker that is not expressed in DTCs. In one embodiment, the DTCs are from breast cancer, and the method comprises contacting a sample from a subject with a composition for detecting at least one of HER2, EpCAM, CD49C, EGFR, c-Met and pan-cytokeratin. In one embodiment, the method further comprises contacting the sample with a composition for detecting at least one of CD43 and CD45. In one embodiment, the DTC expresses at least one of HER2, EpCAM, CD49C, EGFR, c-Met and pan-cytokeratin, but does not express at least one of CD43 and CD45.

In certain embodiments, the present invention provides methods for isolating a DTC from a sample from a subject. In one embodiment, the method further comprises analyzing an isolated DTC. For example, in certain embodiments, the method comprises sequencing a nucleic acid molecule or fragment thereof of an isolated DTC.

In certain embodiments, the invention provides methods for treating a subject having, or at risk for developing, a condition associated with the presence of a DTC expressing at least one of HER2, EpCAM, CD49C, EGFR, c-Met and pan-cytokeratin. Exemplary conditions, include, but are not limited to breast cancer and metastatic breast cancer. In one embodiment, the condition is HER2 amplified breast cancer.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

The term "antibody," as used herein, refers to an immunoglobulin molecule that is able to specifically bind to a specific epitope on an antigen. Antibodies can be intact immunoglobulins derived from natural sources or from recombinant sources and can be immunoreactive portions of intact immunoglobulins. The antibodies useful in the present invention may exist in a variety of forms including, for example, polyclonal antibodies, monoclonal antibodies, intracellular antibodies ("intrabodies"), Fv, Fab and F(ab)$_2$, as well as single chain antibodies (scFv), camelid antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, New York; Houston et al., 1988, Proc. Natl. Acad. Sci. USA 85:5879-5883; Bird et al., 1988, Science 242:423-426).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, "aptamer" refers to a small molecule that can bind specifically to another molecule. Aptamers are typically either polynucleotide- or peptide-based molecules. A polynucleotide aptamer is a DNA or RNA molecule that adopts a highly specific three-dimensional conformation designed to have appropriate binding affinities and specificities towards specific target molecules, such as peptides, proteins, drugs, vitamins, among other organic and inorganic molecules. Such polynucleotide aptamers can be selected from a vast population of random sequences through the use of systematic evolution of ligands by exponential enrichment. A peptide aptamer is typically a loop of about 10 to about 20 amino acids attached to a protein scaffold that binds to specific ligands. Peptide aptamers may be identified and isolated from combinatorial libraries, using methods such as the yeast two-hybrid system.

As used herein, "autologous" refers to a biological material derived from the same individual into whom the material will later be re-introduced.

As used herein, "allogeneic" refers to a biological material derived from a genetically different individual of the same species as the individual into whom the material will be introduced.

As used herein, the term "basal medium" refers to a solution of amino acids, vitamins, salts, and nutrients that is effective to support the growth of cells in culture, although normally these compounds will not support cell growth unless supplemented with additional compounds. The nutrients include a carbon source (e.g., a sugar such as glucose) that can be metabolized by the cells, as well as other compounds necessary for the cells' survival. These are compounds that the cells themselves cannot synthesize, due to the absence of one or more of the gene(s) that encode the protein(s) necessary to synthesize the compound (e.g., essential amino acids) or, with respect to compounds which the cells can synthesize, because of their particular developmental state the gene(s) encoding the necessary biosynthetic proteins are not being expressed as sufficient levels. A number of base media are known in the art of mammalian cell culture, such as Dulbecco's Modified Eagle Media (DMEM), Knockout-DMEM (KO-DMEM), and DMEM/F12, although any base medium that supports the growth of stem cells in a substantially undifferentiated state can be employed.

The terms "biomarker" and "marker" are used herein interchangeably. They refer to a substance that is a distinctive indicator of a biological process, biological event and/or pathologic condition, disease or disorder.

The phrase "biological sample" is used herein in its broadest sense. A sample may be of any biological tissue or fluid from which biomarkers of the present invention may be assayed. Examples of such samples include but are not limited to blood, lymph, urine, gynecological fluids, biopsies, amniotic fluid and smears. In one embodiment, a sample is a bone marrow aspirate. Samples may be obtained from a patient by a variety of techniques including, for example, by scraping or swabbing an area or by using a needle to aspirate bodily fluids. Methods for collecting various body samples are well known in the art. Frequently, a sample will be a "clinical sample," i.e., a sample derived from a patient. The sample also encompasses any material derived by processing a biological or body sample. Derived materials include, but are not limited to, cells (or their progeny) isolated from the sample, proteins or nucleic acid molecules extracted from the sample. Processing of a biological or body sample may involve one or more of: filtration, distillation, extraction, concentration, inactivation of interfering components, addition of reagents, and the like.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

The terms "cells" and "population of cells" are used interchangeably and refer to a plurality of cells, i.e., more than one cell. The population may be a pure population comprising one cell type. Alternatively, the population may comprise more than one cell type. In the present invention, there is no limit on the number of cell types that a cell population may comprise.

The term "detecting" or "detection," means assessing the presence, absence, quantity or amount of a given substance (e.g., a DTC or DTC marker) within a clinical or subject-derived sample, including the derivation of qualitative or quantitative levels of such substances, or otherwise evaluating the values or categorization of a subject's clinical parameters.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

An "effective amount" or "therapeutically effective amount" of a compound is that amount of compound which is sufficient to provide a beneficial effect to the subject to which the compound is administered. An "effective amount" of a delivery vehicle is that amount sufficient to effectively bind or deliver a compound.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). The term "nucleic acid" typically refers to large polynucleotides.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

"Parenteral" administration of a composition includes, e.g., subcutaneous (s.c.), intravenous (i.v.), intramuscular (i.m.), or intrasternal injection, or infusion techniques.

As used herein, the terms "peptide," "polypeptide," and "protein" are used interchangeably, and refer to a compound comprising amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Proliferation" is used herein to refer to the reproduction or multiplication of similar forms, especially of cells. That is, proliferation encompasses production of a greater number of cells, and can be measured by, among other things, simply counting the numbers of cells, measuring incorporation of $^3$H-thymidine into the cell, and the like.

By the term "specifically binds," as used herein, is meant a molecule, such as an antibody, which recognizes and binds to another molecule or feature, but does not substantially recognize or bind other molecules or features in a sample.

A "therapeutic" treatment is a treatment administered to a subject who exhibits signs of pathology, for the purpose of diminishing or eliminating those signs.

The phrase "therapeutically effective amount," as used herein, refers to an amount that is sufficient or effective to prevent or treat (delay or prevent the onset of, prevent the progression of, inhibit, decrease or reverse) a disease or condition, including alleviating symptoms of such diseases.

To "treat" a disease as the term is used herein, means to reduce the frequency or severity of at least one sign or symptom of a disease or disorder experienced by a subject.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The invention provides compositions for use in identifying DTCs, methods of analyzing DTCs, and methods of diagnosing and treating breast cancer based on the presence or characteristics of DTCs. The invention is based, in part, on using the compositions in the development of a streamlined assay using flow cytometry and fluorescence-activated cell sorting (FACS) to enable the efficient identification and isolation of DTCs from bone marrow aspirates obtained from breast cancer patients.

Compositions

The present disclosure relates to assays for detecting DTCs in a bone marrow sample from a subject. These assays employ on a combination of detection agents including positive detection agents that selectively or specifically bind breast cancer DTCs and negative detection agents that selectively or specifically bind bone marrow cells. The following is a general, non-limiting description of these agents.

Positive Selection Markers

In one embodiment, the invention provides at least one labeled molecule for detection of at least one antigen expressed by DTCs. In one embodiment, at least 1, 2, 3, 4, 5, 6, 7, 8, 9, 10 or more than 10 labeled molecule detects at least 1, 2, 3, 4, 5, 6, 7, 8, 9, 10 or more than 10 antigen expressed by DTCs. In one embodiment, the at least one labeled molecule detects at least one of HER2, EpCAM, CD49C, EGFR, c-Met and pan-cytokeratin. In one embodiment, at least one labeled molecule detects CD49C. In one embodiment, at least 1, 2, 3, 4, 5, 6 or more than 6 labeled molecule detects at least 1, 2, 3, 4, 5 or each of HER2, EpCAM, CD49C, EGFR, c-Met and pan-cytokeratin.

Negative Selection Markers

In one embodiment, the invention provides at least one labeled molecule for detection of at least one antigen that is not expressed by DTCs. In one embodiment, a negative selection molecule is a molecule expressed by a cell, such as a bone marrow cell or a bone marrow progenitor cell, but is not expressed by a DTC. In one embodiment, at least 1, 2, 3, 4, 5, 6, 7, 8, 9, 10 or more than 10 labeled molecule detects at least 1, 2, 3, 4, 5, 6, 7, 8, 9, 10 or more than 10 antigen that are not expressed by DTCs. In one embodiment, the at least one labeled molecule detects at least one of CD43 and CD45. In one embodiment, the at least one labeled molecule detects CD45.

Combinations of Markers

In one embodiment, the invention provides a combination of labeled molecules for detection of at least one positive and at least one negative selection marker expressed by DTCs. In one embodiment, a combination of at least 1, 2, 3, 4, 5, 6, 7, 8, 9, 10 or more than 10 labeled molecule detects at least 1, 2, 3, 4, 5, 6, 7, 8, 9, 10 or more than 10 positive selection molecules expressed by DTCs and at least 1, 2, 3, 4, 5, 6, 7, 8, 9, 10 or more than 10 negative selection molecules not expressed by DTCs. In one embodiment, a combination of labeled molecules is provided for detection of at least one of HER2, EpCAM, CD49C, EGFR, c-Met and pan-cytokeratin and at least one of CD43 and CD45. In one embodiment, a combination of labeled molecules is provided for detection of HER2, EpCAM, CD49C, EGFR, c-Met, CD43 and CD45.

Other Selections

In one embodiment, at least one labeled molecule for detection of at least one positive or negative selection marker is used in combination with at least one additional selection method. Additional selection methods include, but are not limited to, live/dead staining, cell size selection, cell morphology selection and staining for intracellular markers. Methods for live/dead cell staining are known in the art and include, but are not limited to (4',6-diamidino-2-phenylindole (DAPI) staining, Hoechst 33342 dye, Propidium Iodide (PI), DRAQ7, 7-AAD, TO-PRO-3, live/dead fixable dyes, eFluor fixable dyes, Horizon dyes, Biolegend Zombie dyes and Ghost dyes.

In one embodiment, at least one labeled molecule for detection of at least one positive or negative selection marker is used in combination with a method for detection of at least one additional marker. In one embodiment, additional markers are useful for DTC phenotyping, including, but not limited to, Ki67, pan-cytokeratin and estrogen receptor (ER).

Labeled Molecules

In one embodiment, a labeled molecule specifically binds to a positive or negative selection marker of the invention. Non-limiting examples of molecules capable of specific binding to a positive or negative selection marker include but are not limited to an antibody, aptamer, molecular probe, peptide, peptidomimetic, small molecule, and conjugates thereof.

Antibodies

In one embodiment, the labeled molecule is an antibody that specifically binds to a positive or negative selection marker, sometimes referred herein as an antibody of the invention. Antibodies are capable of "specific binding" to a particular target or series of antigenically related targets. As used herein, an antibody is said to be capable of "specific binding" to an antigen if it discriminates from antigenically distinct molecules based on binding of those molecules to the variable region of the antibody. Such interactions are in contrast to non-specific binding that involve classes of compounds, irrespective of their chemical structure (such as the binding of proteins to nitrocellulose, etc.).

Such antibodies include polyclonal antibodies, monoclonal antibodies, Fab and single chain Fv (scFv) fragments thereof, bispecific antibodies, heteroconjugates, human and humanized antibodies. Such antibodies may be produced in a variety of ways, including hybridoma cultures, recombinant expression in bacteria or mammalian cell cultures, and recombinant expression in transgenic animals. The choice of manufacturing methodology depends on several factors including the antibody structure desired, the importance of carbohydrate moieties on the antibodies, ease of culturing and purification, and cost. Many different antibody structures may be generated using standard expression technology, including full-length antibodies, antibody fragments, such as Fab and Fv fragments, as well as chimeric antibodies comprising components from different species. Antibody fragments of small size, such as Fab and Fv fragments, having no effector functions and limited pharmacokinetic activity may be generated in a bacterial expression system. Single chain Fv fragments show low immunogenicity and are cleared rapidly from the blood.

The antibodies of the present invention may be polyclonal antibodies. Such polyclonal antibodies can be produced in a mammal, for example, following one or more injections of an immunizing agent, and preferably, an adjuvant. Typically, the immunizing agent and/or adjuvant will be injected into the mammal by a series of subcutaneous or intraperitoneal injections. The immunizing agent may include a positive or negative selection marker of the invention or a fragment thereof. Alternatively, a crude protein preparation which has been enriched for a positive or negative selection marker or a fragment thereof can be used to generate antibodies. Such proteins, fragments or preparations are introduced into the non-human mammal in the presence of an appropriate adjuvant. If the serum contains polyclonal antibodies to undesired epitopes, the polyclonal antibodies are purified by immunoaffinity chromatography.

Alternatively, the antibodies may be monoclonal antibodies. Monoclonal antibodies may be produced by hybridomas, wherein a mouse, hamster, or other appropriate host animal, is immunized with an immunizing agent to elicit lymphocytes that produce or are capable of producing antibodies that will specifically bind to the immunizing agent, e.g. Kohler and Milstein, Nature 256:495 (1975). The immunizing agent will typically include a positive or negative selection marker or a fragment thereof and optionally a carrier. Alternatively, lymphocytes may be immunized in vitro. Generally, spleen cells or lymph node cells are used if non-human mammalian sources are desired, or peripheral blood lymphocytes ("PBLs") are used if cells of human origin are desired. The lymphocytes are fused with an immortalized cell line using a suitable fusing agent, such as polyethylene glycol, to produce a hybridoma cell. In general, immortalized cell lines are transformed mammalian cells, for example, myeloma cells of rat, mouse, bovine or human origin. The hybridoma cells are cultured in a suitable culture medium that preferably contains one or more substances that inhibit the growth or survival of unfused, immortalized cells. The culture medium (supernatant) in which the hybridoma cells are cultured can be assayed for the presence of monoclonal antibodies directed against a positive or negative selection marker by conventional techniques, such as by immunoprecipitation or by an in vitro binding assay, such as RIA or ELISA.

The monoclonal antibodies may also be made by recombinant DNA methods, such as those described in U.S. Pat. No. 4,816,567. DNA encoding the monoclonal antibodies of the invention can be isolated from the positive or negative selection marker specific hybridoma cells and sequenced, e.g., by using oligonucleotide probes that are capable of binding specifically to genes encoding the heavy and light chains of murine antibodies. Once isolated, the DNA may be inserted into an expression vector, which is then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for the murine heavy and light chain constant domains for the homologous human sequences, or by covalently joining to the immunoglobulin coding sequence all or part of the coding sequence for a non-immunoglobulin polypeptide. The non-immunoglobulin polypeptide can be substituted for the constant domains of an antibody of the invention, or can be substituted for the variable domains of one antigen-combining site of an antibody of the invention to create a chimeric bivalent antibody.

The antibodies may also be monovalent antibodies. Methods for preparing monovalent antibodies are well known in the art. For example, in vitro methods are suitable for preparing monovalent antibodies. Digestion of antibodies to produce fragments thereof, particularly, Fab fragments, can be accomplished using routine techniques known in the art.

Antibodies and antibody fragments characteristic of hybridomas of the invention can also be produced by recombinant means by extracting messenger RNA, constructing a cDNA library, and selecting clones which encode segments of the antibody molecule.

The antibodies of the invention may further comprise humanized antibodies or human antibodies. The term "humanized antibody" refers to humanized forms of non-human (e.g., murine) antibodies that are chimeric antibodies, immunoglobulin chains or fragments thereof (such as Fv, Fab, Fab', F(ab'), or other antigen-binding partial sequences of antibodies) which contain some portions of the sequence derived from non-human antibodies. Humanized antibodies include human immunoglobulins in which residues from a complementary determining region (CDR) of the human immunoglobulin are replaced by residues from a CDR of a non-human species such as mouse, rat or rabbit having the desired binding specificity, affinity and capacity. In general, the humanized antibody will comprise substantially all of at least one, and generally two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. Methods for humanizing non-human antibodies are well known in the art. Generally, a humanized antibody has one or more amino acids introduced into it from a source which is non-human in order to more closely resemble a human antibody, while still retaining the original binding activity of the antibody.

Heteroconjugate antibodies which comprise two covalently joined antibodies, are also within the scope of the present invention. Heteroconjugate antibodies may be prepared in vitro using known methods in synthetic protein chemistry, including those involving crosslinking agents. For example, immunotoxins may be prepared using a disulfide exchange reaction or by forming a thioether bond.

In one embodiment, the antibodies of the invention are preferably specific for the positive or negative selection marker and so, do not bind peptides derived from other proteins with high affinity. Preferably, monoclonal antibodies, Fv fragments, Fab fragments, or other binding compositions derived from monoclonal antibodies of the invention have a high affinity to a positive or negative selection marker. The affinity of monoclonal antibodies and related molecules to a positive or negative selection marker may be measured by conventional techniques.

In one aspect, the antibodies of the present invention are useful for detecting a positive or negative selection marker. Such detection methods are advantageously applied to diagnosis and/or prognosis of cancer. In one embodiment, antibodies of the invention can be used diagnostically to monitor protein levels in a sample as part of a clinical testing procedure, e.g., to determine the efficacy of a given treatment regimen. Detection can be facilitated by coupling (i.e., physically linking) the antibody to a label group.

Aptamers

In one embodiment, the labeled molecule of the present invention is an aptamer. In one embodiment, the labeled molecule is a protein aptamer. In another embodiment, the labeled molecule is a polynucleotidal aptamer. In one embodiment, the aptamer of the invention is used to detect at least one positive or negative selection marker in a biological sample.

In one embodiment, an aptamer is a nucleic acid or oligonucleotide molecule that binds to a specific molecular target, such as a positive or negative selection marker. In one embodiment, aptamers are obtained from an in vitro evolutionary process known as SELEX (Systematic Evolution of Ligands by EXponential Enrichment), which selects target-specific aptamer sequences from combinatorial libraries of single stranded oligonucleotide templates comprising randomized sequences. In some embodiments, aptamer compositions are double-stranded or single-stranded, and in various embodiments include deoxyribonucleotides, ribonucleotides, nucleotide derivatives, or other nucleotide-like molecules. In some embodiments, the nucleotide components of an aptamer include modified or non-natural nucleotides, for example nucleotides that have modified sugar groups (e.g., the 2'-OH group of a ribonucleotide is replaced by 2'-F or 2'-NH$_2$), which in some instances, improves a desired property, e.g., resistance to nucleases.

Modifications of the nucleic acids contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases isocytidine and isoguanidine and the like. Modifications can also include 3' and 5' modifications such as capping.

In one embodiment, the selection of a nucleic acid ligand specific for a positive or negative selection marker is carried out on a sensor chip surface and monitored by surface plasmon resonance. In one embodiment, aptamers are obtained from the screening of an RNA library. In one example, a combinatorial RNA library is made by transcribing DNA templates or a DNA library. However, in another embodiment, an aptamer is obtained from the screening of an ssDNA library (Chen et al., 2009, PLoS ONE, 4(12): e8142).

Methods of Detecting DTCs

In one embodiment, the invention relates to methods for detecting and isolating DTCs from a sample from a subject.

Samples for analysis using the compositions and methods of the invention may be obtained from an individual or patient. Methods of obtaining test samples are well-known to those of skill in the art and include, but are not limited to aspirations or drawing of blood or other fluids. Samples may include, but are not limited to, blood, lymph, urine, gynecological fluids, biopsies, amniotic fluid and smears. In one embodiment, a sample is a bone marrow aspirate. Samples may be obtained from a patient by a variety of techniques including, for example, by scraping or swabbing an area or by using a needle to aspirate bodily fluids. In some embodiments the sample may be treated or processed by methods known in the art (e.g., centrifugation). In one embodiment, the sample is a bone marrow aspirate.

Variability in sample preparation of cell-containing samples can be corrected by normalizing the data by, for example, protein content or cell number. In certain embodiments, the sample may be normalized relative to the total protein content in the sample. Total protein content in the sample can be determined using standard procedures, including, without limitation, Bradford assay and the Lowry method. In other embodiments, the sample may be normalized relative to cell number.

In one embodiment, the sample is isolated from a subject having or at risk for cancer. In one embodiment, the cancer is breast cancer, however the invention is not limited to detection of a breast cancer DTC. The following are non-limiting examples of cancers that can be diagnosed or treated by the disclosed methods and compositions: acute lymphoblastic leukemia, acute myeloid leukemia, adrenocortical carcinoma, appendix cancer, basal cell carcinoma, bile duct cancer, bladder cancer, bone cancer, brain and spinal cord tumors, brain stem glioma, brain tumor, breast cancer, bronchial tumors, burkitt lymphoma, carcinoid tumor, central nervous system atypical teratoid/rhabdoid tumor, central nervous system embryonal tumors, central nervous system lymphoma, cerebellar astrocytoma, cerebral astrocytoma/malignant glioma, cerebral astrocytotna/malignant glioma, cervical cancer, childhood visual pathway tumor, chordoma, chronic lymphocytic leukemia, chronic myelogenous leukemia, chronic myeloproliferative disorders, colon cancer, colorectal cancer, craniopharyngioma, cutaneous cancer, cutaneous t-cell lymphoma, endometrial cancer, ependymoblastoma, ependymoma, esophageal cancer, ewing family of tumors, extracranial cancer, extragonadal germ cell tumor, extrahepatic bile duct cancer, extrahepatic cancer, eye cancer, fungoides, gallbladder cancer, gastric (stomach) cancer, gastrointestinal cancer, gastrointestinal carcinoid tumor, gastrointestinal stromal tumor (gist), germ cell tumor, gestational cancer, gestational trophoblastic tumor, glioblastoma, glioma, hairy cell leukemia, head and neck cancer, hepatocellular (liver) cancer, histiocytosis, hodgkin lymphoma, hypopharyngeal cancer, hypothalamic and visual pathway glioma, hypothalamic tumor, intraocular (eye) cancer, intraocular melanoma, islet cell tumors, kaposi sarcoma, kidney (renal cell) cancer, langerhans cell cancer, langerhans cell histiocytosis, laryngeal cancer, leukemia, lip and oral cavity cancer, liver cancer, lung cancer, lymphoma, macroglobulinemia, malignant fibrous histiocytoma of bone and osteosarcoma, medulloblastoma, medulloepithelioma, melanoma, merkel cell carcinoma, mesothelioma, metastatic squamous neck cancer with occult primary, mouth cancer, multiple endocrine neoplasia syndrome, multiple myeloma, mycosis, myelodysplastic syndromes, myelodysplastic/myeloproliferative diseases, myelogenous leukemia, myeloid leukemia, myeloma, myeloproliferative disorders, nasal cavity and paranasal sinus cancer, nasopharyngeal cancer, neuroblastoma, non-hodgkin lymphoma, non-small cell lung cancer, oral cancer, oral cavity cancer, oropharyngeal cancer, osteosarcoma and malignant fibrous histiocytoma, osteosarcoma and malignant fibrous histiocytoma of bone, ovarian, ovarian cancer, ovarian epithelial cancer, ovarian germ cell tumor, ovarian low malignant potential tumor, pancreatic cancer, papillomatosis, paraganglioma, parathyroid cancer, penile cancer, pharyngeal cancer, pheochromocytoma, pineal parenchymal tumors of intermediate differentiation, pineoblastoma and supratentorial primitive neuroectodermal tumors, pituitary tumor, plasma cell neoplasm, plasma cell neoplasm/multiple myeloma, pleuropulmonary blastoma, primary central nervous system cancer, primary central nervous system lymphoma, prostate cancer, rectal cancer, renal cell (kidney) cancer, renal pelvis and ureter cancer, respiratory tract carcinoma involving the nut gene on chromosome 15, retinoblastoma, rhabdomyosarcoma, salivary gland cancer, sarcoma, sezary syndrome, skin cancer (melanoma), skin cancer (nonmelanoma), skin carcinoma, small cell lung cancer, small intestine cancer, soft tissue cancer, soft tissue sarcoma, squamous cell carcinoma, squamous neck cancer, stomach (gastric) cancer, supratentorial primitive neuroectodermal tumors, supratentorial primitive neuroectodermal tumors and pineoblastoma, T-cell lymphoma, testicular cancer, throat cancer, thymoma and thymic carcinoma, thyroid cancer, transitional cell cancer, transitional cell cancer of the renal pelvis and ureter, trophoblastic tumor, urethral cancer, uterine cancer, uterine sarcoma, vaginal cancer, visual pathway and hypothalamic glioma, vulvar cancer, waldenstrom macroglobulinemia, and wilms tumor.

Flow Cytometry

In certain embodiments, the methods of detecting the presence of DTCs in a sample from a subject can be performed using a flow cytometer. Flow cytometry comprises a well-known methodology for identifying and distinguishing between different cell types in a non-homogeneous sample. In the flow cytometer, cells, often combined with reagent or buffer solutions, are passed substantially one at a time through one or more sensing regions where each cell is illuminated by one or more energy sources. Generally, each cell within the flow cell interrupts a focused light source wherein the light is scattered and absorbed (or fluoresced), thus establishing a single unique cell interrogation event. Upon such interrogation, light emitted or scattered by a cell may be detected by one or more photodetectors and used for either sorting or analytical purposes.

Alternatively, if the light scattering or emission characteristics of certain cells do not meet certain pre-determined threshold (e.g., trigger) criteria, the data for those cells may not be stored in permanent memory. Either data acquisition or data storage or both may be triggered for a cell when the sensed scattering or emission characteristics meet or surpass the threshold or trigger value.

Fluorescence from various fluorochrome-labelled binding molecules, such as those described elsewhere herein, may be used to detect the presence of DTCs. The characteristics of the detected light that is scattered and emitted from the DTCs as they pass through the sensing region may be used as a basis for automatic sorting decisions within a flow cytometer sorter instrument. In a flow cytometer sorter, the results of the processing or analyses may be used, in real time, to automatically make sort decisions for the sample cells. Typically, the sorting is performed by applying an electrical charge to the fluid stream such that a specifically chosen last attached droplet acquires a known charge just prior to breaking off as a detached droplet. Based upon the acquired charge, the droplet may be deflected to a particular output as it passes through an electric field in the sorting region.

Further, complex gating strategies based on generalized and possibly nested Boolean logical expressions may be employed. Such Boolean logic expressions may utilize "exclusive or" (i.e., XOR) Boolean operators in addition to or instead of the AND, OR and NOT operators previously mentioned in this document. Such Boolean expressions may be pre-defined by a user, prior to beginning flow cytometer sorting. Subsequently, during sorting, a computer may automatically evaluate the Boolean expression with reference to data from each cell that passes through the sensing region. Based on such evaluation, the computer may make a sorting decision for each cell in the time interval between when the cell passes through the sensing region and when it reaches the sorting region. The computer then commands the flow cytometer sorter on how to sort each cell (e.g, whether to sort the cell; in which direction to deflect the cell; by how much to angularly deflect the cell) based on whether the cell expresses the markers indicative of a DTC. The data used in the evaluation may comprise information from multiple wavelengths of emission, such as those produced by multiple fluorescent tags in a sample.

In some embodiments of the invention, DTCs are isolated after identification, thereby separating them from non-DTC cells, using methods familiar to the skilled artisan, such as, for example, FACS.

Methods of Analysis of Isolated DTCs

The invention also provides methods which employ, or analyze, the isolated DTCs of the invention, such as preparation of libraries (including cDNA and differential expression libraries); sequencing, detection of sequence alteration(s) (e.g., genotyping or nucleic acid mutation detection); determining presence or absence of a sequence of interest; gene expression profiling; differential amplification; preparation of an immobilized nucleic acid (which can be a nucleic acid immobilized on a microarray), and characterizing (including detecting and/or quantifying) mutations in the isolated DTCs.

Cell Culture

In one embodiment, isolated DTCs of the invention may be cultured. In one embodiment, culturing of cells is useful for expanding a cell or population of cells to generate a sufficient number of cells for a desired analytical method, for example genomic or expression analysis.

The cells of the present invention, whether grown in suspension or as adherent cell cultures, are grown in contact with culture media.

Culture media used in the present invention preferably comprise a basal medium, optionally supplemented with additional components.

Basal medium is a medium that supplies essential sources of carbon and/or vitamins and/or minerals for the cells. The basal medium is generally free of protein and incapable on its own of supporting self-renewal/symmetrical division of the cells.

Preferably, the suitable cell is isolated from a mammal, more preferably a primate and more preferably still, a human. The cells useful in the methods of the present invention are isolated using methods known in the art. Following isolation, the suitable cells are cultured in a culture medium. Media formulations that support the growth of cells include, but are not limited to, Minimum Essential Medium Eagle, ADC-1, LPM (bovine serum albumin-free), F10 (HAM), F12 (HAM), DCCM1, DCCM2, RPMI 1640, BGJ Medium (with and without Fitton-Jackson Modification), Basal Medium Eagle (BME—with the addition of Earle's salt base), Dulbecco's Modified Eagle Medium (DMEM-without serum), Yamane, IMEM-20, Glasgow Modification Eagle Medium (GMEM), Leibovitz L-15 Medium, McCoy's 5A Medium, Medium M199 (M199E—with Earle's salt base), Medium M199 (M199H—with Hank's salt base), Minimum Essential Medium Eagle (MEM-E—with Earle's salt base), Minimum Essential Medium Eagle (MEM-H—with Hank's salt base) and Minimum Essential Medium Eagle (MEM-NAA with nonessential amino acids), and the like.

It is further recognized that additional components may be added to the culture medium. Such components include, but are not limited to, antibiotics, antimycotics, albumin, growth factors, amino acids, and other components known to the art for the culture of cells. Antibiotics which can be added into the medium include, but are not limited to, penicillin and streptomycin. The concentration of penicillin in the culture medium is about 10 to about 200 units per ml. The concentration of streptomycin in the culture medium is about 10 to about 200 µg/ml. However, the invention should in no way be construed to be limited to any one medium for culturing the cells of the invention. Rather, any media capable of supporting the cells of the invention in tissue culture may be used.

Typical substrates for culture of the cells in all aspects of the invention are culture surfaces recognized in this field as useful for cell culture, and these include surfaces of plastics, metal, composites, though commonly a surface such as a plastic tissue culture plate, widely commercially available, is used. Such plates are often a few centimeters in diameter. For scale up, this type of plate can be used at much larger diameters and many repeat plate units used.

The culture surface may further comprise a cell adhesion protein, usually coated onto the surface. Receptors or other molecules present on the cells bind to the protein or other cell culture substrate and this promotes adhesion to the surface and promotes growth. In certain embodiments, the cultures of the invention are preferably adherent cultures, i.e. the cells are attached to a substrate.

Nucleic Acid Analysis

In some embodiments, the methods of the invention are useful to examine nucleic acid dynamics in isolated or cultured DTCs of the invention. Nucleic acids can be obtained using known techniques. Nucleic acid herein includes DNA molecules, including but not limited to nuclear DNA and mtDNA molecules, and RNA molecules including but not limited to mRNA, rRNA, noncodingRNA (ncRNA), large ncRNA (lncRNA), small nuclear RNA (snRNA), small cytoplasmic RNA (scRNA), small nucleolar RNA (snoRNA), small interfering RNA (siRNA) and microRNA (miRNA) molecules. The nucleic acid can be double-stranded or single-stranded (i.e., a sense or an antisense single strand) and can be complementary to a nucleic acid encoding a polypeptide. The nucleic acid can be naturally occurring nucleic acid molecules (e.g., genomic DNA molecules), synthetic nucleic acid molecules (e.g., recombinant DNA molecules), or nucleic acid molecules derived therefrom (e.g., transcripts made from recombinant DNA molecules).

There are many methods known in the art for the detection of specific nucleic acid sequences and new methods are continually reported. A great many such methods involve the generation of an amplification product. Such methods include, but are not limited to polymerase chain reaction (PCR), reverse transcription, ligase chain reaction, loop mediated isothermal amplification, multiple displacement amplification, and nucleic acid sequence based amplification. In one embodiment, an amplification product is generated during sequencing, for example by a polymerase enzyme during single-molecule sequencing.

In one embodiment, a process for the detection of nucleic acid takes advantage of the polymerase chain reaction (PCR). The PCR process is well known in the art (U.S. Pat. Nos. 4,683,195, 4,683,202, and 4,800,159). To briefly summarize PCR, nucleic acid primers, complementary to opposite strands of a nucleic acid amplification target nucleic acid sequence, are permitted to anneal to the denatured sample. A DNA polymerase (typically heat stable) extends the DNA duplex from the hybridized primer. The process is repeated to amplify the nucleic acid target. If the nucleic acid primers do not hybridize to the sample, then there is no corresponding amplified PCR product.

In PCR, the nucleic acid probe can be labeled with a tag. In one embodiment, the detection of the duplex is done using at least one primer directed to the target nucleic acid. In yet another embodiment of PCR, the detection of the hybridized duplex comprises electrophoretic gel separation followed by dye-based visualization.

Nucleic acid amplification procedures by PCR are well known and are described in U.S. Pat. No. 4,683,202. Briefly, the primers anneal to the target nucleic acid at sites distinct from one another and in an opposite orientation. A primer annealed to the target sequence is extended by the enzymatic action of a heat stable polymerase. The extension product is then denatured from the target sequence by heating, and the process is repeated. Successive cycling of this procedure on both strands provides exponential amplification of the region flanked by the primers.

Amplification is then performed using a PCR-type technique, that is to say the PCR technique or any other related technique. Two primers, complementary to the target nucleic acid sequence are then added to the nucleic acid content along with a polymerase, and the polymerase amplifies the DNA region between the primers.

Stem-loop RT-PCR is a PCR method that is useful in the methods of the invention to amplify and quantify nucleic acid molecules of interest (See Caifu et al., 2005, Nucleic Acids Research 33:e179; Mestdagh et al., 2008, Nucleic Acids Research 36:e143; Varkonyi-Gasic et al., 2011, Methods Mol Biol. 744:145-57). Briefly, the method includes two steps: RT and real-time PCR. First, a stem-loop RT primer is hybridized to a miRNA molecule and then reverse transcribed with a reverse transcriptase. Then, the RT products are quantified using conventional real-time PCR.

The expression "specifically hybridizing in stringent conditions" refers to a hybridizing step in the process of the invention where the oligonucleotide sequences selected as probes or primers are of adequate length and sufficiently unambiguous so as to minimize the amount of non-specific binding that may occur during the amplification. The oligonucleotide probes or primers herein described may be prepared by any suitable methods such as chemical synthesis methods.

Hybridization is typically accomplished by annealing the oligonucleotide probe or primer to the template nucleic acid under conditions of stringency that prevent non-specific binding but permit binding of this template nucleic acid which has a significant level of homology with the probe or primer.

Among the conditions of stringency is the melting temperature (Tm) for the amplification step using the set of primers, which is in the range of about 50° C. to about 95° C. Typical hybridization and washing stringency conditions depend in part on the size (i.e., number of nucleotides in length) of the template nucleic acid or the oligonucleotide probe, the base composition and monovalent and divalent cation concentrations (Ausubel et al., 1994, eds Current Protocols in Molecular Biology).

In one embodiment, the amplifications are real-time amplifications performed using a labeled probe, capable of specifically hybridizing in stringent conditions with a segment of a nucleic acid sequence, or polymorphic nucleic acid sequence. The labeled probe is capable of emitting a detectable signal every time each amplification cycle occurs.

The real-time amplification, such as real-time PCR, is well known in the art, and the various known techniques will be employed in the best way for the implementation of the present process. These techniques are performed using various categories of probes, such as hydrolysis probes, hybridization adjacent probes, or molecular beacons. The techniques employing hydrolysis probes or molecular beacons are based on the use of a fluorescence quencher/reporter system, and the hybridization adjacent probes are based on the use of fluorescence acceptor/donor molecules.

Hydrolysis probes with a fluorescence quencher/reporter system are available in the market, and are for example commercialized by the Applied Biosystems group (USA). Many fluorescent dyes may be employed, such as FAM dyes (6-carboxy-fluorescein), or any other dye phosphoramidite reagents.

Among the stringent conditions applied for any one of the hydrolysis-probes of the present invention is the Tm, which is in the range of about 50° C. to 95° C. In one embodiment, the Tm for a hydrolysis-probes is in the range of about 55° C. to about 80° C. In one embodiment, the Tm applied for a hydrolysis-probe is about 75° C.

In one embodiment, the method includes determining the sequence of the nucleic acid molecules. Direct sequence analysis can be used to determine the sequence of the nucleic acid molecules of interest. A sample comprising nucleic acid can be used, and PCR or other appropriate methods can be used to amplify all or a fragment of the nucleic acid, and/or its flanking sequences, if desired.

In one embodiment, the nucleic acid may be prepared (e.g., library preparation) for massively parallel sequencing in any manner as would be understood by those having ordinary skill in the art. Current methods for library preparation attempt to uniformly sample all sequences across every nucleic acid molecule, optimally with sufficient overlap to allow reassembly of the sequences from which they derive, or alternatively, to allow inference of the sequence by alignment with reference sequences. These methods are generally known in the art and generally relate to generating multiple copies of (amplifying) the complementary sequence of the nucleic acid sequences of interest. These standard methods have in common that the libraries of sequences that they contain correspond to the sequences of genes, or in various embodiments, from the messenger RNAs (i.e., mRNAs) transcribed from genes. In one embodiment, the libraries include RNA sequences from DNA regions that are not necessarily considered to be genes, including but not limited to microRNAs, short interfering RNAs, long non-coding RNAs, and others. Similar libraries contain sequences directly obtained from DNA, including but not limited to genomic DNA, organelle DNA and mitochondrial DNA.

While there are many variations of library preparation, the purpose is to construct nucleic acid fragments of a suitable size for a sequencing instrument and to modify the ends of the sample nucleic acid to work with the chemistry of a selected sequencing process. Depending on application, nucleic acid fragments may be generated having a length of about 100-1000 bases. It should be appreciated that the present invention can accommodate any nucleic acid fragment size range that can be generated by a sequencer. This can be achieved by capping the ends of the fragments with nucleic acid adapters. These adapters have multiple roles: first to allow attachment of the specimen strands to a substrate (bead or slide) and second have nucleic acid sequence that can be used to initiate the sequencing reaction (priming). In many cases, these adapters also contain unique sequences (bar-coding) that allow for identification of individual samples in a multiplexed run. The key component of this attachment process is that only one nucleic acid fragment is attached to a bead or location on a slide. This single fragment can then be amplified, such as by a PCR reaction, to generate hundreds of identical copies of itself in a clustered region (bead or slide location).

In one embodiment, barcodes are attached to nucleic acid molecules by primed synthesis in which the barcode is attached to the randomized or partially randomized primer, and the subsequent preparation of the resulting barcoded nucleic acid molecules for sequencing. Such a method is useful, for example, when multiple samples are grouped or pooled for a single sequencing analysis. In one embodiment, the attached barcodes are used to infer or deduce the sequences of the single sample from which they derive.

In one embodiment, clusters of identical nucleic acid molecules form a product that is sequenced. The sequencing can be performed using any standard sequencing method or platform, as would be understood by those having ordinary skill in the art. Representative sequencing methods that can be used in the method of the invention include, but are not limited to direct manual sequencing (Church and Gilbert, 1988, Proc Natl Acad Sci U.S.A., 81:1991-1995; Sanger et al., 1977, Proc Natl Acad Sci U.S.A., 74:5463-5467; Beavis et al. U.S. Pat. No. 5,288,644); automated fluorescent sequencing; single-stranded conformation polymorphism assays (SSCP); clamped denaturing gel electrophoresis (CDGE); denaturing gradient gel electrophoresis (DGGE) (Sheffield et al., 1981, Proc Natl Acad Sci U.S.A., 86:232-236), mobility shift analysis (Orita et al., 1989, Proc Natl Acad Sci U.S.A., 86:2766-2770; Rosenbaum and Reissner, 1987, Biophys. Chem, 265:1275; Keen et al., 1991, Trends Genet, 7:5); RNase protection assays (Myers, et al., 1985, Science, 230:1242); Luminex xMAP™ technology; HTS (Gundry and Vijg, 2011, Mutat Res, doi:10.1016/j.mrfmmm.2011.10.001); NGS (Voelkerding et al., 2009, Clinical Chemistry, 55:641-658; Su et al., 2011, Expert Rev Mol Diagn, 11:333-343; Ji and Myllykangas, 2011, Biotechnol Genet Eng Rev, 27:135-158); and/or ion semiconductor sequencing (Rusk, 2011, Nature Methods, doi:10.1038/nmeth.f 330; Rothberg et al., 2011, Nature, 475:348-352). Next-gen sequencing platforms including, but not limited to, Illumina HiSeq, Illumina MiSeq, Life Technologies PGM, Pacific biosciences RSII and Helicos Heliscope can be used in the method of the invention for sequencing the nucleic acid molecules. These and other methods, alone or in combination, can be used to detect and quantify at least one nucleic acid molecule of interest.

The probes and primers according to the invention can be labeled directly or indirectly with a radioactive or nonradioactive compound, by methods well known to those skilled in the art, in order to obtain a detectable and/or quantifiable signal; the labeling of the primers or of the probes according to the invention is carried out with radioactive elements or with nonradioactive molecules. Among the radioactive isotopes used, mention may be made of $^{32}P$, $^{33}P$, $^{35}S$ or $^{3}H$. The nonradioactive entities are selected from ligands such as biotin, avidin, streptavidin or digoxigenin, haptens, dyes, and luminescent agents such as radioluminescent, chemiluminescent, bioluminescent, fluorescent or phosphorescent agents.

In one embodiment, the sequencing is single-molecule sequencing which allows complete genomes to be sequenced on a single microarray chip in a single sequencing reaction. The principle of this technology is that large numbers of short sequences are immobilized as single strands on a surface where they can be individually visualized with a sensitive microscope and camera. Every fragment is then sequenced simultaneously with fluorescent nucleotides and a polymerase enzyme, and the sequence information from all of the molecules is recorded simultaneously within a single camera frame.

Protein Analysis

In some embodiments, the methods of the invention include examining protein expression or dynamics in isolated or cultured DTCs of the invention. To determine the protein expression or dynamics in the DTCs, any bioassay can be used that determines the level or concentration of at least one protein or biomarker. For example, one or more specific binding agents can be used to analyze and determine the presence or absence of at least one protein or biomarker in a sample. The biological sample is contacted with one or more agents that bind to the biomarker to determine the concentration or level of expression of the at least one protein or biomarker in the sample. One or more of the agents may be also operably linked to a detectable label. Immunoassay methods are suitable in this regard and may be carried out in any of a wide variety of formats. Immunological assay methods generally involve a reagent capable of specifically binding a marker. Suitable immunologic methods include, but are not limited to, immunoprecipitation, particle immunoassay, immunonephelometry, radioimmunoassay (RIA), enzyme immunoassay (EIA) including enzyme-linked immunosorbent assay (ELISA), sandwich, direct, indirect, or competitive ELISA assays, enzyme-linked immunospot assays (ELISPOT), multiplex ELISA array, fluorescent immunoassay (FIA), chemiluminescent immunoassay, flow cytometry assays, immunohistochemistry, Western blot, integrated blood barcode chip and protein-chip assays using for example antibodies, antibody fragments, receptors, ligands, or other agents binding the at least one protein or biomarker.

Generally, any method that can detect or quantify biomarkers in a sample can be used in the methods. These methods include physical and molecular biology methods in addition to immunological methods. For example, suitable physical methods include mass spectrometric methods, fluorescence resonance energy transfer (FRET) assays, chromatographic assays, and dye-detection assays. Suitable molecular biology methods that can be used include, but are not limited to, Northern or Southern blot hybridization, nucleic acid dot-or slot-blot hybridization, in situ hybridization, nucleic acid chip assays, PCR, reverse transcriptase PCR (RT-PCR), or real time PCR (taq-man PCR). Other methods to detect biomarkers include, e.g., nuclear magnetic resonance (NMR), fluorometry, colorimetry, radiometry, luminometry, or other spectrometric methods, plasmon-resonance (e.g. BIACORE), and one-or two-dimensional gel electrophoresis.

In one embodiment, once measured, the concentration of each biomarker and that of any other additional biomarker being assessed is compared to a predetermined reference value for the specific biomarker. The reference value may be determined in one of several ways. For example, the marker reference value can be the marker concentration measured in a sample taken from a control subject, or may be the median marker concentration calculated from the concentrations measured in multiple control samples taken from a group of control subjects.

Treatment Methods

In one embodiment, the invention provides a method of treating a disease or disorder associated with the presence of DTCs in a bone marrow sample in a subject. In one embodiment, a disease or disorder associated with DTCs in a bone marrow sample is breast cancer or metastatic breast cancer. In one embodiment, the method of treatment is determined based on at least one characteristic of an isolated DTC (e.g., an identified genomic mutation).

Therefore, in one embodiment, the invention provides methods of treating or preventing cancer, or of treating and preventing metastasis of tumors in a subject in need thereof. Related aspects of the invention provide methods of preventing, aiding in the prevention, and/or reducing metastasis of hyperplastic or tumor cells in an individual.

In some embodiments of the methods for treating, preventing or inhibiting metastasis in an individual in need thereof, an anti-tumor agent is administered to the individual, such as an antineoplastic agent. In some embodiments, the agent comprises a metastasis-inhibiting agent, such as a plasminogen antagonist, or an adenosine deaminase antagonist. In other embodiments, the agent is an angiogenesis inhibiting agent.

The disclosed compounds can be used to prevent, abate, minimize, control, and/or lessen tumor growth, progression or metastasis in humans and animals. The disclosed compounds can also be used to slow the rate of primary tumor growth. The disclosed compounds when administered to a subject in need of treatment can be used to stop the spread of cancer cells. As such, the compounds disclosed herein can be administered as part of a combination therapy with one or more drugs or other pharmaceutical agents. When used as part of the combination therapy, the decrease in metastasis and reduction in primary tumor growth afforded by the disclosed compounds allows for a more effective and efficient use of any pharmaceutical or drug therapy being used to treat the patient. In addition, control of metastasis by the disclosed compound affords the subject a greater ability to concentrate the disease in one location.

In one embodiment, the invention provides methods for preventing metastasis of malignant tumors or other cancerous cells as well as to reduce the rate of tumor growth. The methods comprise administering an effective amount of one or more of the disclosed compounds to a subject diagnosed with a malignant tumor or cancerous cells or to a subject having a tumor or cancerous cells. In one embodiment, the cancer is breast cancer or metastatic breast cancer.

In one embodiment, the invention provides a method to treat breast cancer or breast cancer metastasis comprising treating a subject identified as having DTCs with a therapy for the cancer, such as surgery, chemotherapy, chemotherapeutic agent, radiation therapy, or hormonal therapy or a combination thereof.

Chemotherapeutic agents include cytotoxic agents (e.g., 5-fluorouracil, cisplatin, carboplatin, methotrexate, daunorubicin, doxorubicin, vincristine, vinblastine, oxorubicin, carmustine (BCNU), lomustine (CCNU), cytarabine USP, cyclophosphamide, estramucine phosphate sodium, altretamine, hydroxyurea, ifosfamide, procarbazine, mitomycin, busulfan, cyclophosphamide, mitoxantrone, carboplatin, cisplatin, interferon alfa-2a recombinant, paclitaxel, teniposide, and streptozoci), cytotoxic alkylating agents (e.g., busulfan, chlorambucil, cyclophosphamide, melphalan, or ethylsulfonic acid), alkylating agents (e.g., asaley, AZQ, BCNU, busulfan, bisulphan, carboxyphthalatoplatinum, CBDCA, CCNU, CHIP, chlorambucil, chlorozotocin, cisplatinum, clomesone, cyanomorpholinodoxorubicin, cyclodisone, cyclophosphamide, dianhydrogalactitol, fluorodopan, hepsulfam, hycanthone, iphosphamide, melphalan, methyl CCNU, mitomycin C, mitozolamide, nitrogen mustard, PCNU, piperazine, piperazinedione, pipobroman, porfiromycin, spirohydantoin mustard, streptozotocin, teroxirone, tetraplatin, thiotepa, triethylenemelamine, uracil nitrogen mustard, and Yoshi-864), antimitotic agents (e.g., allocolchicine, Halichondrin M, colchicine, colchicine derivatives, dolastatin 10, maytansine, rhizoxin, paclitaxel derivatives, paclitaxel, thiocolchicine, trityl cysteine, vinblastine sulfate, and vincristine sulfate), plant alkaloids (e.g., actinomycin D, bleomycin, L-asparaginase, idarubicin, vinblastine sulfate, vincristine sulfate, mitramycin, mitomycin, daunorubicin, VP-16-213, VM-26, navelbine and taxotere), biologicals (e.g., alpha interferon, BCG, G-CSF, GM-CSF, and interleukin-2), topoisomerase I inhibitors (e.g., camptothecin, camptothecin derivatives, and morpholinodoxorubicin), topoisomerase II inhibitors (e.g., mitoxantron, amonafide, m-AMSA, anthrapyrazole derivatives, pyrazoloacridine, bisantrene HCL, daunorubicin, deoxydoxorubicin, menogaril, N,N-dibenzyl daunomycin, oxanthrazole, rubidazone, VM-26 and VP-16), and synthetics (e.g., hydroxyurea, procarbazine, o,p'-DDD, dacarbazine, CCNU, BCNU, cis-diaminedichloroplatinum, mitoxantrone, CBDCA, levamisole, hexamethylmelamine, all-trans retinoic acid, gliadel and porfimer sodium).

Antiproliferative agents are compounds that decrease the proliferation of cells. Antiproliferative agents include alkylating agents, antimetabolites, enzymes, biological response modifiers, miscellaneous agents, hormones and antagonists, androgen inhibitors (e.g., flutamide and leuprolide acetate), antiestrogens (e.g., tamoxifen citrate and analogs thereof, toremifene, droloxifene and roloxifene), Additional examples of specific antiproliferative agents include, but are not limited to levamisole, gallium nitrate, granisetron, sargramostim strontium-89 chloride, filgrastim, pilocarpine, dexrazoxane, and ondansetron.

Other anti-tumor agents include cytotoxic/antineoplastic agents and anti-angiogenic agents. Cytotoxic/anti-neoplastic agents are defined as agents which attack and kill cancer cells. Some cytotoxic/anti-neoplastic agents are alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacarbazine. Other cytotoxic/anti-neoplastic agents are antimetabolites for tumor cells, e.g., cytosine arabinoside, fluorouracil, methotrexate, mercaptopurine, azathioprine, and procarbazine. Other cytotoxic/anti-neoplastic agents are antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents are mitotic inhibitors (vinca alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents are well known to those of skill in the art. Suitable anti-angiogenic agents for use in the methods and compositions of the present disclosure include anti-VEGF antibodies, including humanized and chimeric antibodies, anti-VEGF aptamers and antisense oligonucleotides. Other known inhibitors of angiogenesis include angiostatin, endostatin, interferons, interleukin 1 (including alpha and beta) interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

Other anti-cancer agents that can be used include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1, interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate;

melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RH retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin;

sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. In one embodiment, the anti-cancer drug is 5-fluorouracil, taxol, or leucovorin.

The compositions of the invention may be administered to a patient or subject in need thereof in a wide variety of ways. Modes of administration include intraoperatively intravenous, intravascular, intramuscular, subcutaneous, intracerebral, intraperitoneal, soft tissue injection, surgical placement, arthroscopic placement, and percutaneous insertion, e.g., direct injection, cannulation or catheterization. Any administration may be a single application of a composition of invention or multiple applications. Administrations may be to single site or to more than one site in the individual to be treated. Multiple administrations may occur essentially at the same time or separated in time.

Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions of the present invention may be administered in a manner appropriate to the disease to be treated (or prevented). The quantity and frequency of administration will be determined by such factors as the condition of the subject, and the type and severity of the subject's disease, although appropriate dosages may be determined by clinical trials.

When "therapeutic amount" is indicated, the precise amount of the compositions of the present invention to be administered can be determined by a physician with consideration of individual differences in age, weight, disease type, extent of disease, and condition of the patient (subject).

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the compositions of the present invention are administered to a patient by intradermal or subcutaneous injection. In another embodiment, the compositions of the present invention are preferably administered by i.v. injection.

Kits

The present invention also pertains to kits useful in the methods of the invention. Such kits comprise various combinations of components useful in any of the methods described elsewhere herein, including for example, at least one labeled molecules for detecting at least one positive or negative selection marker of the invention. In one embodiment, the kit comprises at least two labeled molecules for detecting at least one positive selection marker and at least one negative selection marker. In one embodiment, the kit comprises other components e.g., control molecules and instructional material.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out exemplary embodiments of the present invention, and are not to be construed as limiting in any way the remainder of the disclosure.

Example 1

DTC Staining Panel: EpCAM and HER2

A streamlined assay using flow cytometry and fluorescence-activated cell sorting (FACS) to enable the efficient identification and isolation of DTCs from bone marrow aspirates obtained from breast cancer patients. This invention is FACS-based assay incorporating the use of a pre-enrichment device which functions in-line with the cell sorter, as described in U.S. Pat. No. 8,956,536, and provides depletion of non-DTC hematopoietic cells as well as removal of lysed red blood cells, debris, and unbound antibodies. Use of the pre-enrichment device minimizes bone marrow sample handling, thus reducing manual labor and minimizing DTC loss. Pre-enrichment of the bone marrow samples is necessary for detection (and cell sorting) of rare bone marrow DTCs, which may be present at a frequency of 1 DTC per 1 million nucleated bone marrow cells, or less. Then the sample directly enters the BD Influx™ cell sorter, which detects the presence/absence of various DTC and hematopoietic cell surface marker proteins (detected using a panel of fluorochrome-conjugated antibodies) and enables the sorting of selected DTC populations into collection tubes for further biological characterization (genomic/transcriptomic analysis or imaging).

The results of the experiments are now described.

Assessment of Labeling of Human Breast Cancer Cell Lines

Figure 1:
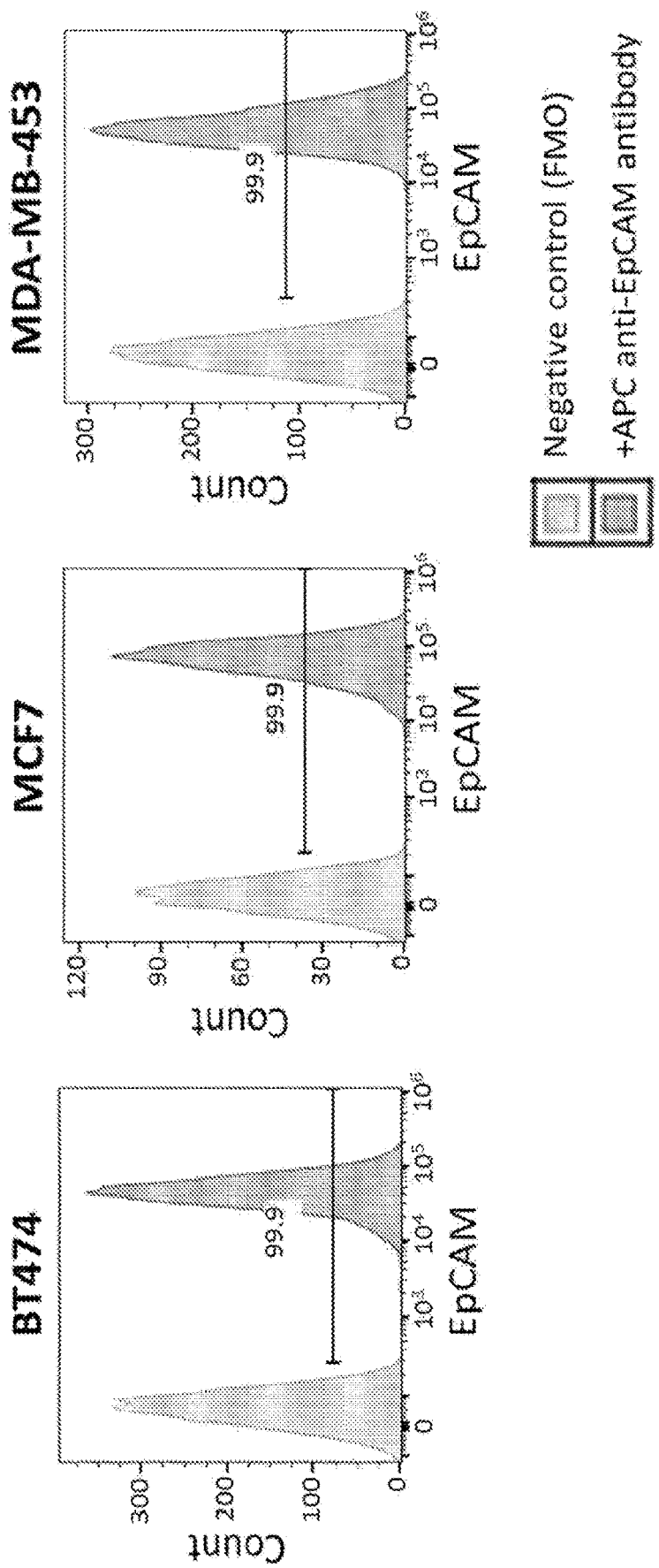
FIG. 1 depicts the results of exemplary experiments demonstrating EpCAM labeling of human breast cancer cell (BCC) lines (luminal). Luminal BCC lines were stained with an anti-EpCAM antibody conjugated to the fluorochrome APC. The experiment was gated for DAPI⁻ (viable) cells. Histograms show APC-EpCAM fluorescence intensity, as determined using an Attune NxT acoustic focusing flow cytometer, compared to "fluorescence-minus-one" (FMO) negative controls, in which the APC anti-EpCAM antibody was omitted from the staining reaction. Data analysis was performed using FlowJo analysis software.
Figure 2:
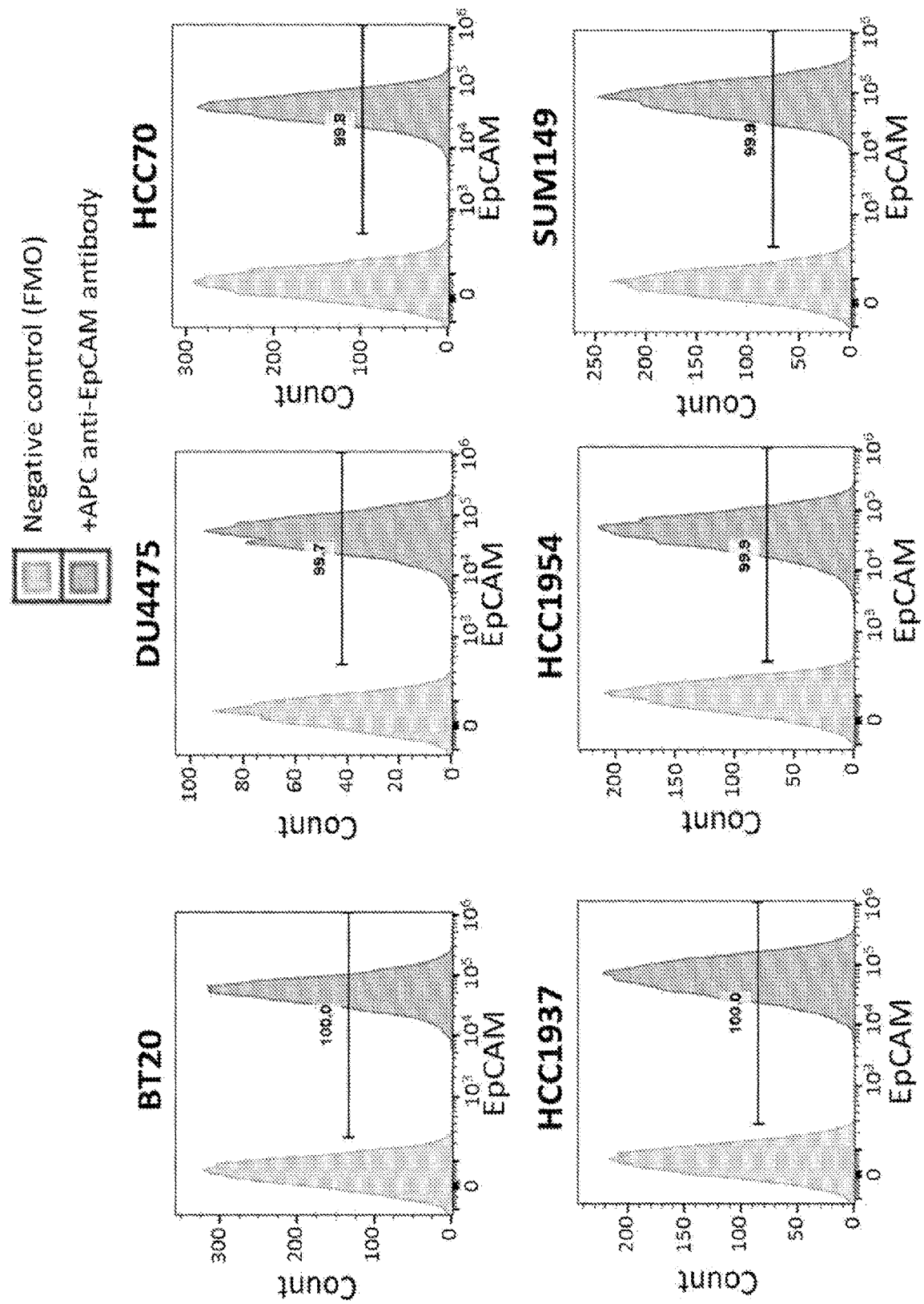
FIG. 2 depicts the results of exemplary experiments demonstrating EpCAM labeling of human BCC lines (basal). Basal BCC lines were stained with an anti-EpCAM antibody conjugated to the fluorochrome APC. The experiment was gated for DAPI⁻ (viable) cells. Histograms show APC-EpCAM fluorescence intensity, as determined using an Attune NxT acoustic focusing flow cytometer, compared to "fluorescence-minus-one" (FMO) negative controls, in which the APC anti-EpCAM antibody was omitted from the staining reaction. Data analysis was performed using FlowJo analysis software.
Figure 3:
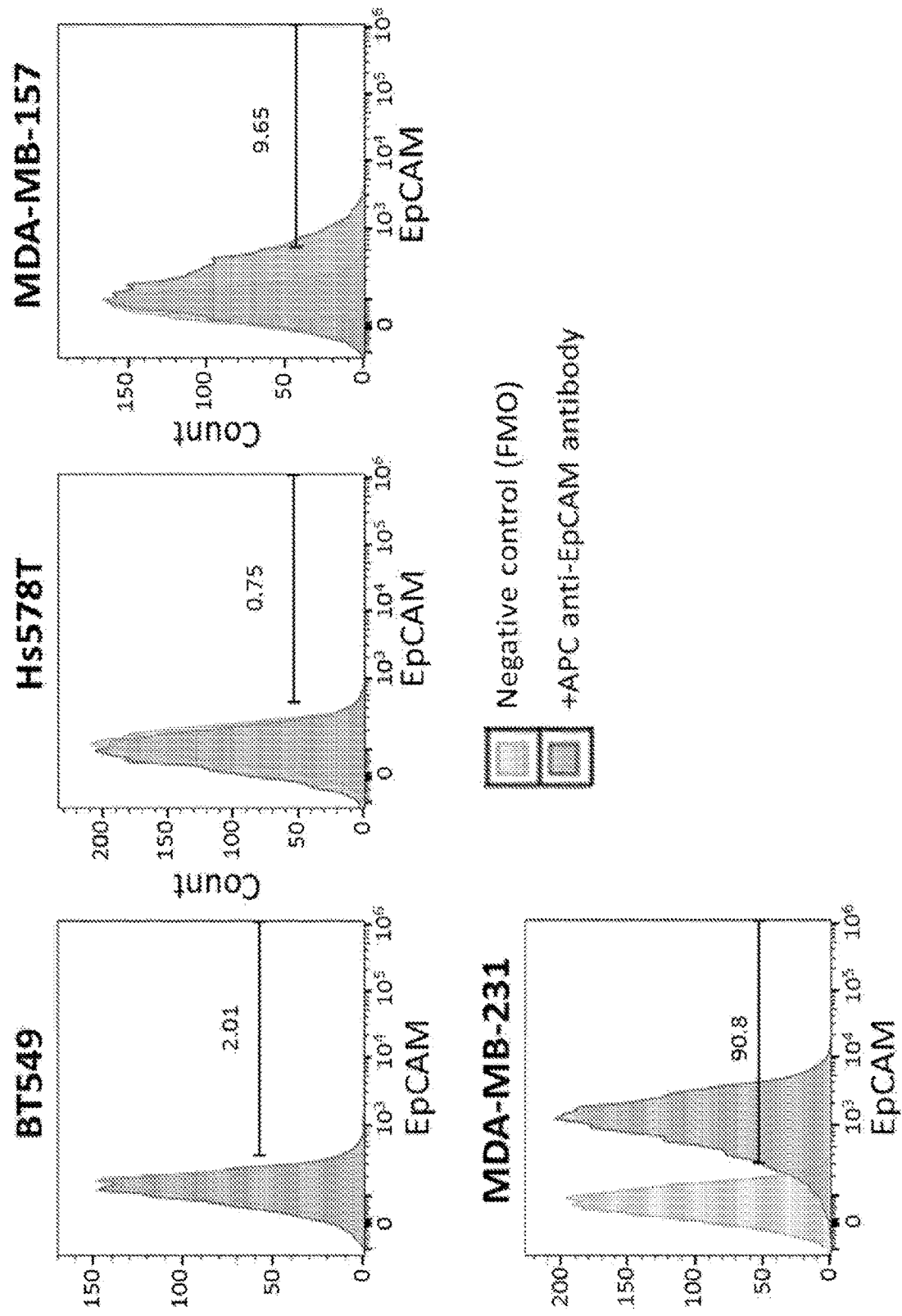
FIG. 3 depicts the results of exemplary experiments demonstrating EpCAM does not label claudin-low BCC lines. Four claudin-low BCC lines were stained with an anti-EpCAM antibody conjugated to the fluorochrome APC, but only one BCC line showed clear EpCAM staining. The experiment was gated for DAPI⁻ (viable) cells. Histograms show APC-EpCAM fluorescence intensity, as determined using an Attune NxT acoustic focusing flow cytometer, compared to "fluorescence-minus-one" (FMO) negative controls, in which the APC anti-EpCAM antibody was omitted from the staining reaction. Data analysis was performed using FlowJo analysis software.
Figure 4:
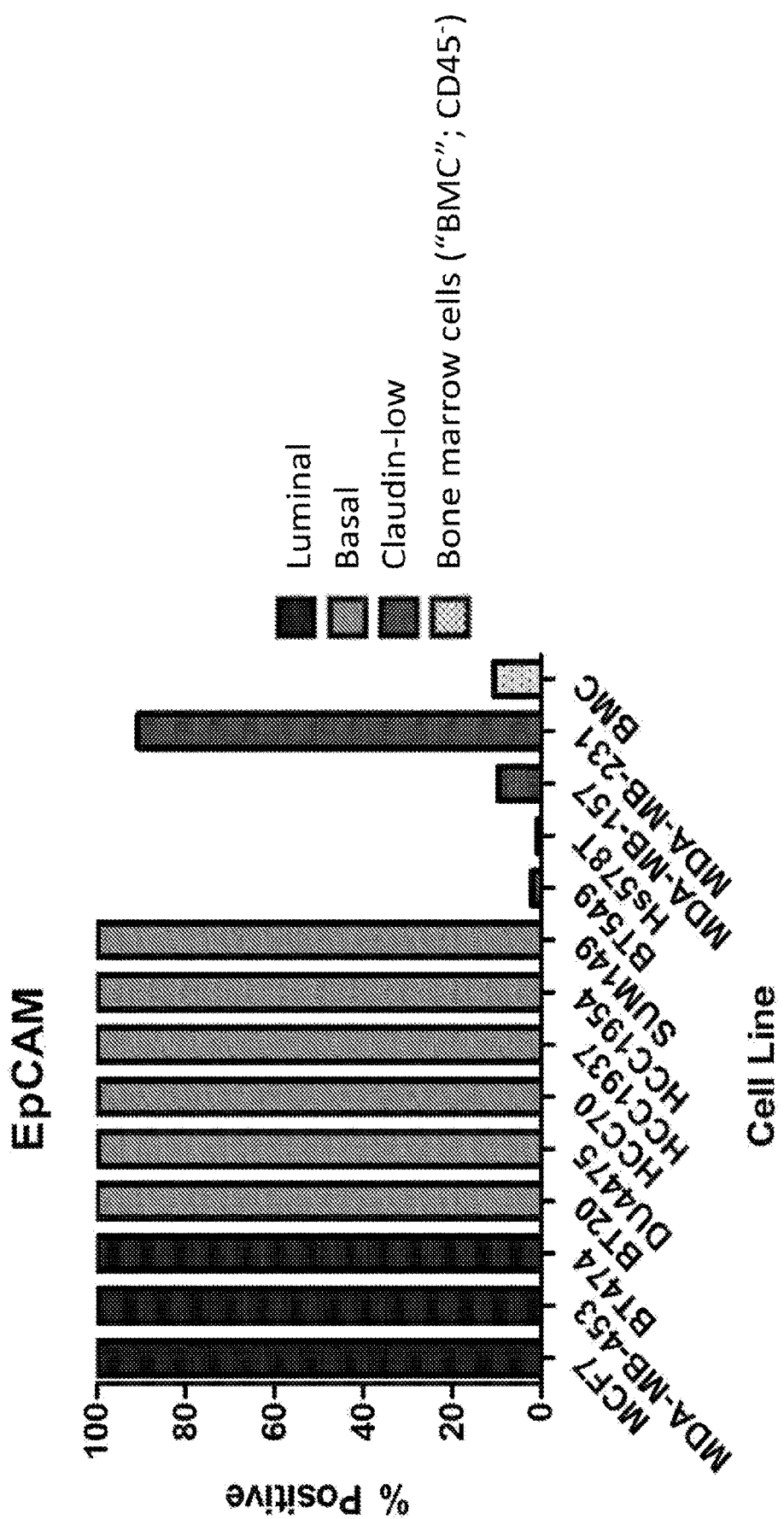
FIG. 4 depicts a summary of the results of exemplary experiments presented in FIG. 1 through FIG. 3 demonstrating the percentage of positive EpCAM labeling of human breast cancer cell lines.
Figure 5:
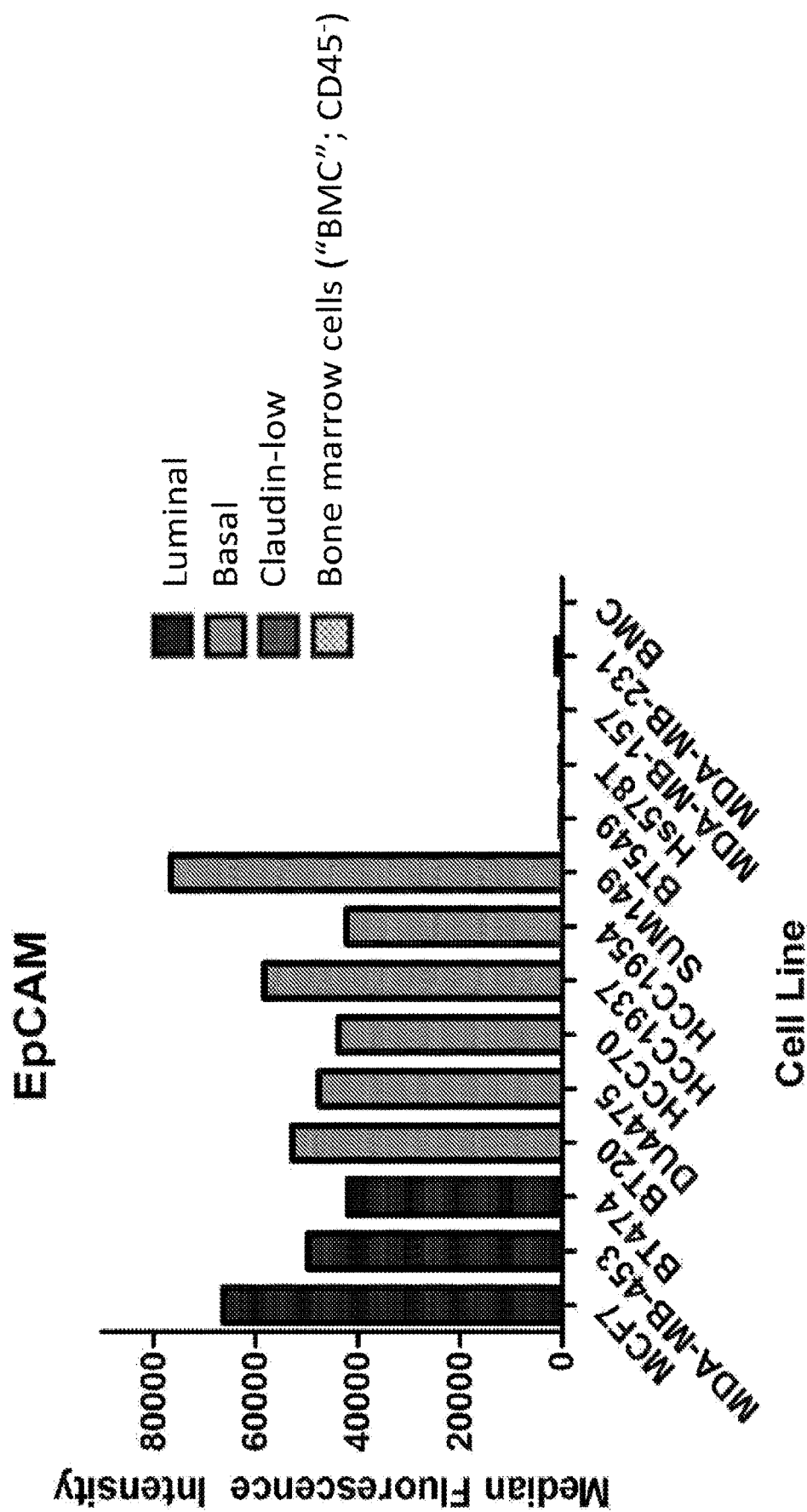
FIG. 5 depicts a summary of the results of exemplary experiments presented in FIG. 1 through FIG. 3 demonstrating the median fluorescence intensity of EpCAM labeled cells for different human breast cancer cell lines.

EpCAM staining alone was tested for the ability to effectively label human breast cancer cell (BCC) lines representing different breast cancer subtypes (i luminal, basal, and claudin-low). FIG. 1 demonstrates that EpCAM effectively labels the tested luminal breast cancer cell lines (≥99.9% of cells in each of these cell lines are EpCAM-positive). FIG. 2 demonstrates that EpCAM also effectively labels the tested basal breast cancer cell lines (≥99% of cells in each of these cell lines are EpCAM-positive). In contrast to luminal and basal human breast cancer cell lines, claudin-low cell lines are not effectively labeled using EpCAM staining (FIG. 3). A low percentage of most claudin-low cell lines are EpCAM-positive, and cells which are EpCAM-positive display lower EpCAM fluorescence intensities compared to either luminal or basal cell lines. EpCAM staining detects a high percentage of luminal and basal breast cancer cell lines. However, few claudin-low cell lines are detected by EpCAM staining alone (FIG. 4). Claudin-low breast cancer cell lines have lower cell surface EpCAM levels than luminal or basal cell lines (FIG. 5).

Figure 6:
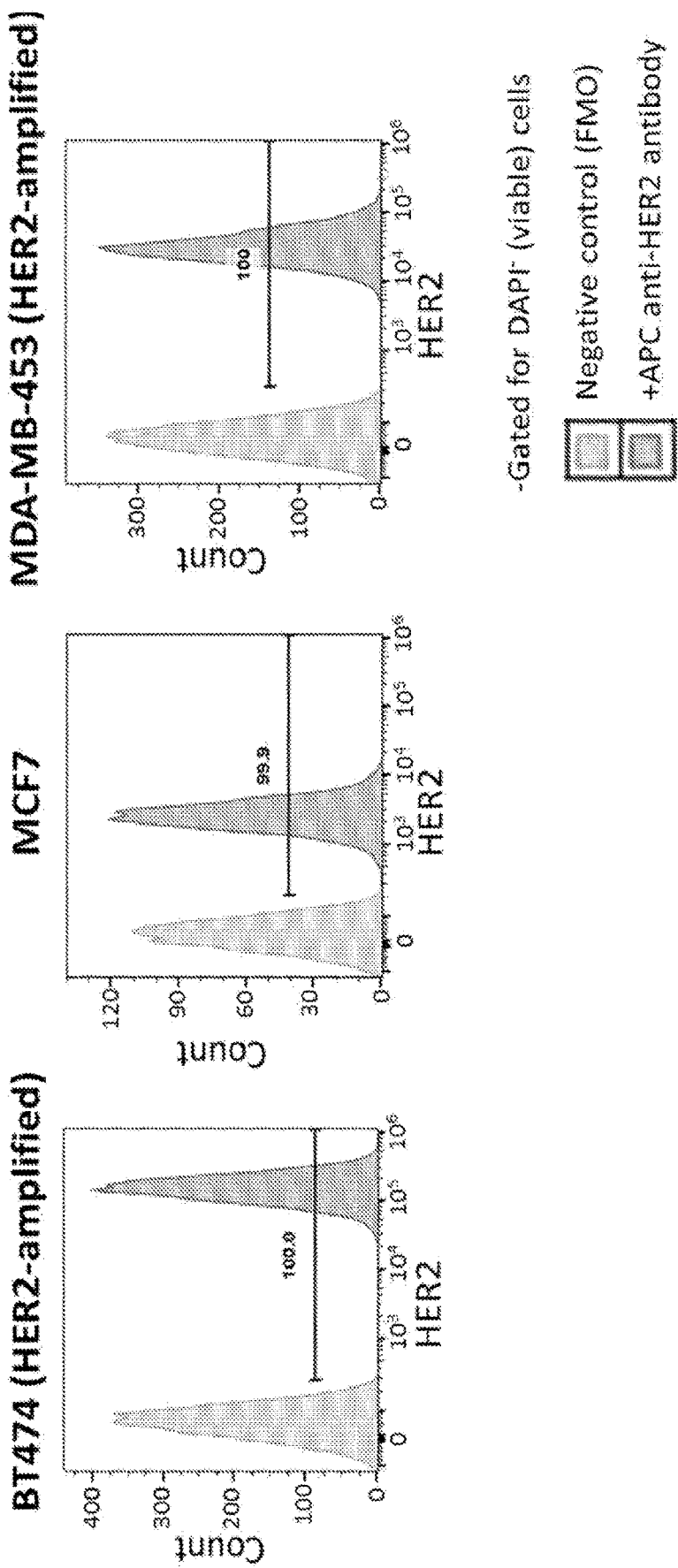
FIG. 6 depicts the results of exemplary experiments demonstrating HER2 labeling of human breast cancer cell (BCC) lines (luminal). Luminal BCC lines were stained with an anti-HER2 antibody conjugated to the fluorochrome APC. The experiment was gated for DAPI⁻ (viable) cells. Histograms show APC-HER2 fluorescence intensity, as determined using an Attune NxT acoustic focusing flow cytometer, compared to "fluorescence-minus-one" (FMO) negative controls, in which the APC anti-HER2 antibody was omitted from the staining reaction. Data analysis was performed using FlowJo analysis software.
Figure 7:
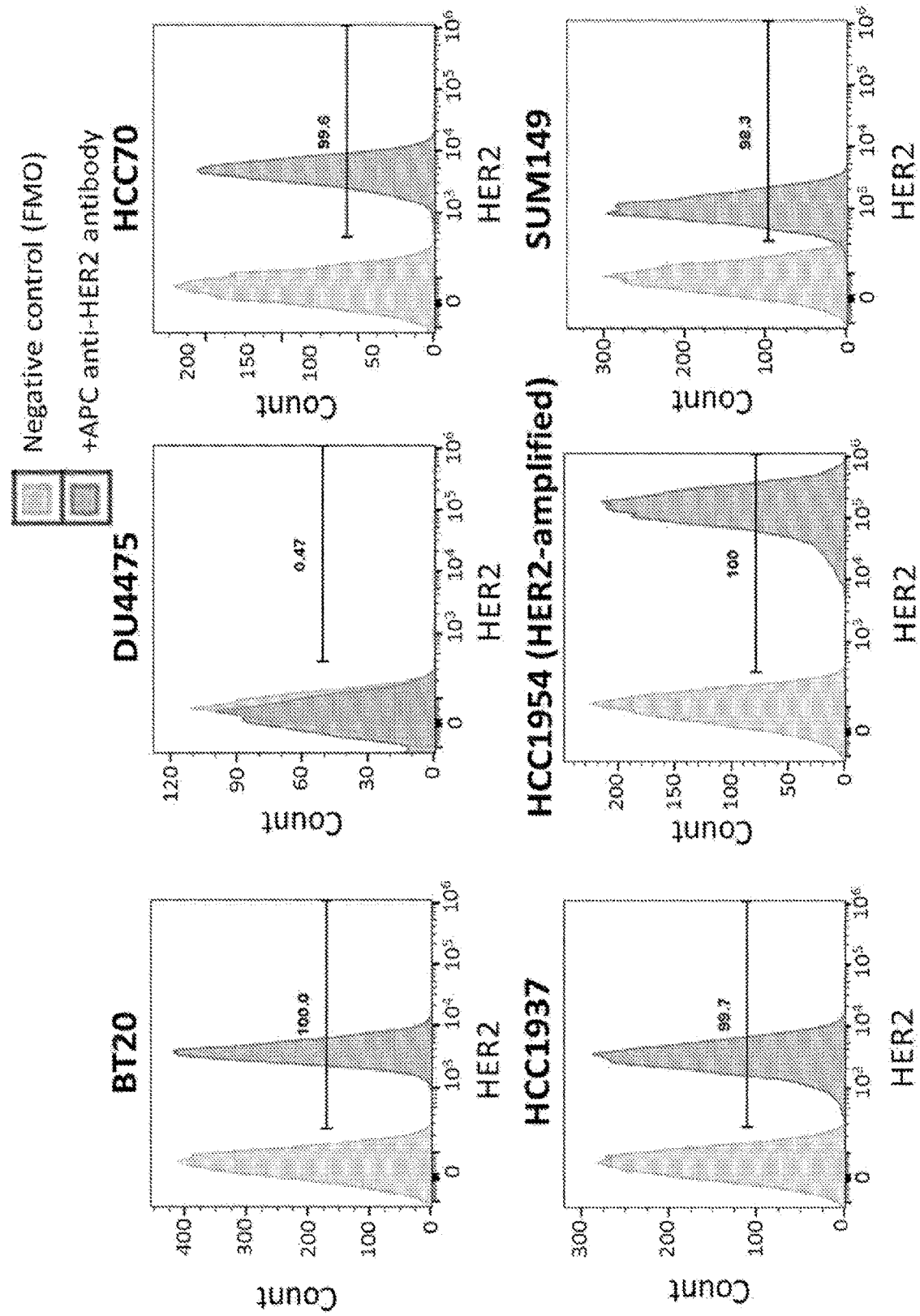
FIG. 7 depicts the results of exemplary experiments demonstrating HER2 labeling of human BCC lines (basal). Basal BCC lines were stained with an anti-HER2 antibody conjugated to the fluorochrome APC. The experiment was gated for DAPI⁻ (viable) cells. Histograms show APC-HER2 fluorescence intensity, as determined using an Attune NxT acoustic focusing flow cytometer, compared to "fluorescence-minus-one" (FMO) negative controls, in which the APC anti-HER2 antibody was omitted from the staining reaction. Data analysis was performed using FlowJo analysis software.
Figure 8:
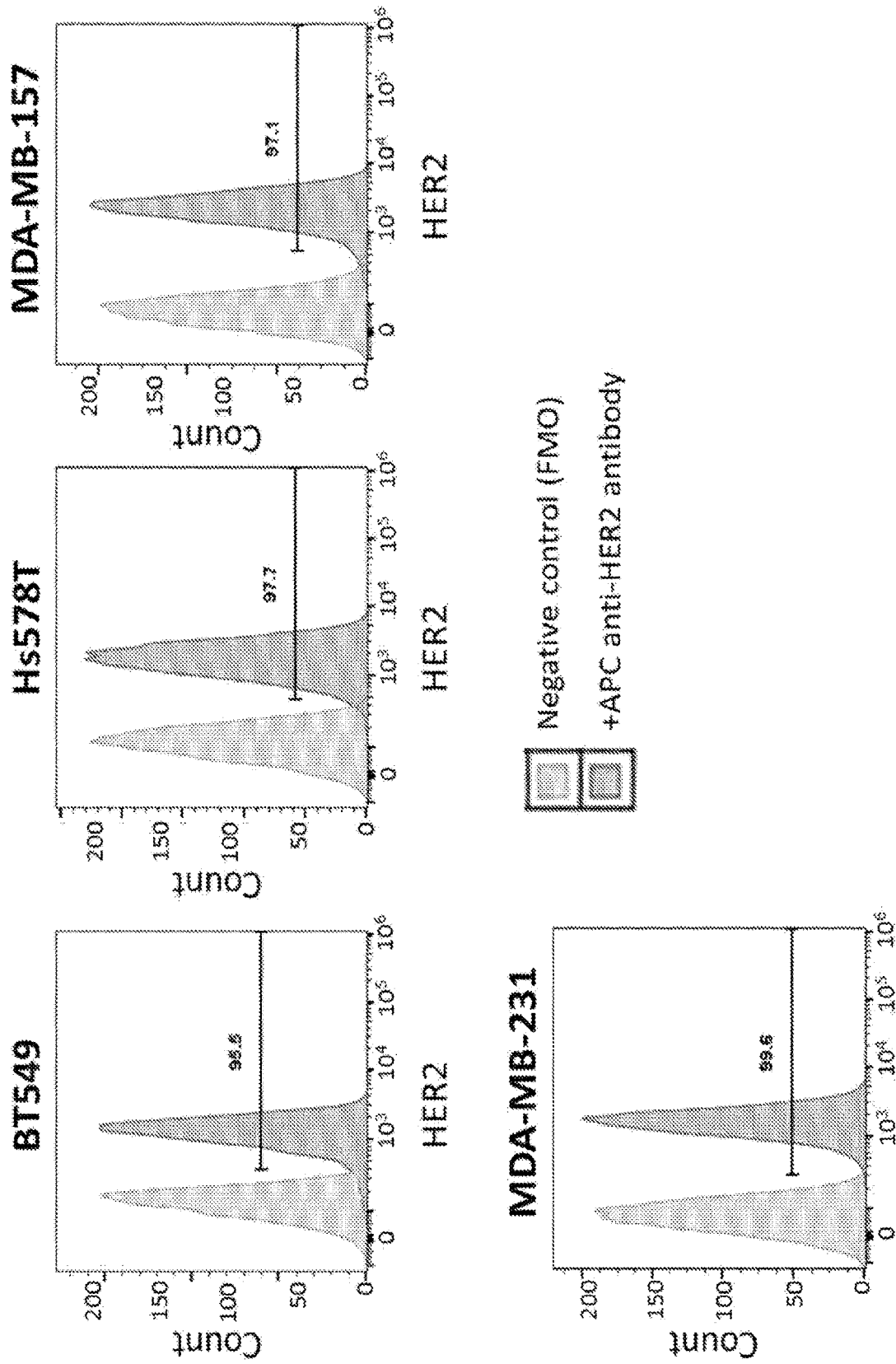
FIG. 8 depicts the results of exemplary experiments demonstrating HER2 labeling of claudin-low BCC lines. Four claudin-low BCC lines were stained with an anti-HER2 antibody conjugated to the fluorochrome APC. The experiment was gated for DAPI⁻ (viable) cells. Histograms show APC-HER2 fluorescence intensity, as determined using an Attune NxT acoustic focusing flow cytometer, compared to "fluorescence-minus-one" (FMO) negative controls, in which the APC anti-HER2 antibody was omitted from the staining reaction. Data analysis was performed using FlowJo analysis software.
Figure 9:
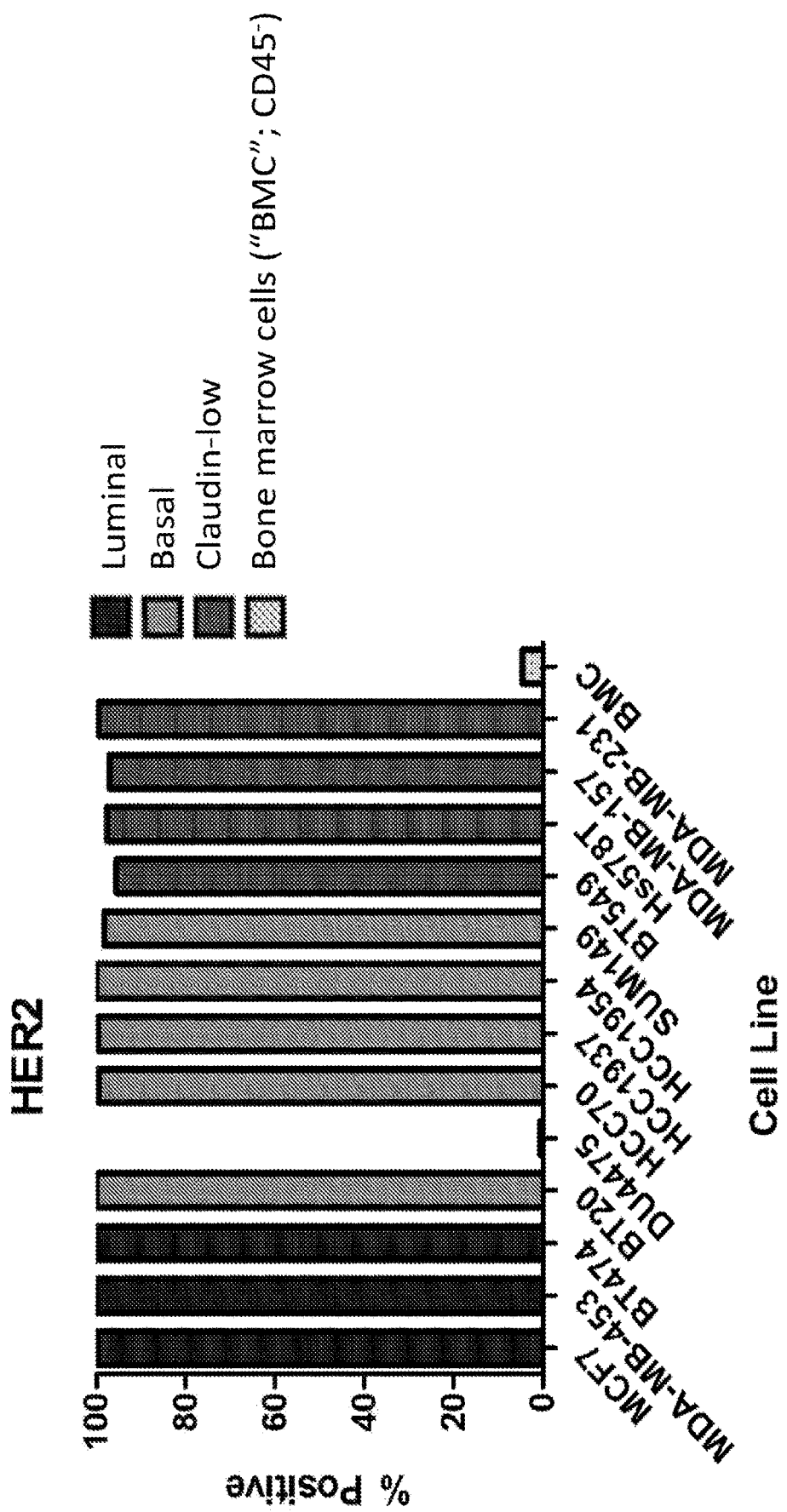
FIG. 9 depicts a summary of the results of exemplary experiments presented in FIG. 6 through FIG. 8 demonstrating the percentage of positive HER2 labeling of human breast cancer cell lines.
Figure 10:
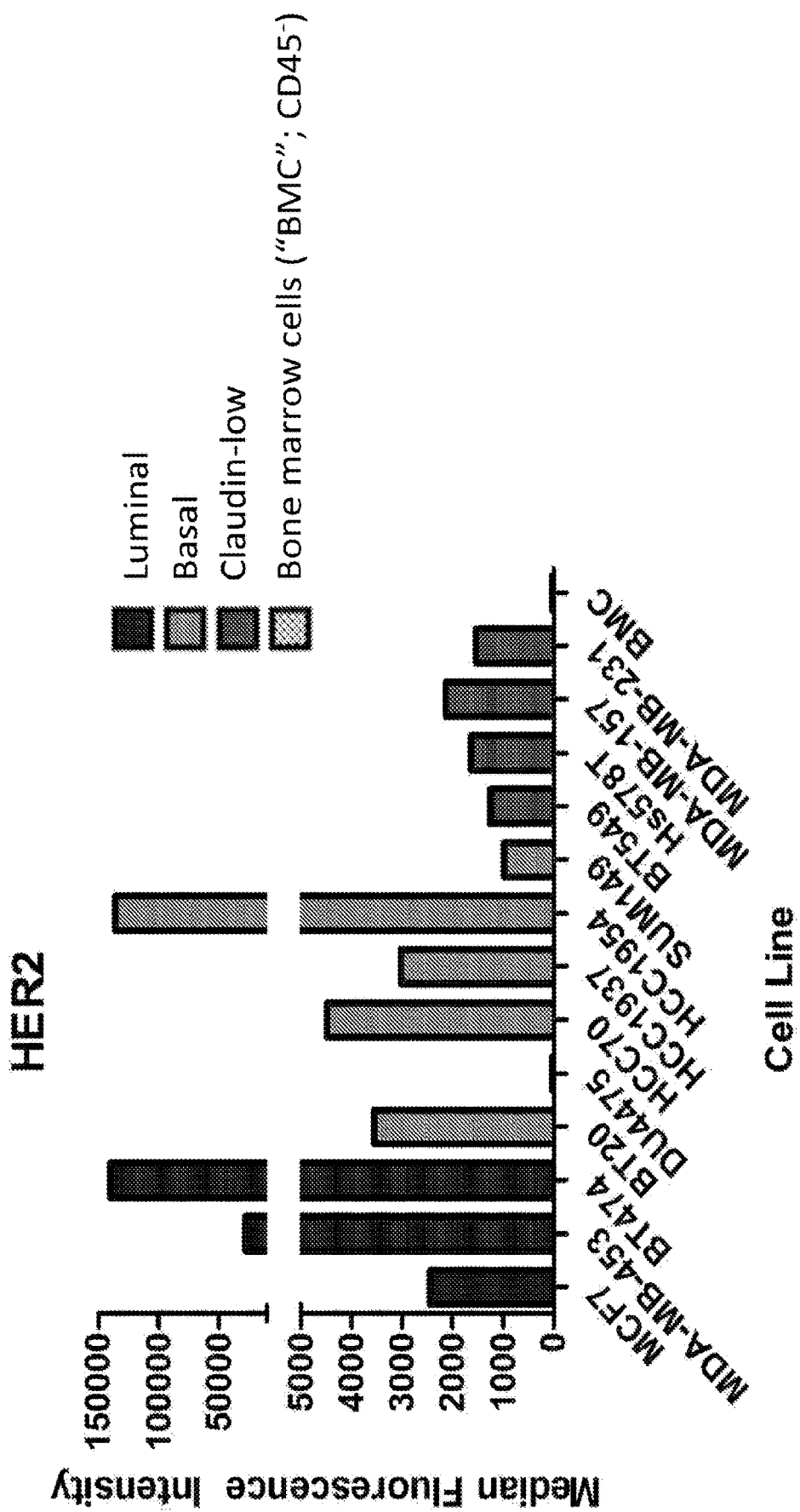
FIG. 10 depicts a summary of the results of exemplary experiments presented in FIG. 6 through FIG. 8 demonstrating the median fluorescence intensity of HER2 labeled cells for different human breast cancer cell lines.

HER2 staining alone was also tested for the ability to effectively label human breast cancer cell (BCC) lines representing different breast cancer subtypes (i.e., luminal, basal, and claudin-low). HER2 effectively labels the tested luminal breast cancer cell lines (≥99.9% of cells in each of these cell lines are HER2-positive), including both HER2-amplified cell lines (BT474 and MDA-MB-453) and cells with endogenous levels of HER2 expression (MCF7). HER2 fluorescence intensities were 10- to 100-fold higher in HER2-amplified cell lines compared to HER2-unamplified MCF7 cells (FIG. 6) HER2 also effectively labels most tested basal breast cancer cell lines; however, the DU4475 cell line does not express cell surface HER2 (FIG. 7). HER2 also effectively labels the tested claudin-low breast cancer cell lines with ≥95% of cells in each of these cell lines being HER2-positive (FIG. 8). Most breast cancer cell lines express detectable levels of cell surface HER2, regardless of subtype (FIG. 9). HER2 levels are greater than 10-fold higher in HER2-amplified cell lines (vs. non-amplified lines), and even claudin-low cell lines express detectable HER2 (FIG. 10).

Figure 11:
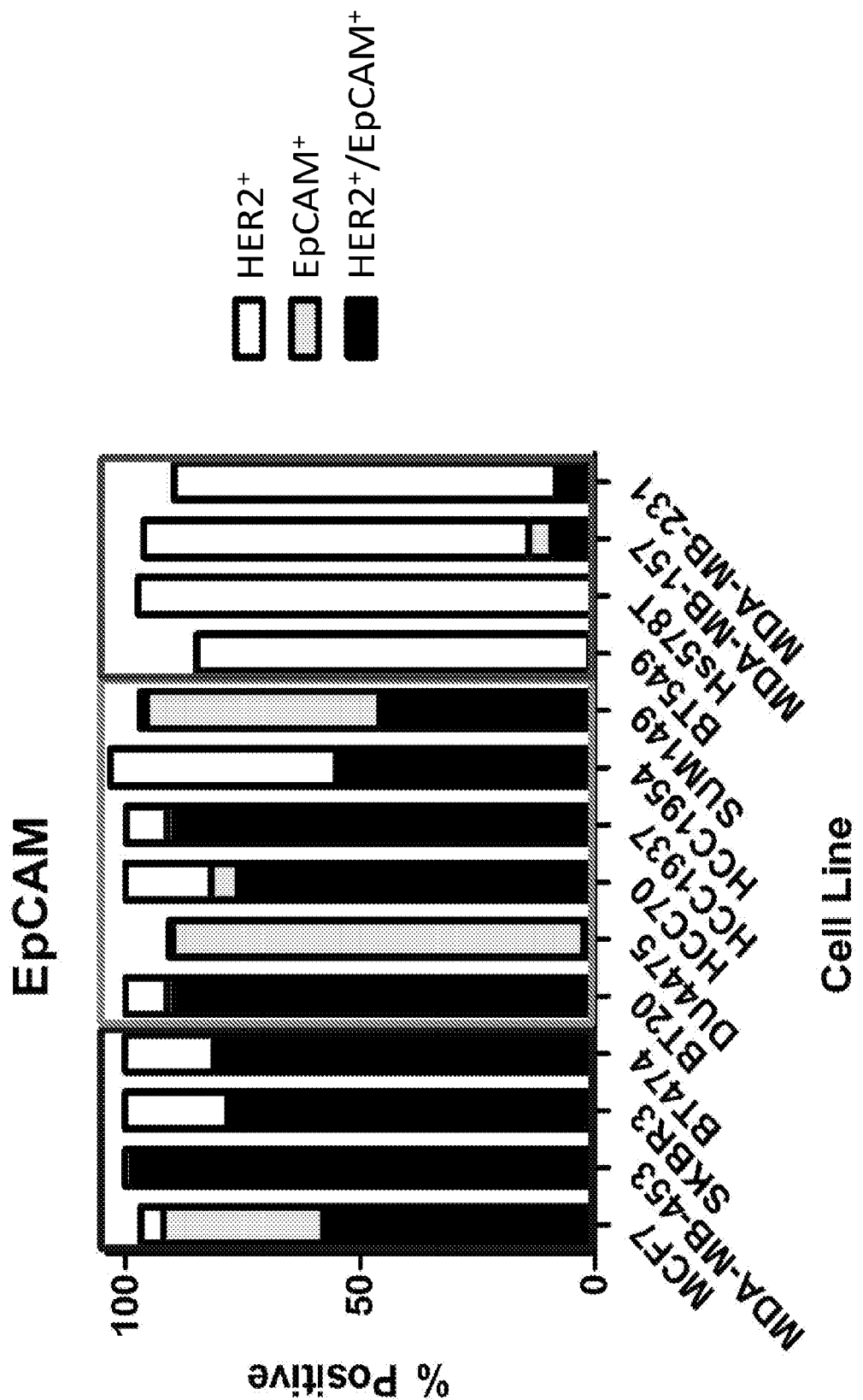
FIG. 11 depicts a summary of the results of exemplary experiments demonstrating the percentage of positive HER2 only, EpCAM only or dual HER2 and EpCAM labeling of human breast cancer cell lines.

When combined, a EpCAM/HER2 panel can detect >85% of cells in all breast cancer cell lines tested, when gated based on FMO controls for each individual cell line (FIG. 11).

Detectable (but low) levels of HER2 expression can be detected in claudin-low cell lines, using a EpCAM/HER2/CD45 staining panel (FIG. 12). Breast cancer cell lines lack expression of the hematopoietic cell marker CD45, as expected (FIG. 12).

Staining Background in Bone Marrow from Healthy Donors

While the EpCAM/HER2 staining panel can effectively label most human breast cancer cell lines, these markers will only be useful for isolation of bone marrow disseminated tumor cells (DTCs) if they differentially label tumor cells versus bone marrow cells (i.e., if tumor cells display higher fluorescence intensities for at least one marker than BMCs). To assess levels of EpCAM and HER2 expression in BMCs, bone marrow aspirates were obtained from healthy donors and subjected to the stain/RBC lyse/no wash protocol (FIG. 13), prior to analysis using the BD Influx™ cell sorter. The selection panel used was EpCAM (FITC) and HER2 (PE) as positive selection markers and CD45 (APC) and DAPI (live/dead) as negative selection markers.

FIG. 14 demonstrates the gating strategy used. First, viable bone marrow cells were identified by DAPI exclusion (DAPI-negative cells). Then gating was employed to analyze only viable cells lacking expression of the hematopoietic marker CD45. EpCAM and HER2 expression were thus analyzed for the DAPI-negative, CD45− negative population of BMCs.

Normal bone marrow from healthy donors contains a small population of CD45− negative cells which express a low level of EpCAM (FIG. 15). This "EpCAM-low" population includes approximately 0.5% of all CD45− negative BMCs. Autofluorescent bone marrow cells were also observed using this staining panel (FIG. 15). Spherotech SPHERO™ Supra Rainbow particles were used to ensure run-to-run consistency, allow use of the same gates on different days, and enable comparison of DTC flow cytometry data from patients over time (FIG. 16).

EpCAM and HER2 levels in human breast cancer cell lines were compared to the expression of these markers in healthy donor bone marrow. A gate was drawn on dot plots of HER2 vs. EpCAM encompassing all DAPI-negative, CD45− negative bone marrow cells. Thus, any cells which display outside of this gate (higher fluorescence intensity for EpCAM, HER2, or both markers) would represent putative bone marrow DTC populations.

The luminal cell line MCF7 and the HER2-amplified basal cell line HCC1954 both express higher levels of HER2 and EpCAM than found in normal bone marrow cells (FIG. 17). Thus, DTCs similar in phenotype to these cell lines would be readily detected by the current staining panel and gating strategy. (Note: The EpCAM-negative/HER2-negative events in the MCF7 and HCC1954 dot plots are carry-over from previously analyzed BMC samples.)

The claudin-low cell lines MDA-MB-231 and Hs578T lack significant EpCAM expression, but these cell lines express HER2 at levels above the normal bone marrow cell "background" (FIG. 18). Thus, a portion of claudin-low breast cancer cell lines (and bone marrow DTCs with corresponding phenotypes) can be detected by a combination of HER2 and EpCAM staining, using the current gating strategy. However, the ability of this staining panel to resolve claudin-low breast cancer cells from BMCs is less effective than for EpCAM-positive luminal or basal breast cancer cells. (Note: The EpCAM-negative/HER2-negative events in the MCF7 and HCC1954 dot plots are carryover from previously analyzed bone marrow samples.)

Luminal and basal breast cancer cells express EpCAM at higher levels than any CD45− negative bone marrow cells from healthy donors; however, EpCAM poorly labels claudin-low breast cancer cells. Flow cytometric analysis has sufficient sensitivity for the detection of endogenous levels of cell surface HER2 expression, even in non-HER2-amplified cell lines. The addition of HER2 staining enables the detection of a portion of claudin-low breast cancer cells, which otherwise would fail to be detected by EpCAM staining alone (FIG. 19).

Bone Marrow Spiking Experiments

To assess the performance of the DTC-Flow assay for the detection and isolation of bone marrow DTCs, spiking experiments were performed, in which titrations of various breast cancer cell lines were spiked into bone marrow aspirates from healthy donors. Samples were processed following the stain/RBC lyse/no wash protocol outlined in FIG. 20, then analyzed and sorted using the BD Influx™ cell sorter with attached pre-enrichment device.

0.5 mL donor bone marrow was spiked with 5000 SKBR3 human breast cancer cells (luminal, HER2-amplified) and subjected to the staining workflow (FIG. 20). Spiked SKBR3 breast cancer cells can readily be distinguished from bone marrow cells (FIG. 21). 1880 cells/5000 cells total (37.6%) of spiked SKBR3 cells were recovered.

MDA-MB-453 human breast cancer cells (luminal, HER2-amplified cell line) were spiked into donor bone marrow, then spiked samples were stained with antibodies against HER2, EpCAM, and CD45, and with DAPI for exclusion of dead cells. The ImageStream® imaging flow cytometer was used to confirm that the sorted cells were HER2-positive, EpCAM-positive, and CD45− negative (FIG. 22).

Sorted tumor cells (and corresponding CD45+ controls) were subjected to TaqMan qPCR analysis of gene expression following transcript amplification using the Single Cell-to-CT™ kit (Thermo Fisher). qPCR analysis demonstrated that sorted tumor cells expressed EpCAM, HER2, and the epithelial marker cytokeratin 18 (KRT18) and lacked CD45 expression, while sorted CD45+ bone marrow cells lacked expression of tumor cell markers (FIG. 23).

Sex-mismatched spiking experiments (spiking female breast cancer cell lines into bone marrow aspirates from healthy male donors) were used to assess the purity of sorted tumor cells. The presence of male-derived bone marrow cells was determined by qPCR-based detection of Y chromosome DNA (USP9Y gene). Initial experiments using titrations of purified male donor DNA demonstrated the ability to sensitively detect the presence of the Y chromosome, enabling detection of even one male-derived bone marrow cell out of 100 total cells (FIG. 24). The detection sensitivity of the assay was less than 10 pg male DNA.

To assess the presence of Y chromosome DNA (USP9Y gene), BD Influx™-sorted cell populations from bone marrow spiking experiments were first subjected to whole genome amplification (WGA) using the Qiagen REPLI-g® WGA kit, followed by TaqMan qPCR-based detection of USP9Y DNA. Total genomic DNA was also isolated from unspiked samples of donor bone marrow and from unspiked human breast cancer cell lines (BT474 and SKBR3) as controls.

While Y chromosome DNA (USP9Y) was readily detected in both total male donor bone marrow (bulk gDNA) and in sorted CD45+ bone marrow hematopoietic cells, the Y chromosome was not detected in 100 cell samples of either BT474 or SKBR3 breast cancer cells ("DTCs") sorted from spiked bone marrow samples (FIG. 24). As the earlier experiments demonstrated, one male-derived bone marrow cell could be detected out of 100 cells total, these findings demonstrate that the sorted tumor cells are pure, without contaminating bone marrow cells (FIG. 25).

Application to Clinical Samples

A bone marrow aspirate from a breast cancer patient with recurrent, metastatic disease was processed by the same protocol used for spiked bone marrow samples and was analyzed/sorted. Using Influx™ sorting gates (gated for DAPI⁻/CD45⁻ cells) which do not identify any DTCs in bone marrow from healthy donors without cancer, a population of putative DTCs (red arrow on plot at top right) was identified in the patient's bone marrow, which express both HER2 and EpCAM (FIG. 26). These cells were sorted for further analysis.

Visualization of the sorted DTCs from this breast cancer patient using the ImageStream® imaging flow cytometer confirmed that these cells were intact, nucleated, expressed the breast cancer cell markers EpCAM and HER2, and lacked expression of the bone marrow hematopoietic cell marker CD45, supporting their identification as DTCs (FIG. 27). Sorted CD45+ bone marrow hematopoietic cells (negative control) lacked expression of the breast cancer cell markers EpCAM and HER2.

An ImageStream® analysis of sorted breast cancer bone marrow DTCs was performed to confirm that these cells also express epithelial cytokeratins not expressed by bone marrow cells (pan-CK antibody), as well as being intact and nucleated (DAPI), expressing the breast cancer cell markers EpCAM and HER2, and lacking expression of the bone marrow hematopoietic cell marker CD45, further supporting their identification as DTCs (FIG. 28).

Sorted DTCs, along with sorted CD45+ bone marrow cells, from the breast cancer patient bone marrow aspirate were subjected to whole genome amplification, followed by targeted Sanger sequencing of exon 20 of the PIK3CA gene, which is frequently mutated in human breast cancers (Ampli1™ PIK3CA kit, Menarini Silicon Biosystems). A PIK3CA 3140 A>G transition mutation was identified in sorted DTCs, a common mutation in breast cancer patients, which is also found in the HCC1954 breast cancer cell line (positive control). Importantly, this mutation was not observed in normal CD45+ bone marrow cells from this patient (FIG. 29). This detection of a breast cancer-associated mutation in sorted DTCs, which is not found in normal bone marrow cells, confirms that the sorted cell population includes true DTCs.

Example 2

Expansion of DTC Marker Panel

The second major component of the invention is the development of an optimized panel of cell surface markers for breast cancer DTC detection in bone marrow. These include a panel of markers for positive selection/phenotypic characterization of DTCs (EpCAM, HER2, CD49C, EGFR, and c-MET), as well as markers for negative selection of hematopoietic cells (CD45 and CD43) or dead/dying cells (DAPI). 8-marker DTC panel on the BD Influx™ cell sorter, staining panel for downstream imaging analysis using the ImageStream® imaging flow cytometer (Amnis/EMD Millipore) in combination with staining for intracellular markers including Ki67, estrogen receptor, and pan-cytokeratin.

Detection 1 in 100,000 nucleated cells. EpCAM, HER2, CD49C, EGFR, and c-MET, CD45 and CD43 and DAPI, intracellular markers including Ki67, estrogen receptor, and pan-cytokeratin.

The results of these experiments are now described.
Identification of Cell Surface Markers for DTC Labeling (Positive Selection)

As some subtypes of breast cancer cells (particularly claudin-low breast cancer cells) were not effectively labeled using the initial staining panel (EpCAM, HER2, CD45, and DAPI), an expanded staining panel is needed in order to detect DTCs across all breast cancer subtypes.

To identify candidate cell surface markers for improved detection of all breast cancer subtypes, a bioinformatics analysis was performed on published gene expression datasets (RNAseq or microarray), including examining expression data from human breast cancer cell lines and human bone marrow cell populations. The analysis identified numerous candidate DTC markers, which were expressed in a high percentage of claudin-low breast cancer cell lines (or in a large proportion of all breast cancer cell lines regardless of subtype, representing candidate pan-breast cancer cell markers) but were not expressed in bone marrow cells.

Candidate markers were tested with commercially-available antibodies, examining expression in a panel of human breast cancer cell lines encompassing all major subtypes, as well as in bone marrow aspirates from healthy donors.

One candidate DTC marker identified by a bioinformatics analysis was CD49C (integrin α3), which was expressed at the mRNA level by human breast cancer cell lines across multiple subtypes, but was not expressed in total bone marrow cells or CD45− negative bone marrow cells, according to published gene expression datasets (FIG. 30).

The ability of CD49C staining alone to effectively label human breast cancer cell (BCC) lines representing different breast cancer subtypes (i.e., luminal, basal, and claudin-low) was tested. FIG. 31 demonstrates that CD49C effectively labels the tested luminal breast cancer cell lines (≥95% of cells in each of these cell lines are CD49C-positive). CD49C also effectively labels the tested basal breast cancer cell lines (≥97.6% of cells in each of these cell lines are CD49C-positive; FIG. 32). CD49C also effectively labels the tested claudin-low breast cancer cell lines (≥99% of cells in each of these cell lines are CD49C-positive), which are not effectively identified using only HER2 and EpCAM staining (FIG. 33).

CD49C staining detects a high percentage (>95%) of cells across all human breast cancer cell lines tested (including luminal, basal, and claudin-low subtypes), and labels nearly 100% of cells in most cell lines (FIG. 34). Basal and claudin-low breast cancer cell lines express higher cell surface levels of CD49C than luminal cell lines (FIG. 35).

The bioinformatics analysis also identified EGFR as a potential marker for claudin-low breast cancer DTCs (FIG. 36). EGFR was expressed at the mRNA level by human breast cancer cell lines across multiple subtypes, particularly basal and claudin-low cell lines, but was not expressed in total bone marrow cells or most CD45− negative bone marrow cells, according to published gene expression datasets.

The ability of EGFR staining alone to effectively label human BCC lines representing different breast cancer subtypes was tested. EGFR does not label a high percentage of luminal breast cancer cells (<30% of cells in each of these cell lines are EGFR-positive; FIG. 37). EGFR effectively labels most tested basal breast cancer cell lines (≥99% of cells in each of these cell lines are EGFR-positive), except for DU4475 cells, which did not express EGFR (FIG. 38). EGFR also effectively labels all tested claudin-low breast cancer cell lines (≥95% of cells in each of these cell lines are EGFR-positive), which are not effectively identified using only HER2 and EpCAM staining (FIG. 39). EGFR staining detects a high percentage (>95%) of cells in all claudin-low human breast cancer cell lines tested, as well as several basal cell lines; however, EGFR staining did not effectively label luminal breast cancer cell lines (FIG. 40). Basal and claudin-low breast cancer cell lines express higher cell surface levels of EGFR than luminal cell lines (FIG. 41).

The bioinformatic analysis also identified c-Met as a potential marker for claudin-low breast cancer DTCs. c-Met was expressed at the mRNA level by human breast cancer cell lines across multiple subtypes, particularly basal and claudin-low cell lines, but was not expressed in total bone marrow cells or most CD45− negative bone marrow cells, according to published gene expression datasets (FIG. 42).

The ability of c-Met staining alone to effectively label human BCC lines representing different breast cancer subtypes was tested. c-Met does not label a high percentage of luminal breast cancer cells (<15% of cells in each of these cell lines are c-Met-positive; FIG. 43). c-Met effectively labels most tested basal breast cancer cell lines (≥90% of cells in each of these cell lines are c-Met-positive), except for DU4475 cells, which did not express c-Met (FIG. 44). c-Met also effectively labels all tested claudin-low breast cancer cell lines (≥95% of cells in each of these cell lines are c-Met-positive), which are not effectively identified using only HER2 and EpCAM staining (FIG. 45). C-Met staining detects a high percentage (>95%) of cells in all claudin-low human breast cancer cell lines tested, as well as several basal cell lines; however, c-Met staining did not effectively label most luminal breast cancer cell lines (FIG. 46). Basal and claudin-low breast cancer cell lines express higher cell surface levels of c-Met than luminal cell lines (FIG. 47).

The relative expression level of each of these three candidate DTC markers (CD49C, EGFR and c-Met) was assessed in breast cancer cell lines versus in CD45− negative bone marrow cells. CD49C identified ~100% of all breast cancer cell lines across subtypes and was not significantly expressed by CD45− negative bone marrow cells (FIG. 48). EGFR identified ~100% of claudin-low cell lines and most basal cell lines, but did not effectively label luminal cell lines. EGFR was not significantly expressed by CD45− negative bone marrow cells (FIG. 49). While c-Met effectively labeled claudin-low and basal breast cancer cell lines, c-Met is also expressed by a subset of CD45− negative bone marrow cells, and only a low percentage of breast cancer cells have higher c-Met levels than these bone marrow cells, limiting the utility of c-Met as a bone marrow DTC identification marker (FIG. 50). However, c-Met detection is still clinically useful for the identification of breast cancer patients who may benefit from available c-Met inhibitors.

Identification of Cell Surface Markers for Bone Marrow Cell Labeling (Negative Selection/Depletion)

Along with identifying an expanded panel of DTC cell surface markers, a bioinformatics analysis was used to identify additional candidate markers for depletion/negative selection of bone marrow hematopoietic and/or stromal cells (in addition to CD45). Candidate bone marrow cell markers were expressed in a high percentage of CD45− negative bone marrow cells, but were not expressed in breast cancer cell lines. Candidate markers were tested, with commercially-available antibodies, examining expression in a panel of human breast cancer cell lines encompassing all major subtypes as well as in bone marrow aspirates from healthy donors.

CD43 (sialophorin) was also identified as a potential marker for depletion of CD45− negative bone marrow cells. CD43 was expressed at the mRNA level by CD45− negative bone marrow mesenchymal stromal cells (MSC) and in total bone marrow, but was not expressed by most human breast cancer cell lines, according to published gene expression datasets (FIG. 51).

Cell surface levels of CD43 were examined in bone marrow cells obtained from healthy donors, following the same bone marrow staining/processing protocol. As shown in FIG. 52, CD43 labeled approximately 17% (16.6+0.61%) of CD45− negative bone marrow cells. Importantly, CD43 staining labeled ~100% of the "EpCAM-low" population of CD45− negative bone marrow cells.

Using the initial staining panel and gating strategy (gating for DAPI-negative/CD45− negative cells), there was a small population of CD45− negative bone marrow cells which express low levels of the DTC marker EpCAM (red circle in plot at top left). In order not to erroneously identify any of these cells as DTCs, the flow sorting gates were set to require DTCs to express higher levels of EpCAM. However, upon adding CD43 as an additional negative selection marker for bone marrow cells (gating for DAPI-negative/CD45− negative/CD43−negative cells), this "EpCAM-low" bone marrow cell population is eliminated, enabling the setting of a less restrictive EpCAM gate for DTC identification (FIG. 53). When only gating for CD45− negative cells, most claudin-low breast cancer cells are not detectable by gating for EpCAM-positive cells (due to EpCAM-low bone marrow cell "background"; FIG. 54). Gating for CD45− negative/CD43−negative cells, a much higher proportion of claudin-low breast cancer cells can be detected by EpCAM staining alone (FIG. 55).

8-Color Expanded Marker Panel for Identification of Breast Cancer Bone Marrow DTCs A panel of eight markers was developed. DTC markers for positive selection included (fluorochromes in parentheses): HER2 (BB515 or FITC), EpCAM (BV786), CD49C (PE), EGFR (PE-Cy7), and c-Met (AF647). DTC markers for negative selection included (fluorochromes in parentheses): CD45 (PE-Cy5)+anti-CD45 IMag particles for magnetic depletion, CD43 (BV605) and DAPI.

The expanded 8-color DTC staining panel was applied to the HER2-amplified breast cancer cell line HCC1954, as well as to Jurkat T cells (as a substitute for bone marrow cells). HCC1954 cells were shown to express all 5 DTC positive selection markers, as expected, while lacking expression of CD45 and CD43, as expected (FIG. 56). Conversely, Jurkat T cells expressed CD45 and CD43, but lacked expression of the 5 DTC markers. The expanded 8-color panel was also applied to a mixture of HCC1954 and Jurkat cells, enabling effective identification of each cell type (FIG. 57).

Fluorescence-minus-one (FMO) controls were performed for each cell type, leaving out one antibody from the panel, demonstrating the specificity of the signal detected in each fluorescence channel (FIG. 58 and FIG. 59).

The 8-color DTC panel was applied to breast cancer cell lines representative of the major subtypes of human breast cancer, along with bone marrow cells from a healthy donor (FIG. 60). All of the breast cancer cell lines were labeled by at least two DTC markers. The 8-color staining panel enables effective identification of all breast cancer cell lines tested, including claudin-low cell lines not readily detectable by EpCAM/HER2 staining. ImageStream® analysis also enables cell-by-cell phenotyping of DTCs, including their expression of therapeutic targets (i.e., HER2, EGFR, and c-Met). This panel could also be combined with additional phenotyping markers (i.e., Ki67, pan-cytokeratin, and estrogen receptor).

BB515 Anti-HER2 (Custom Conjugate) Vs. FITC Anti-HER2

BB515 has a similar excitation/emission spectrum to FITC, but is brighter. Use of BB515 anti-HER2 custom antibody improved resolution of endogenous HER2+ cell lines (i.e., T47D, MDA-MB-231, and Hs578T) (FIG. 61).

Assessment of 8-Color DTC Staining Panel in Bone Marrow from Healthy Donors

The 8-color DTC staining panel was tested on bone marrow from a healthy donor (unspiked or spiked with breast cancer cell lines). For the unspiked experiments, 0.5 mL bone marrow was evaluated (~10 million nucleated cells). DAPI-negative/non-debris (DAPI/FSC), CD45−negative, CD43−negative gating was performed in order to remove DAPI+ (dead), debris, and hematopoietic cells expressing CD45 and/or CD43 (FIG. 62). Gates were then drawn on dot plots for each DTC marker to encompass all DAPI-negative/CD45− negative/CD43− negative events found in control donor bone marrow (FIG. 63). Thus, cells which display outside of any of these gates (higher fluorescence intensity for any of the 5 positive DTC markers) would represent putative bone marrow DTC populations.

The 8-color DTC staining panel was tested on bone marrow from a healthy donor spiked with a mixture of breast cancer cell lines of varying subtype: HCC1954 (basal; HER2-amplified); T47D (luminal); and MDA-MB-231 (claudin-low). All 3 breast cancer cell lines were readily detectable far above the level of bone marrow background using the combination of 5 DTC markers (FIG. 64). MDA-MB-231 (claudin-low) was not well-labeled by HER2/EpCAM alone, but was well-labeled by other markers (particularly CD49C and EGFR).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating or preventing progression of breast cancer in a subject in need thereof, the method comprising the steps of isolating a sample from the subject, contacting the isolated sample with at least one labeled molecule that specifically binds to the cell surface marker CD49C in the sample, detecting binding of the at least one labeled molecule to the cell surface marker CD49C on a disseminated tumor cell (DTC) in the sample using flow cytometry, and administering to the subject an effective amount of a therapeutic agent for the treatment of breast cancer or prevention of breast cancer progression.

2. The method of claim 1, wherein the sample comprises bone marrow cells.

* * * * *